(12) United States Patent
Itoh et al.

(10) Patent No.: US 7,442,797 B2
(45) Date of Patent: Oct. 28, 2008

(54) PLATINUM COMPLEX AND LIGHT EMITTING DEVICE

(75) Inventors: Hisanori Itoh, Kanagawa (JP); Yuji Nakayama, Kanagawa (JP); Takeshi Iwata, Kanagawa (JP); Yoshimasa Matsushima, Kanagawa (JP); Yoji Hori, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/578,237

(22) PCT Filed: Oct. 27, 2004

(86) PCT No.: PCT/JP2004/015889

§ 371 (c)(1),
(2), (4) Date: May 3, 2006

(87) PCT Pub. No.: WO2005/042444

PCT Pub. Date: May 12, 2005

(65) Prior Publication Data

US 2007/0103060 A1 May 10, 2007

(30) Foreign Application Priority Data

Nov. 4, 2003 (JP) .............................. 2003-374861

(51) Int. Cl.
C07F 15/00 (2006.01)
H01J 63/04 (2006.01)
(52) U.S. Cl. ................... 546/6; 546/2; 546/13; 546/14; 313/504
(58) Field of Classification Search ............ 546/2, 546/6, 13, 14; 313/504
See application file for complete search history.

(56) References Cited

U.S. PATENT DOCUMENTS

| 2006/0182992 A1 | 8/2006 | Nii et al. |
| 2006/0202197 A1* | 9/2006 | Nakayama et al. ............ 257/40 |
| 2007/0082284 A1 | 4/2007 | Stoessel et al. |

FOREIGN PATENT DOCUMENTS

| DE | 103 50 722.1 | 5/2005 |
| JP | 02-134643 | 5/1990 |
| JP | 2002-175883 | 6/2002 |
| WO | WO-2001/70395 A2 | 9/2001 |
| WO | WO-2004/108857 A1 | 12/2004 |

OTHER PUBLICATIONS

Lin et al., Chem. Eur. J., 9(6):1263-1272 (2003).
Boenneman et al., Cobalt-Catalyzed One-Step Synthesis of Dipyridines, No. 9, pp. 600-602 (1975).
Zhang et al., Synthetic Communications, 31(8):1129-1139 (2001).
Hannon et al., Tetrahedron Letters, 39:8509-8512 (1998).
Mandon et al.: "Trigonal Bipyramidal Geometry and Tridentate Coordination Mode of the Tripod in FECl2 Complexes with Tris(2-pyridylmethyl)amine Derivatives Bis-α-Substituted with Bulky Groups. Structures and Spectroscopic Comparative Studies" Inorg. Chem. 2002, vol. 41, No. 22, pp. 5364-5372 (Sep. 19, 2002).
Nierengarten et al.: "High Molecular Weight Cu Coordination Polymers and Their Characterisation by Electrospray Mass Spectrometry (ESMS)" Eur. J. Inorg. Chem. 2002, pp. 573-579.
Montalti et al.: "A Luminescent Anion Sensor Based on a Europium Hybrid Complex" J. Am. Chem. Soc. 2001, vol. 123, pp. 12694-12695 (Nov. 20, 2001).
Funeriu et al: "Multiple Expression of Molecular Information: Enforced Generation of Different Supramolecular Inorganic Architectures by Processing of the Same Ligand Information through Specific Coordination Algorithms" Chem. Eur. J. 2000, vol. 6, No. 12, pp. 2103-2111.

(Continued)

*Primary Examiner*—Porfirio Nazario Gonzalez
(74) *Attorney, Agent, or Firm*—Edwards Angell Palmer & Dodge LLP; Peter F. Corless; Dwight D. Kim

(57) ABSTRACT

Provision of a novel platinum complex which is useful as a material for a light-emitting device of good light emission characteristic and light emission efficiency, and a novel light-emitting material that may be utilized in various fields.

A platinum complex represented by the following general formula (1):

(1)

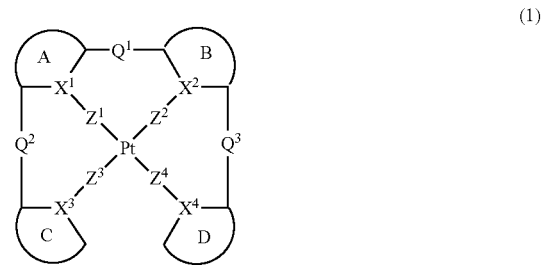

(in which two rings of ring A, ring B, ring C, and ring D represent nitrogen-containing heterocyclic rings which may have a substituent and the remaining two rings of them represent aryl rings or hetero aryl rings which may have a substituent, the ring A and the ring B, the ring A and the ring C or/and the ring B and the rind D may form condensed rings. Two of $X^1$, $X^2$, $X^3$, and $X^4$ represent nitrogen atoms coordination bonded to a platinum atom and the remaining two of them represent carbon atoms or nitrogen atoms. $Q^1$, $Q^2$, and $Q^3$ each represents a bond, oxygen atom, sulfur atom or bivalent group, two of $Z^1$, $Z^2$, $Z^3$, and $Z^4$ represent coordination bonds, and the remaining two of them represent covalent bonds, oxygen atoms or sulfur atoms), and a light-emitting device containing the platinum complex.

16 Claims, 1 Drawing Sheet

OTHER PUBLICATIONS

Grant et al.: "Syntheses, crystal structures and properties of mononuclear chromium (III) and dinuclear vanadium (III) and copper (II) complexes with a bis-bipyridyl ligand" J. Chem. Soc. Dalton Trans., 1999, pp. 3399-3405.

Canary et al.: "Solid State and Solution Characterization of Chiral, Conformationally Mobile Tripodal Ligands" Inorg. Chem. 1998, vol. 37, pp. 6255-6262 (Nov. 11, 1998).

Chotalia et al.: "A conveniently high yield synthesis of 2,2':6,2':6"2":6",2"";6"",2"" sexipyridine and helical transition-metal complexes of substituted sexipyridines" J. Chem. Soc., Dalton Trans., 1996, pp. 4207-4216.

Lehn et al.: "165. Efficient Synthesis of 1,2-Bis(2,2'-bipyrdinyl)ethane and 1,2-Bis(1,10-phenathrolinyl)ethane Ligands by Oxidative Coupling of the Corresponding Monomeric Methylene Carbanions" Helvetica Chimica Acta-vol 71, 1988, pp. 1511-1516.

Tarazona et al.: "Conformational and Dielectric Studies on Polysulfides with Pyridine Groups in the Main Chain" Macromolecules 1992, vol. 25, pp. 5020-5025.

* cited by examiner

PLATINUM COMPLEX AND LIGHT EMITTING DEVICE

TECHNICAL FIELD

The present invention relates to a platinum complex useful as a material for use in a light-emitting device capable of emitting light by conversion of electric energy to light. The platinum complex of the invention is useful as a novel light-emitting material that may be used suitably in the fields, for example, of display devices, display units, back lights, electrophotography, illumination light sources, recording light sources, exposure light sources, light sources for reading, signboards, and interiors.

BACKGROUND ART

At present, research and development have been made vigorously regarding various display devices and, among all, organic electroluminescence devices (hereinafter simply referred to as "organic EL device") have attracted attention as prospective display devices in the next generation since they may obtain light emission of high luminance at low voltage.

Since the organic EL device has higher response speed compared with liquid crystals used so far and emits light by itself, it does not require a back light as in existent liquid crystals and may form a flat panel display of an extremely reduced thickness. The organic EL device is a light-emitting device utilizing the electroluminescence phenomenon and, while it is identical with LED in view of the principle, it has a feature in that an organic compound is used as a light-emitting material.

As an example of organic EL devices using such an organic compound as a light-emitting material, an organic EL device utilizing a multi-layered thin film by a vapor deposition method has been reported. For example, light emission characteristics are improved remarkably compared with existent mono-layered device by using tris(8-hydroxy quinolinate-O,N) aluminum ($Alq_3$) as an electron-transporting material and laminating it with a hole-transporting material (for example, aromatic amine compound).

Then, while it has been vigorously studied for the trend of applying such an organic EL device to multi-color displays in recent years and, for developing a multi-color display of high function, it is necessary to improve the characteristics and the efficiency of the light-emitting devices for respective colors of red, green and blue as three primary colors of light.

As means for improving the characteristics of the light-emitting device, it has also been proposed to utilize a phosphorescent material to a light-emitting layer of an organic EL device. The phosphorescence emission is an emission phenomenon from an excited triplet state caused from the excited singlet state by radiationless transition referred to as an inter-state crossing, and it is known to show higher quantum efficiency compared with the fluorescence emission as an emission phenomenon from the excited singlet state. It is expected that a high luminous efficiency may be attained by using the organic compound showing such a property as the light-emitting material.

For the organic EL devices using such phosphorescent material, those devices using various complexes with iridium as the center metal have been developed up to the present, and the development for complexes using platinum as the center metal has also been progressed. Among them, as an organic EL device using red phosphorescent material, a device of using (2,3,7,8,12,13,17,18-octaethyl-21H,23H-porphynate-N,N,N,N) platinum (II) (Pt(OEP)) for the light-emitting layer has been reported (Patent Document 1).

However, while the platinum complex is a red phosphorescent material of high color purity, the external quantum efficiency is about 4% and further improvement for the luminous efficiency is demanded. Further, it has also been reported that an ortho-metalated platinum complex using a compound having an arylpyridine skeleton as a ligand and using platinum as the metal is useful as a phosphorescent material (Patent Document 2) and a platinum complex using a biaryl skeleton compound as a ligand has also be reported (Patent Document 3).

As described above, various studies have been made vigorously for practical use of display devices in the next generation and, among them, organic EL devices using the phosphorescent material is particularly highlighted with a view point of improving the characteristics of the devices. However, the study has been quite primitive and includes various subjects such as optimization of light emission characteristics, luminous efficiency, color purity, and structure of the devices. For solving such subjects, it has been demanded for the development of novel phosphorescent material and, further, for the development of efficient method of supplying the material.

Patent Document 1: Specification of U.S. Pat. No. 6,303,238
Patent Document 2: JP-A No. 2001-181617
Patent Document 3: JP-A No. 2002-175884

DISCLOSURE OF THE INVENTION

Subject to be Solved by the Invention

The present invention has as an object to provide a novel platinum complex which is useful as a material for use in light-emitting devices of good light emission characteristics and luminous efficiency. Further, the present invention has as an object to provide a novel light-emitting material that may be utilized in various fields.

Means for Solving the Subject

The present inventors have made earnest studies for attaining the foregoing purpose and, as a result, have found that a novel platinum complex of a specified structure shown below has excellent light emission characteristics and luminous efficiency and have accomplished the present invention.

That is, the present invention relates to a platinum complex represented by the following general formula (1):

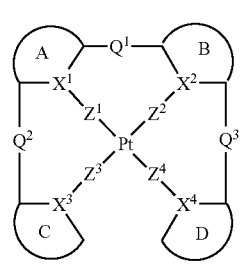

(1)

(wherein two rings of ring A, ring B, ring C, and ring D represent nitrogen-containing heterocyclic rings which may have substituent(s) and the remaining two rings of them represent aryl rings or hetero aryl rings which may have substituent(s), the ring A and the ring B, the ring A and the ring C or/and the ring B and the rind D each may form condensed rings, and each of the rings and $R^1$, $R^2$, $R^3$, $R^4$ or $R^5$ described later may form condensed rings. Two of $X^1$, $X^2$, $X^3$, and $X^4$ represent nitrogen atoms coordination bonded to a platinum atom, and the remaining two of them represent carbon atoms or nitrogen atoms. $Q^1$, $Q^2$, and $Q^3$ each represents independently a bivalent atom (group) or bond providing that $Q^1$, $Q^2$, and $Q^3$ do not represent bonds simultaneously. Two of $Z^1$, $Z^2$, $Z^3$, and $Z^4$ represent coordination bonds and the remaining two of them represent covalent bonds, oxygen atoms or sulfur atoms).

Further, the present invention relates to a platinum complex represented by the following general formula (2):

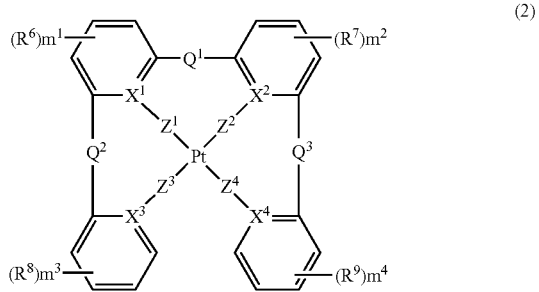

(2)

(wherein $R^6$, $R^7$, $R^8$, and $R^9$ each represent independently alkyl group, halogenated alkyl group, aralkyl group, alkenyl group, alkynyl group, aryl group, amino group, mono- or di-alkyl amino group, mono- or di-aralkyl amino group, mono- or di-aryl amino group, alkoxy group, alkenyloxy group, aralkyloxy group, aryloxy group, heteroaryloxy group, acyl group, alkoxycarbonyl group, aryloxycarbonyl group, acyloxy group, acylamino group, alkoxycarbonylamino group, aryloxycarbonylamino group, aralkyloxycarbonylamino group, sulfonylamino group, sulfamoyl group, carbamoyl group, alkylthio group, aralkylthio group, arylthio group, heteroarylthio group, alkanesulfonyl group, arenesulfonyl group, alkanesulfinyl group, arenesulfinyl group, ureido group, substituted phosphoramidate group, hydroxyl group, mercapto group, halogen atom, cyano group, sulfo group, carboxyl group, nitro group, hydroxamic acid group, sulfino group, hydrazino group, heterocyclic group, trialkylsilyl group or triarylsilyl group, and $R^6$ and $R^7$, $R^6$ and $R^8$, or/and $R^7$ and $R^9$ may form respectively a condensed ring; $m^1$, $m^2$, $m^3$, and $m^4$ each represent the number of $R^6$, $R^7$, $R^8$, and $R^9$ and independently represent an integer of 0 to 3. In a case where each of $m^1$, $m^2$, $m^3$, and $m^4$ is an integer of 2 or greater, plural $R^6$, $R^7$, $R^8$, and $R^9$ may be different from each other and further, a group of $R^6$, a group of $R^7$, a group of $R^8$, and a group of $R^9$ may join to each other to form a condensed ring structure. $Q^1$, $Q^2$, and $Q^3$ each represent independently $-(CR^1R^2)_{n1}-$, $-O(CR^1R^2)_{n1}O-$, $-(O)_{n2}C(=O)(O)_{n3}-$, oxygen atom, sulfur atom, $-NR^3-$, $-BR^{3a}-$, $-S(=O)-$, $-SO_2-$, $-O(SO_2)O-$, $-Si(R^4R^5)-$, $-OSi(R^4R^5)O-$, $-C(=CR^aR^b)-$, or a bond providing that $Q^1$, $Q^2$, and $Q^3$ do not represent bonds simultaneously. $R^1$ and $R^2$ in $Q^1$, $Q^2$, and $Q^3$ each represent independently hydrogen atom, alkyl group, aralkyl group, aryl group, or alkoxy group. n1 represents an integer of 1 to 3 and n2 and n3 each represent independently an integer of 0 or 1. $R^3$ represents hydrogen atom, alkyl group, aralkyl group, or aryl group, and $R^{3a}$ represents alkyl group, aralkyl group or aryl group. $R^4$ and $R^5$ each represent independently alkyl group, aralkyl group or aryl group. $R^a$ and $R^b$ each represent independently hydrogen atom, alkyl group, aralkyl group, aryl group, or cyano group. Further, $R^1$ and $R^2$, $R^4$ and $R^5$, or $R^a$ and $R^b$ may join to each other to form a ring which may contain a hetero atom in the ring together with atoms substituted in each of them. Two of $X^1$, $X^2$, $X^3$, and $X^4$ represent nitrogen atoms coordination bonded to the platinum atom and the remaining two of them represent carbon atoms, and two of $Z^1$, $Z^2$, $Z^3$, and $Z^4$ represent coordination bonds and the remaining two of them represent covalent bonds, oxygen atoms or sulfur atoms).

Further, the present invention relates to a light-emitting device in which a light-emitting layer or a plurality of thin organic compound layers containing the light-emitting layer are formed between a pair of electrodes, wherein at least one layer is a layer containing at least one kind of platinum complex represented by the general formula (1) or the general formula (2).

Further, the present invention relates to a compound represented by the following general formula (3):

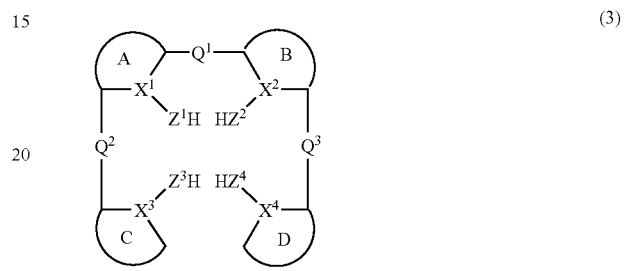

(3)

(wherein two rings of ring A, ring B, ring C, and ring D represent nitrogen-containing heterocyclic rings which may have substituent(s) and the remaining two rings of them represent aryl rings or hetero aryl rings which may have substituent(s), the ring A and the ring B, the ring A and the ring C, or/and the ring A and the rind D may form condensed rings, and each of the rings and $Q^1$, $Q^2$, and $Q^3$ to be described later may form a condensed ring (excluding the case where $Q^1$, $Q^2$, and $Q^3$ are oxygen atoms and sulfur atoms) Two of $X^1$, $X^2$, $X^3$, and $X^4$ represent nitrogen atoms coordination bonded to a platinum atom, and the remaining two of them represent carbon atoms or nitrogen atoms. $Q^1$, $Q^2$, and $Q^3$ each represent independently a bivalent atom (group) or a bond providing that $Q^1$, $Q^2$, and $Q^3$ do not represent bonds simultaneously. In a case where $X^1$, $X^2$, $X^3$, and $X^4$ are nitrogen atoms capable of coordination bond, $Z^1H$, $Z^2H$, $Z^3H$, and $Z^4H$ bonding thereto are not present, in a case where $X^1$, $X^2$, $X^3$, and $X^4$ are carbon atoms, $Z^1$, $Z^2$, $Z^3$, and $Z^4$ bonding thereto represent covalant bonds, oxygen atoms or sulfur atoms, and in a case where $X^1$, $X^2$, $X^3$ and $X^4$ are nitrogen atoms capable of covalent bond, $Z^1$, $Z^2$, $Z^3$ and $Z^4$ bonding thereto represent covalent bonds).

Further, the present invention relates to the compound represented by the following general formula (4):

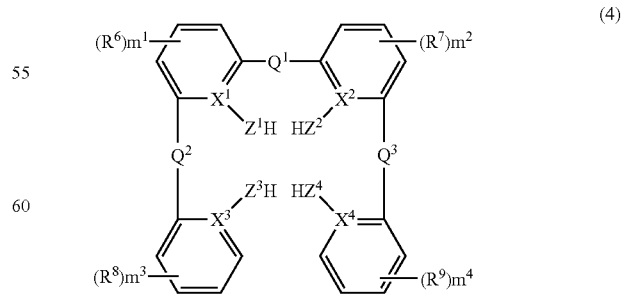

(4)

(wherein $R^6$, $R^7$, $R^8$, and $R^9$ each represent independently alkyl group, halogenated alkyl group, aralkyl group, alkenyl group, alkynyl group, aryl group, amino group, mono- or di-alkyl amino group, mono- or di-aralkyl amino group, mono- or di-aryl amino group, alkoxy group, alkenyloxy group, aralkyloxy group, aryloxy group, heteroaryloxy group, acyl group, alkoxycarbonyl group, aryloxycarbonyl group, acyloxy group, acylamino group, alkoxycarbonylamino group, aryloxycarbonylamino group, aralkyloxycarbonylamino group, sulfonylamino group, sulfamoyl group, carbamoyl group, alkylthio group, aralkylthio group, arylthio group, heteroarylthio group, alkanesulfonyl group, arenesulfonyl group, alkane sulfinyl group, arene sulfinyl group, ureido group, substituted phosphoramidate group, hydroxyl group, mercapto group, halogen atom, cyano group, sulfo group, carboxyl group, nitro group, hydroxamic acid group, sulfino group, hydrazino group, heterocyclic group, trialkylsilyl group or triarylsilyl group, and $R^6$ and $R^7$, $R^6$ and $R^8$ or/and $R^7$ and $R^9$ may form respectively a condensed ring. $m^1$, $m^2$, $m^3$, and $m^4$ each represent the number of $R^6$, $R^7$, $R^8$, and $R^9$ and independently represent an integer of 0 to 3. In a case where each of $m^1$, $m^2$, $m^3$, and $m^4$ is an integer of 2 or greater, plural $R^6$, $R^7$, $R^8$, and $R^9$ may be different from each other and further, a group of $R^6$, a group of $R^7$, a group of $R^8$, and a group of $R^9$ may join to each other to form a condensed ring structure. $Q^1$, $Q^2$, and $Q^3$ each represent independently —$(CR^1R^2)_{n1}$—, —$O(CR^1R^2)_{n1}O$—, —$(O)_{n2}C(=O)(O)_{n3}$—, oxygen atom, sulfur atom, —$NR^3$—, —$BR^{3a}$—, —$S(=O)$—, —$SO_2$—, —$O(SO_2)O$—, —$Si(R^4R^5)$—, —$OSi(R^4R^5)O$—, —$C(=CR^aR^b)$—, or a bond providing that $Q^1$, $Q^2$, and $Q^3$ do not show bonds simultaneously. $R^1$ and $R^2$ in $Q^1$, $Q^2$, and $Q^3$ each represent independently hydrogen atom, alkyl group, aralkyl group, aryl group, or alkoxy group. n1 represents an integer of 1 to 3 and n2 and n3 each represent independently an integer of 0 or 1. $R^3$ represents hydrogen atom, alkyl group, aralkyl group, or aryl group, and $R^{3a}$ represents alkyl group, aralkyl group or aryl group. $R^4$ and $R^5$ each represent independently an alkyl group, aralkyl group or aryl group. $R^a$ and $R^b$ each represent independently hydrogen atom, alkyl group, aralkyl group, aryl group, or cyano group. Further, $R^1$ and $R^2$, $R^4$ and $R^5$, or $R^a$ and $R^b$ may join to each other to form a ring which may contain hetero atom in the ring together with atoms substituted in each of them. Two of $X^1$, $X^2$, $X^3$, and $X^4$ represent nitrogen atoms coordination bonded to the platinum atom and the remaining two of them represent carbon atoms, and two of $Z^1$, $Z^2$, $Z^3$, and $Z^4$ represent coordination bonds and the remaining two of them represent covalent bonds, oxygen atoms or sulfur atoms. H represents a hydrogen atom).

Effect of the Invention

The platinum complex of the present invention is useful as a light-emitting material and, particularly, may prepare an organic EL device having high light emission characteristic, high luminous efficiency, and high durability as a material for use in the organic EL.

Figure 1:
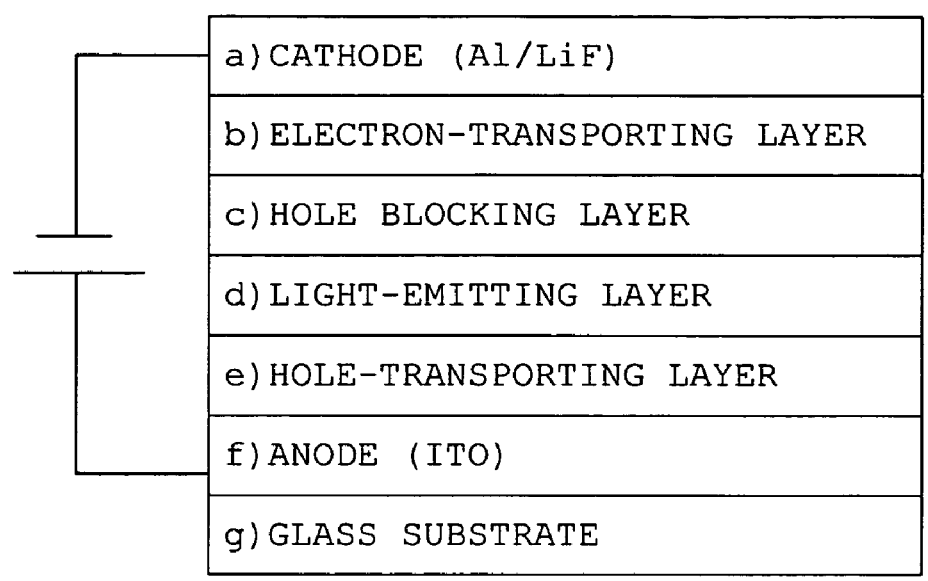
[FIG. 1] is a view showing a constitutional example of an organic EL device using a platinum complex according to the present invention.

DESCRIPTION OF REFERENCES (a) second electrode (metal electrode, cathode)
(b) electron-transporting layer
(c) hole blocking layer
(d) light-emitting layer (host material and dope material)
(e) hole-transporting material
(f) first electrode (transparent electrode, anode)
(g) glass substrate Best Mode for Practicing the Invention The platinum complex of the invention is to be described specifically.

The platinum complex represented by the general formula (1) of the invention is a platinum complex compound having a tetra-dentate ligand comprising the ring A, ring B, ring C and ring D.

In the platinum complex represented by the general formula (1) according to the present invention, the nitrogen-containing heterocyclic ring which may have substituent(s) in the ring A, the ring B, the ring C, and the ring D is a heterocyclic ring having at least one nitrogen atom as a hetero atom and further includes a 5 to 8-membered, preferably, 5- or 6-membered monocyclic, polycyclic or condensed heterocyclic ring which may contain from 1 to 3 hetero atoms comprising, for example, nitrogen atom, oxygen atom, or sulfur atom. The nitrogen atom in the nitrogen-containing heterocyclic ring may be coordinated to the platinum atom. Other rings forming the polycyclic group or condensed ring group include the heterocyclic ring, carbocyclic ring, etc. described above.

Preferred nitrogen-containing heterocyclic ring includes, for example, pyridine ring, diazine ring, triazine ring, diazole ring, triazole ring, thiazole ring, thiadiazole ring, oxazole ring, oxodiazole ring, benzopyridine ring, benzodiazine ring, naphthylidine ring, and 2H-pyrrole ring.

One or more hydrogen atoms on the nitrogen-containing heterocyclic ring in the ring A, ring B, ring C, and ring D of the platinum complex represented by the general formula (1) may be substituted with substituent(s). While the substituent is not particularly restricted so long as it is a group not giving undesired effects on the light emission characteristics, it may include preferably those groups described for $R^6$, $R^7$, $R^8$, and $R^9$ in the platinum complex represented by the general formula (2) to be describe later.

In the platinum complex represented by the general formula (1) of the present invention, the aryl ring in a case where the ring A, ring B, ring C, or ring D is an aryl group or hetero aryl group which may have substituent(s) includes monocyclic, polycyclic, condensed ring type carbocyclic group of 6 to 40 carbon atoms, preferably, 6 to 30 carbon atoms, and, more preferably, 6 to 20 carbon atoms. Further, the hetero aryl group includes 5- to 8-membered, preferably, 5- or 6-membered monocyclic, polycyclic or condensed ring type heterocyclic rings containing from 1 to 3 hetero atoms, for example, nitrogen atom, oxygen atom, or sulfur atom. Other rings forming the polycyclic or condensed ring type of the heterocyclic ring include, for example, the heterocyclic ring groups or the carbocyclic groups described above.

Preferred aryl ring or hetero aryl ring includes, for example, benzene ring, pyridine ring, diazine ring, triazine ring, pyrrole ring, diazole ring, furan ring, thiophene ring, naphthalene ring, benzopyridine ring, benzodiazine ring, benzofuran ring, and benzothiophene ring.

One or more of hydrogen atoms on the aryl ring or the heteroaryl ring in the ring A, ring B, ring C, ring D of the platinum complex represented by the general formula (1) may be substituted with substituent(s). The substituent is not particularly restricted so long as it gives no undesired effect on the light emission characteristic and includes preferably those groups to be described for $R^6$, $R^7$, $R^8$, and $R^9$ in the platinum complex represented by the general formula (2) to be described later.

Successively, bivalent atom (group) represented by $Q^1$, $Q^2$, $Q^3$ in the general formula (1).

The bivalent atom (group) represented by the $Q^1$, $Q^2$, $Q^3$ in the invention exist as a spacer for connecting four ring groups and specific examples include, for example, $-(CR^1R^2)_{n1}-$, $-O(CR^1R^2)_{n1}O-$, $-(O)_{n2}C(=O)(O)_{n3}-$, oxygen atom, sulfur atom, $-NR^3-$, $BR^{3a}$, $-S(=O)-$, $-SO_2-$, $-O(SO_2)O-$, Si $(R^4R^5)-$, $-OSi$ $(R^4R^5)O-$, and $-C(=CR^aR^b)-$.

$R^1$ and $R^2$ in $-(CR^1R^2)_{n1}-$ and $-O(CR^1R^2)O-$ each include independently hydrogen atom, alkyl group, aralkyl group or aryl group, and $R^3$ in $-NR^3-$ includes hydrogen atom, alkyl group, aralkyl group or aryl group, $R^{3a}$ in $BR^{3a}$ includes alkyl group, aralkyl group, and aryl group, $R^4$ and $R^5$ in $-SiR^4R^5-$ and $-O(SiR^4R^5)O-$ each include independently alkyl group, aralkyl group, or aryl group, $R^a$ and $R^b$ in $-C(=CR^aR^b)-$ each include hydrogen atom, alkyl group, aralkyl group, aryl group, or cyano group, and specific examples of the alkyl group, aralkyl group, and aryl group represented by $R^1$, $R^2$, $R^3$, $R^{3a}$, $R^4$, $R^5$, $R^a$, and $R^b$ are same as the case for alkyl group, aralkyl group, or aryl group in the platinum complex represented by the general formula (2) to be described later.

Further, the ring formed by bonding of $R^1$ and $R^2$, $R^4$ and $R^5$, $R^a$ and $R^b$ to each other together with the atoms substituted in each of them includes 5- or 6-membered rings which may contain hetero atoms. Specific rings include cyclopentane ring, cyclohexane ring, tetrahydrofuran ring, tetrahydropyrane ring, dioxolane ring, dioxane ring, furan ring, pyran ring, thiophene ring, benzene ring, tetrahydrosilole ring, and silole ring. Further, the rings may also include bivalent spiro ring from one atom, bivalent saturated rings and aromatic rings from different atoms, etc.

Definitions and specific examples of ring A, ring B, ring C, ring D, $Q^1$, $Q^2$, $Q^3$, $X^1$, $X^2$, $X^3$, $X^4$, $Z^1$, $Z^2$ $Z^3$ and $Z^4$ in the general formula (3) described above are same as those in the general formula (1).

A preferred form of the platinum complex of the invention includes, for example, platinum complex represented by the general formula (2).

In the general formula (2), the alkyl group represented by $R^6$, $R^7$, $R^8$, and $R^9$ includes, for example, linear, branched, or cyclic alkyl groups of 1 to 30 carbon atoms, preferably, 1 to 20 carbon atoms and, more preferably, 1 to 10 carbon atoms and specific examples include, for example, methyl group, ethyl group, n-propyl group, isopropyl group, n-butyl group, tert-butyl group, n-hexyl group, 2-ethylhexyl group, n-octyl group, n-decyl group, n-hexadecyl group, cyclopropyl group, cyclopentyl group, and cyclohexyl group.

The halogenated alkyl group includes, those groups in which one or more of hydrogen atoms in the alkyl group described above are substituted with halogen atom(s) such as a fluorine atom or chlorine atom and specifically includes, for example, perfluoroalkyl groups such as a trifluoro methyl group and pentafluoro ethyl group.

The aralkyl group includes those groups in which one or more hydrogen atoms in the alkyl groups described above are substituted with the aryl group described above (the aryl group may have a substituent such as the alkyl group described above, the alkoxyl group or halogen atom to be described later). A preferred aralkyl group includes arylated alkyl groups of 7 to 30, preferably, 7 to 20 and, more preferably, 7 to 15 carbon atoms which may have substituent(s), and specific examples include, for example, benzyl group, 4-methylbenzyl group, 4-methoxybenzyl group, and 1-phenethyl group.

The alkenyl group includes those having one or more double bonds in a linear or branched carbon chain of 2 to 30 carbon atoms, preferably, 2 to 20 carbon atoms, and, more preferably, 2 to 10 carbon atoms, and specific examples include, for example, vinyl group, allyl group, 2-butenyl group and 3-pentenyl group.

The alkynyl group includes those having one or more triple bonds in a linear or branched carbon chain of 2 to 30 carbon atoms, preferably, 2 to 20 carbon atoms, and, more preferably, 2 to 10 carbon atoms and specific examples include, for example, ethynyl group, 1-propynyl group, and 2-propynyl group.

The aryl group includes aryl groups of 6 to 30 carbon atoms, preferably, 6 to 20 carbon atoms, and, more preferably, 6 to 12 carbon atoms and specific examples include, for example, phenyl group, tolyl group, naphthyl group, and anthrnyl group. The aryl group may have substituent(s) such as the alkyl group described above and alkoxy group and halogen atom to be described later.

The mono- or di-alkyl amino group includes amino groups in which one or two hydrogen atoms are substituted by the alkyl group described above, and specific examples include, for example, methylamino group, dimethylamino group, and diethylamino group.

The mono- or di-aralkyl amino group includes amino groups in which one or two hydrogen atoms are substituted by the aralkyl group described above, and specific examples include, for example, benzylamino group, dibenzylamino group, and 1-phenylethylamino group.

The mono- or di-aryl amino group includes amino groups in which one or two hydrogen atoms are substituted by the aryl group described above, and specific examples include, for example, phenylamino group, diphenylamino group, ditolylamino group, and phenylnaphthylamino group.

The alkoxy group includes those groups in which an oxygen atom is bonded to the alkyl group described above, and specific examples include, for example, methoxy group, ethoxy group, n-propoxy group, isopropoxy group, n-butoxy group, tert-butoxy group, and 2-ethylhexyloxy group.

The alkenyloxy group includes those groups in which an oxygen atom is bonded to the alkenyl group described above, and specific examples include, for example, vinyloxy group and allyloxy group.

The aralkyloxy group includes those groups in which an oxygen atom is bonded to the aralkyl group described above, and specific examples include, for example, benzyloxy group and 1-phenetyloxy group.

The aryloxy group includes those groups in which an oxygen atom is bonded to the aryl group described above, and specific examples include, for example, phenoxy group, tolyloxy group, and naphthyloxy group.

The heteroaryloxy group includes those groups in which an oxygen atom is bonded to the heteroaryl group described above, and specific examples include, for example, 2-pyridyloxy group, 2-pyradinyloxy group, 2-pyrimidinyloxy group, and 2-quinolyloxy group.

The acyl group may be linear or branched and includes, for example, acyl groups of 1 to 18 carbon atoms derived from carboxylic acids such as aliphatic carboxylic acids and aromatic carboxylic acids and specific examples include, for example, formyl group, acetyl group, propionyl group, butyryl group, pivaloyl group, pentanoyl group, hexanoyl group, lauroyl group, stearoyl group, benzoyl group, and acryloyl group.

The alkoxycarbonyl group may be linear, branched or cyclic and includes, for example, alkoxycarbonyl groups of 2 to 19 carbon atoms and specific examples include, for example, methoxy carbonyl group, ethoxy carbonyl group, n-propoxy carbonyl group, 2-propoxy carbonyl group, n-butoxy carbonyl group, tert-butoxy carbonyl group, pentyloxy carbonyl group, hexyloxy carbonyl group, 2-ethylhexyloxy carbonyl group, lauryloxy carbonyl group, stearyloxy carbonyl group, and cyclohexyloxy carbonyl group.

The aryloxy carbonyl group includes, for example, aryloxy carbonyl groups of 7 to 20 carbon atoms and specific examples include, for example, phenoxy carbonyl group, and naphthyloxy carbonyl group.

The acyloxy group includes acyloxy groups derived from carboxylic acids, for example, of 2 to 18 carbon atoms and specific examples include, for example, acetoxy group, propionyloxy group, butyryloxy group, pivaloyloxy group, pentanoyloxy group, hexanoyloxy group, lauroyloxy group, stearoyloxy group, benzoyloxy group, and acryloyloxy group.

The acylamino group includes amino groups in which one hydrogen atom of the amino group is substituted with the acyl group described above, and specific examples include, for example, formylamino group, acetylamino group, propionylamino group, pivaloylamino group, pentanoylamino group, hexanoylamino group, and benzoylamino group.

The alkoxycarbonylamino group includes amino groups in which one hydrogen atom of the amino group is substituted with the alkoxycarbonyl group described above, and specific examples include, for example, methoxycarbonyl amino group, ethoxycarbonyl amino group, n-propoxycarbonyl amino group, n-butoxycarbonyl amino group, tert-butoxycarbonyl amino group, pentyloxycarbonyl amino group, and hexyloxycarbonyl amino group.

The aryloxycarbonylamino group includes amino groups in which one hydrogen atom of the amino group is substituted with the aryloxycarbonyl group described above, and specific examples include, for example, phenyloxycarbonyl amino group.

The aralkyloxycarbonylamino group includes amino groups in which one hydrogen atom of the amino group is substituted with the aralkyloxycarbonyl group described above, and specific examples include, for example, benzyloxycarbonyl amino group.

The sulfonylamino group includes a non-substituted sulfonyl amino group or amino groups in which one hydrogen atom of the amino group is substituted with the sulfonyl group bonded with the alkyl group, aryl group or aralkyl group described above, and specific examples include, for example, methanesulfonyl amino group and p-toluenesulfonyl amino group.

The sulfamoyl group includes a non-substituted sulfamoyl group or mono- or di-substituted sulfamoyl groups in which at least one hydrogen atom on the nitrogen atom is substituted with the alkyl group, aryl group, or aralkyl group described above, and specific examples include, for example, sulfamoyl group, methylsulfamoyl group, dimethylsulfamoyl group, and phenylsulfamoyl group.

The carbamoyl group includes a non-substituted carbamoyl group or mono- or di-substituted carbamoyl groups in which at least one hydrogen atom on the nitrogen atom is substituted with the alkyl group, aryl group, or aralkyl group described above, and includes, for example, a carbamoyl group, methylcarbamoyl group, diethylcarbamoyl group, and phenylcarbamoyl group.

The alkylthio group may be linear, branched or cyclic and includes, for example, alkylthio group of 1 to 6 carbon atoms and specific examples include, for example, methylthio group, ethylthio group, n-propylthio group, 2-propylthio group, n-butylthio group, 2-butylthio group, isobutylthio group, tert-butylthio group, pentylthio group, hexylthio group, and cyclohexylthio group.

The aralkylthio group includes those groups in which a sulfur atom is bonded to the aralkyl group described above, and specific examples include, for example, benzylthio group and 1-phenethylthio group.

The arylthio group includes those groups in which a sulfur atom is bonded to the aryl group described above and specific examples include, for example, phenylthio group and naphthylthio group.

The heteroarylthio group includes those groups in which a sulfur atom is bonded to the heteroaryl group described above, and specific examples include, for example, pyridylthio group, 2-benzoimidazolylthio group, 2-benzoxazolylthio group, and 2-benzothiazolylthio group.

The alkanesulfonyl group include, for example, linear or branched alkanesulfonyl groups of, for example, 1 to 6 carbon atoms and specific examples include, for example, methanesulfonyl group, and ethanesulfonyl group.

The arenesulfonyl group includes, for example, arenesulfonyl groups of 6 to 12 carbon atoms and specific examples include, for example, benzenesulfonyl group, and p-toluenesulfonyl group.

The alkanesulfinyl group include, for example, linear or branched alkanesulfinyl groups of, for example, 1 to 6 carbon atoms and specific examples include, for example, methanesulfinyl group, and ethanesulfinyl group.

The arenesulfinyl group includes, for example, arenesulfinyl groups of 6 to 12 carbon atoms and specific examples include, for example, benzenesulfinyl group, and p-toluenesulfinyl group.

The ureido group includes a non-substituted ureido group or ureido groups in which at least one hydrogen atom of the hydrogen atoms bonded to the two nitrogen atoms is substituted with the alkyl group, aryl group, or aralkyl group described above, and specific examples include, for example, ureido group, methylureido group, and phenylureido group.

The substituted phosphoramidate group includes those groups in which at least one hydrogen atom of the phosphoramidate group is substituted with the alkyl group, aryl group, or aralkyl group described above, and specific examples include, for example, diethyl phosphoramidate group and phenyl phosphoramidate group.

The halogen atom includes a fluorine atom, chlorine atom, bromine atom, and iodine atom.

The sulfo group is $-SO_3H$ group, the hydroxamic acid group is $-CO-NH-OH$ group, the sufino group is $-SO_2H$ group, and the hydrazino group is $-NH-NH_2$ group.

The heterocyclic group is the heteroaryl group as described above, and includes, for example, imidazolyl group, pyridyl group, quinolyl group, furyl group, thienyl group, piperidinyl group, morpholino group, benzoxazolyl group, benzimidazolyl group, and benzothiazolyl group.

The trialkylsilyl group includes silyl groups tri-substituted with the alkyl group described above, and specific examples include, for example, trimethylsilyl group and tert-butyldimethylsilyl group.

The triarylsilyl group includes silyl groups tri-substituted with the aryl group described above, and specific examples include, for example, triphenylsilyl group.

The substituents described above may further be substituted. Further, a group of $R^6$, a group of $R^7$, a group of $R^8$, and a group of $R^9$, may respectively join to each other to form a condensed ring structure or, further, $R^6$ and $R^7$, $R^5$ and $R^8$ or/and $R^7$ and $R^9$ may join to each other to form a condensed ring structure. Specific examples of the condensed ring include, for example, phenanthrene ring, fluorene-9-on ring, 1,10-phenanthroline ring and 4,5-diazafluorene-9-on ring.

$m^1$, $m^2$, $m^3$, and each represent the number for $R^6$, $R^7R^8$, and $R^9$ and each represent independently an integer of 0 to 3. In a case where each of $m^1$, $m^2$, $m^3$, and $m^4$ is an integer of 2 or greater, plural $R^6$, $R^7$, $R^8$, and $R^9$ may be same or different with each other.

The definitions and specific examples for $R^6$, $R^7$, $R^8$, $R^9$, $m^1$, $m^2$, $m^3$, $m^4$, $Q^1$, $Q^2$, $Q^3$, $X^1$, $X^2$, $X^3$, $X^4$, $Z^1$, $Z^2$, $Z^3$, and $Z^4$ in the general formula (4) described above, are same as those in the general formula (2) above.

The platinum complex (1) {or platinum complex (2)} of the invention may be manufactured easily by reacting a complex precursor and a compound represented by the general formula (3) (hereinafter simply referred to as compound (3)) {or a compound represented by general formula (4) (hereinafter simply referred to as compound (4))} under the presence of an appropriate solvent and, optionally, in an inert gas atmosphere as described in the following scheme 1.

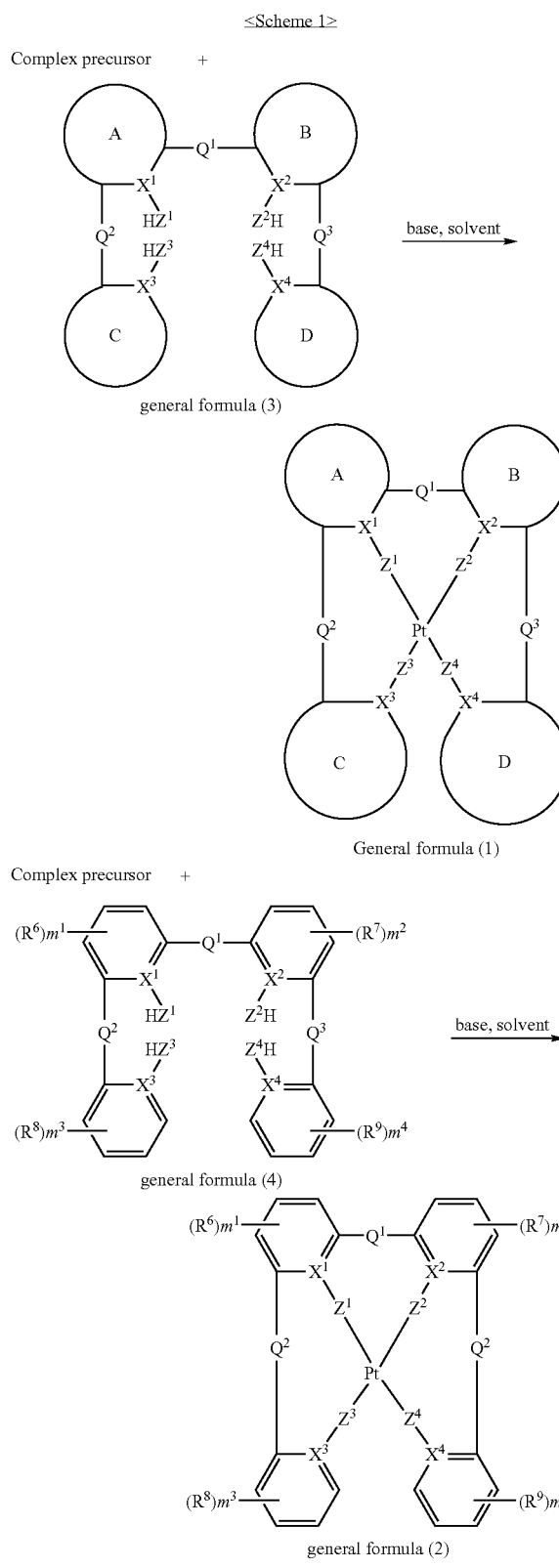

general formula (2)

(in the scheme 1, ring A, ring B, ring C, ring D, $X^1$, $X^2$, $X^3$, $X^4$, $Z^1$, $Z^2$, $Z^3$, $Z^4$, H, $Q^1$, $Q^2$, $Q^3$, $R^6$, $R^7$, $R^8$, $R^9$, and $m^1$, $m^2$, $m^3$, and $m^4$ are defined above).

The complex precursor in the scheme 1 may either be an inorganic platinum compound or an organic platinum complex. Preferred inorganic platinum compound includes $PtY_2$ (Y represents a halogen atom here and hereinafter) and $M_2PtY_4$ (M represents an alkali metal here and hereinafter). The halogen atom represented by Y includes a fluorine atom, chlorine atom, bromine atom, iodine atom, etc. The alkali metal represented by M includes lithium, sodium, potassium, etc.

Specific examples of the inorganic platinum compound include, for example, platinum (II) chloride, platinum (II) bromide, sodium chloro platinate (II), potassium chloro platinate (II), potassium bromo platinate (II), etc.

Preferred organic platinum complexes include, for example, organic platinum complexes represented, by the following general formula (5):

$$Pt(J)_{n4}Y_2 \qquad (5)$$

(in which J represents a neural ligand, n4 represents 1 or 2.).

In the general formula (5), one of the neutral ligands represented by J includes non-conjugated diene compounds, the diene compound may be cyclic or acyclic. In a case where the non-conjugated diene compound is a cyclic non-conjugated diene compound, it may be monocyclic, polycyclic, condensed ring, or bicyclo ring. In a case where J is a non-conjugated diene compound, n4 is 1. Further, the non-conjugated diene compound may also be a non-conjugated diene compound substituted with substituent(s), that is, a substituted non-conjugated diene compound. The substituent is not particularly restricted so long as this is a substituent not giving undesired effects on the manufacturing method of the compound of the invention and includes, for example, those groups same as the substituent described specifically in the explanation for the platinum complex as the example of the substituent. Preferred specific examples of the non-conjugated diene compound include, for example, 1,5-cyclooctanediene, bicyclo[2,2,1]hepta-2,5-diene, and 1,5-hexadiene.

Other neutral ligands than the non-conjugated diene compounds include monodentate neutral ligand and include, more specifically, nitrites such as acetonitrile or benzonitrile, sulfides such as diethyl sulfide, tertiary phosphines such as triphenyl phosphine, tertiary amines such as pyridine, and monoenes such as ethylene. In a case where J is the monodentate ligand, n4 is 2.

The halogen atom represented by Y includes fluorine atom, chlorine atom, bromine atom, iodine atom, etc. and, chlorine atom and bromine atom are particularly preferred.

Specific examples of the platinum complex represented by the general formula (1) and the platinum complex represented by the general formula (2) include, for example, the compounds shown below but not restricted to them.

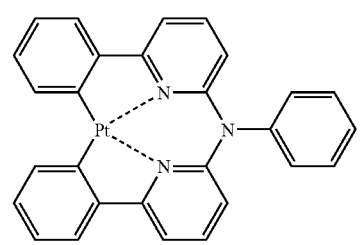

-continued
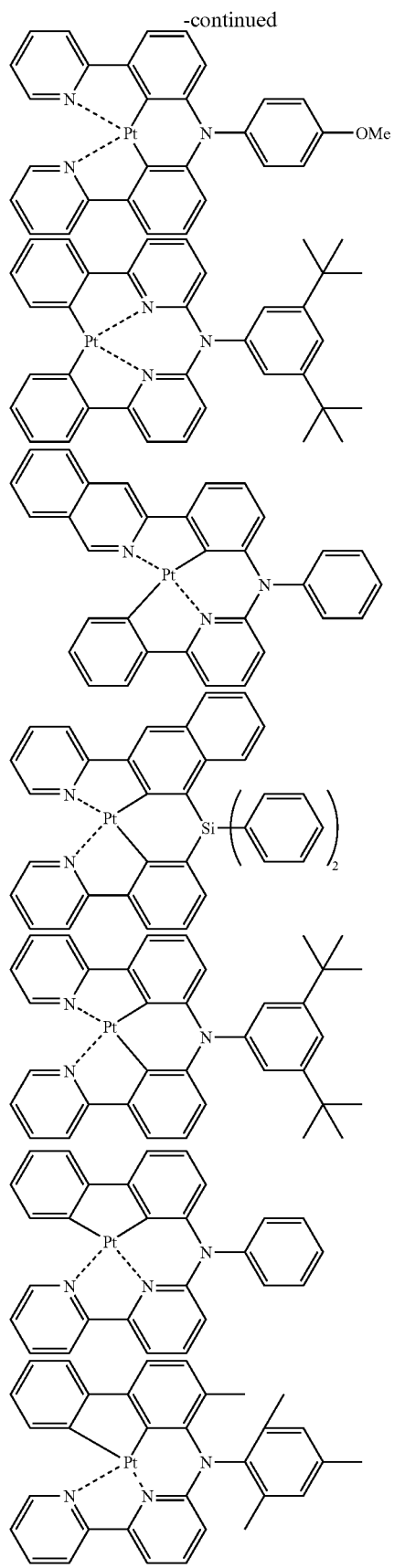
-continued
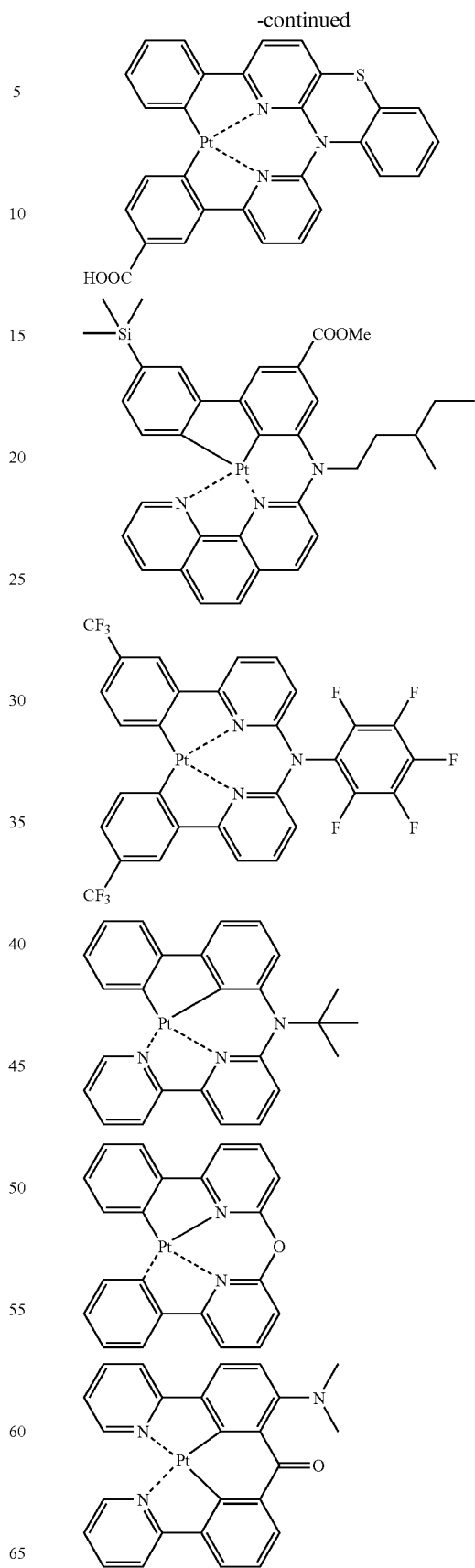

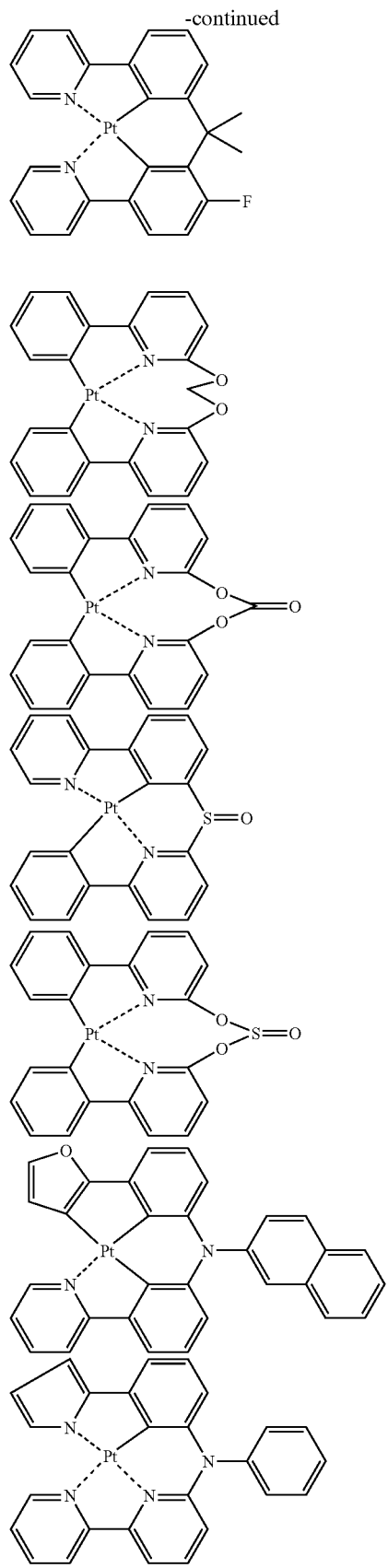
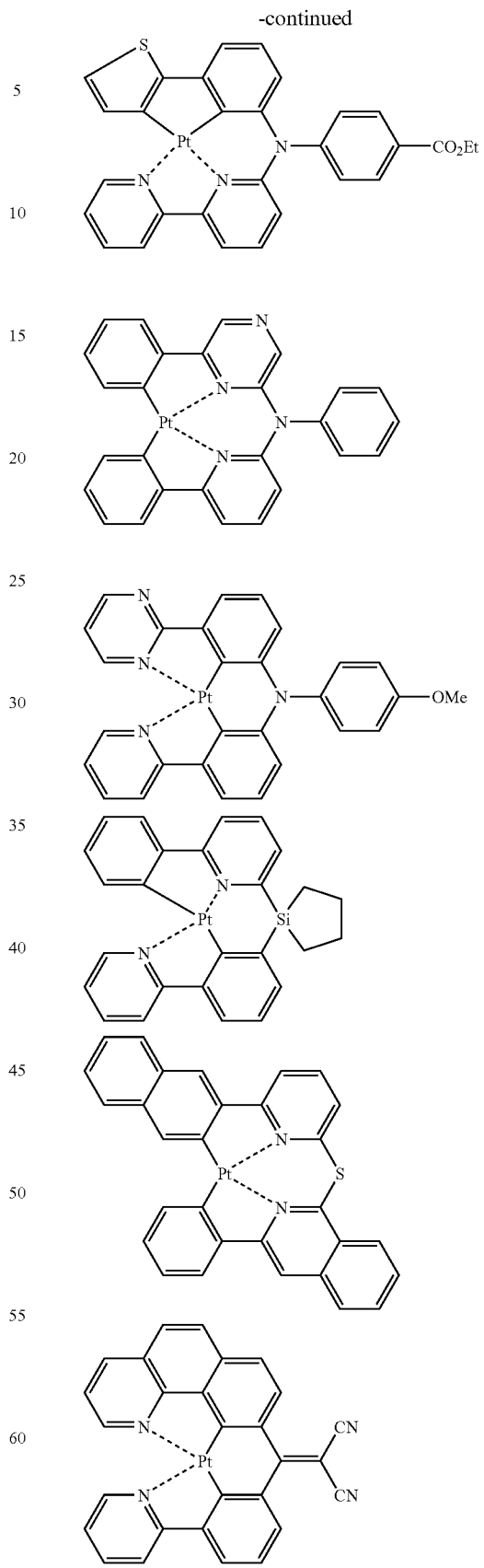

-continued
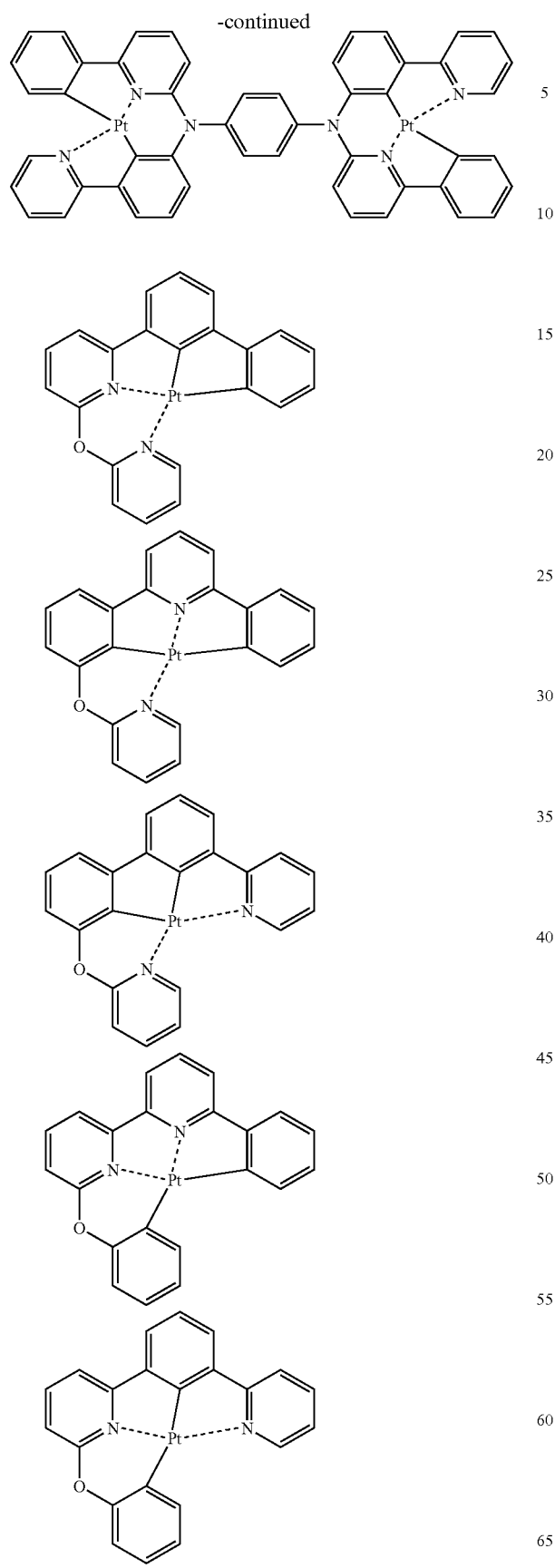
-continued
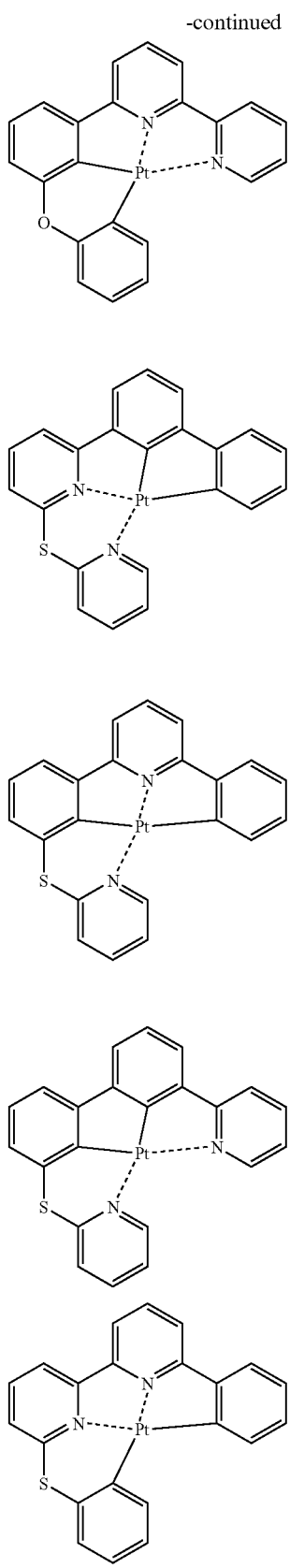

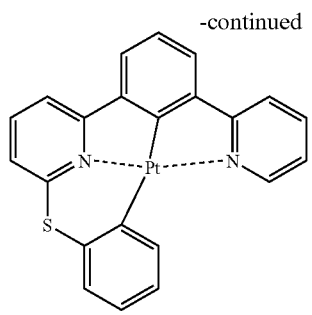
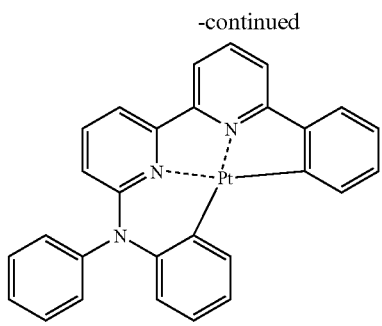
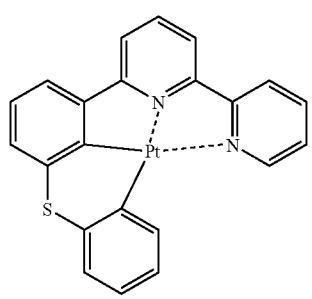
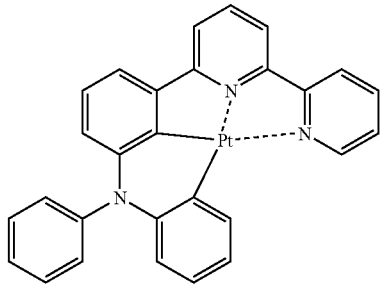
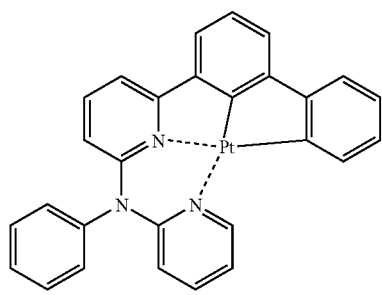
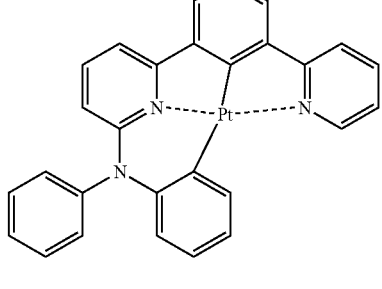
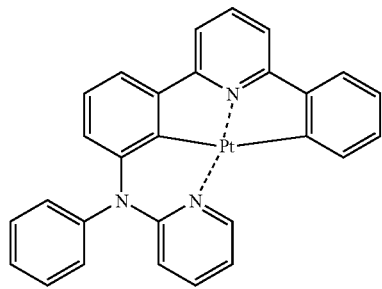
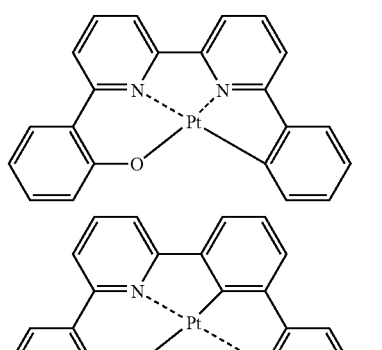
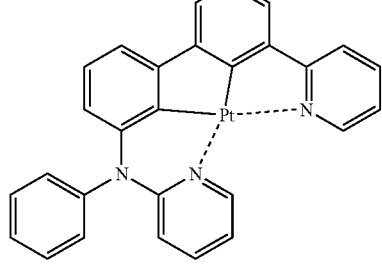
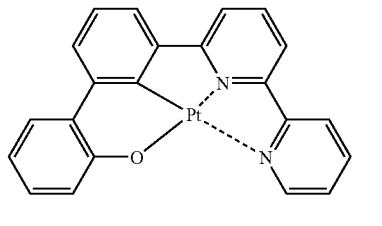

-continued

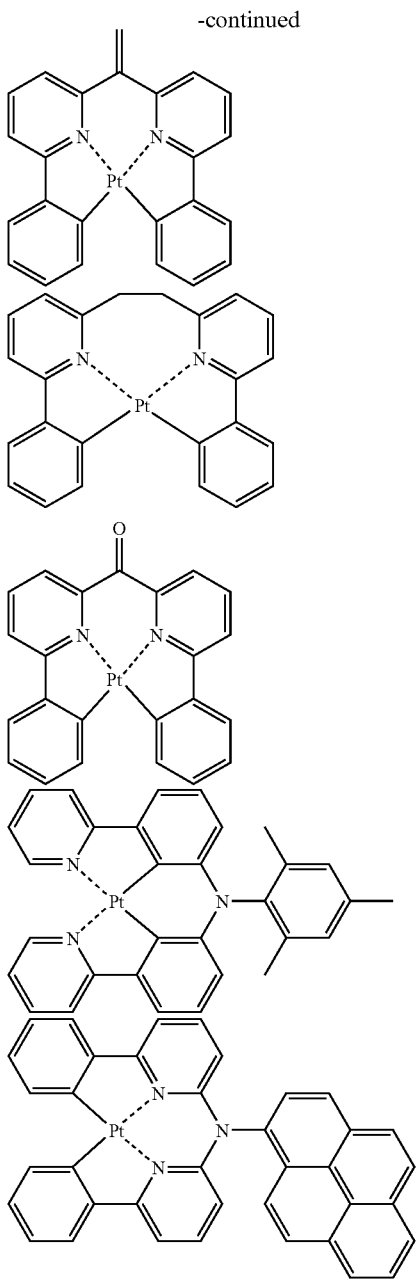

Then, preparation method of the platinum complex according to the present invention is to be described. For the sake of convenience, both of the compound (3) and the compound (4) are collectively referred to as a tetra-dentate ligand.

The amount of the tetra-dentate ligand is usually from 0.5 to 20 equivalents, preferably, from 0.8 to 10 equivalents and, more preferably, from 1.0 to 2.0 equivalents based on the complex precursor.

The preparation method of the compound of the invention is desirably carried out under the presence of solvent(s). Preferred solvent includes, for example, amides such as N,N-dimethylformamide, formamide, and N,N-dimethylacetamide, cyano-containing organic compounds such as acetonitrile and benzonitrile, halogenated hydrocarbons such as dichloromethane, 1,2-dichloroethane, chloroform, carbon tetrachloride, and o-dichlorobenzene, aliphatic hydrocarbons such as pentane, hexane, heptane, octane, decane, and cyclohexane, aromatic hydrocarbons such as benzene, toluene, and xylene, ethers such as diethyl ether, diisopropyl ether, tert-butyl methyl ether, dimethoxy ethane, ethylene glycol diethyl ether, tetrahydrofuran, 1,4-dioxane, and 1,3-dioxolane, ketones such as acetone, methyl ethyl ketone, methyl isobutyl ketone, and cyclohexanone, alcohols such as methanol, ethanol, 2-propanol, n-butanol, and 2-ethoxy ethanol, polyols such as ethylene glycol, propylene glycol, 1,2-propane diol, and glycerine, esters such as methyl acetate, ethyl acetate, n-butyl acetate, and methyl propionate, sulfoxides such as dimethyl sulfoxide, carboxylic acids such as acetic acid, propionic acid, and butyric acid, and water. The solvent may be used each alone or two or more of them may be used being combined properly. More preferred solvent includes amides such as N,N-dimethylformamide and N,N-dimethylacetamide, cyano-containing organic compounds such as acetonitrile and benzonitrile, aromatic hydrocarbons such as benzene, toluene, and xylene, ethers such as ethylene glycol diethyl ether, tetrahyfrofuran, 1,4-dioxane, and 1,3-dioxane, ketones such as acetone, methyl ethyl ketone, and methyl isobutyl ketone, alcohols such as methanol, ethanol, 2-propanol, n-butanol, and 2-ethoxyethanol, polyols such as ethylene glycol, propylene glycol, 1,2-propanediol, and glycerine, esters such as methyl acetate, ethyl acetate, n-butyl acetate, and methyl pripionate, carboxylic acids such as acetic acid, propionic acid, and butyric acid, and water. The solvent may be used each alone or two or more of them may be used being combined properly.

The amount of the solvent to be used is not particularly restricted so long as it may proceed the reaction sufficiently and it is properly selected from a range usually from 1 to 200 times by volume and, preferably, from 1 to 50 times by volume based on the complex precursor.

The reaction temperature is properly selected within a range usually from 25 to 300° C., preferably, from 60 to 250° C., and, more preferably, from 80 to 200° C.

The reaction time is naturally different depending on the reaction conditions such as the reaction temperature, the solvent and the base, and it is properly selected within a range usually from 10 minutes to 72 hours, preferably, from 30 minutes to 48 hours and, more preferably, from 1 to 12 hours.

The platinum complex of the invention may be obtained by optionally carrying out post treatment, isolation and purification after the reaction. The method of the post treatment includes, for example, extraction of reaction products, filtration of precipitates, crystallization by the addition of a solvent and removal of the solvent by distillation. The post treatments may be conducted each alone or in combination. The method of isolation and purification includes, for example, column chromatography, recrystallization and sublimation and they may be conducted each alone or in combination.

Then, the tetra-dentate ligand represented by the compound (3) or the compound (4) is to be described.

The compound (3) and the compound (4) are tetra-dentate ligand having two nitrogen atoms capable of coordination to the platinum metal and two sites capable of bonding to the platinum metal. Ring A, ring B, ring C, ring D, $X^1$, X, $X^2$, $X^3$, $Z^1$, $Z^2$, $Z^3$, $Z^4$, $Q^1$, $Q^2$, $Q^3$, $R^6$, $R^7$, $R^8$, $R^9$, $m^1$, $m^2$, $m^3$, and $m^4$ in the general formula (3) and the general formula (4) are same as those in the compound (1) and the compound (2) as described above.

Specific examples of the compound (3) and the compound (4) include those compounds in which the platinum metal is removed from the specific example of the platinum compound in the invention described above, and a hydrogen atom is added each by one to the atom in covalent bond with the platinum atom.

The tetra-dentate ligand of the invention may be synthesized by carrying out various coupling reactions and other known reactions to aromatic compounds which were known prior to the filing of the present application. The coupling reaction used herein includes, for example, carbon-hetero atom bond forming reactions such as aryl amination and aryl etherfication of using a transition metal, and Ullmann reaction, carbon-carbon bond forming reaction such as Grignard coupling, Negishi coupling, Suzuki coupling, etc. Further, reactions, for example, condensation reaction such as esterification and silyl esterification and halogenation may also be used.

An example of the preparation method for the tetra-dentate ligand of the invention is to be shown below. Since the synthetic method is quite different depending on the structure of the tetra-dentate ligand, the synthetic method described below is merely an example and the preparation method of the tetra-dentate of the invention is not restricted to the method.

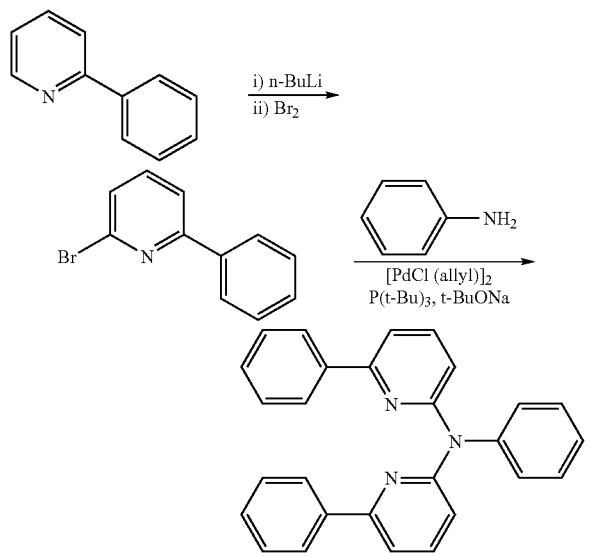

The platinum complex (1) and the platinum complex (2) of the invention are useful as a phosphorescent material in light-emitting devices, particularly, organic EL devices.

Then, the light-emitting device using the platinum complex (1) and the platinum complex (2) of the invention is to be described.

The system, the driving method and the mode of use are not particularly restricted for the light-emitting device so long as this is a device utilizing the platinum complex of the invention, those utilizing the light emission from the platinum complex or those utilizing the platinum complex as the charge transporting material are preferred. Typical light-emitting device includes organic EL devices.

It may suffice that the light-emitting device containing the platinum complex of the invention contains at least one kind of platinum complex and, at least one kind of platinum complex is contained in at least one layer of a light-emitting device in which a light-emitting layer or plural organic compound layers containing the light-emitting layer are formed between a pair of electrodes. While at least one kind of the platinum complex may be contained two or more kinds of them may be contained being combined properly.

The method of forming the organic layer (organic compound layer) of the light-emitting device containing the platinum complex of the invention is not particularly restricted and includes methods such as a resistance-heating vapor deposition, an electron beam, a sputtering, a molecular lamination method, a coating method, and an ink jet method. Of these, the resistance—heating vapor deposition and the coating method are preferred from viewpoints of properties and productivity of the layer.

The light-emitting device containing the platinum complex of the invention is a device in which a light-emitting layer or plural thin organic compound films containing the light-emitting layer are formed between a pair of electrodes of the anode and the cathode and it may also have a hole-injecting layer, a hole-transporting layer, an electron injecting layer, an electron-transporting layer, a protective layer, etc. in addition to the light-emitting layer. Each of the layers may also have other functions respectively. Various materials may be used respectively for the formation of each of the layers.

The anode supplies holes to the hole-injecting layer, the hole-transporting layer, the light-emitting layer, etc. And the anode is made of material such as metals, alloys, metal oxides, electrically conductive compounds or mixtures thereof. A the material, a material having a work function of 4 eV or higher is preferred. Specific examples include electrically conductive metal oxides such as tin oxide, zinc oxide, indium oxide, and indium tin oxide (hereinafter referred to as ITO), or metals such as gold, silver, chromium and nickel, further, mixtures or laminates of the metals and electrically conductive metal oxides, inorganic conductive material such as copper iodide and copper sulfide, organic conductive materials such as polyaniline, polythiophene, polypyrrole, and laminate thereof with ITO. Conductive metal oxides are preferred and, particularly, ITO is preferred with a view point of productivity, high conductivity, and transparency. The film thickness of the anode may be properly selected depending on the material and it is usually selected within a range from 10 nm to 5 μm, more preferably, from 50 nm to 1 μm, and further preferably, from 100 nm to 500 nm.

As the anode, soda lime glass, non-alkali glass, transparent resin substrate, etc. with a layer being formed thereon are usually used. In a case of using glass, use of non-alkali glass is preferred in view of the material in order to decrease ions eluting from the glass. Further, in the case of using soda lime glass, it is preferred to use those applied with barrier coating such as with silica. The thickness of the substrate is not particularly restricted so long as it is sufficient to keep the mechanical strength, and is usually of 0.2 mm or more and, preferably, 0.7 mm or more when the glass is used. Various methods are used for the preparation of the anode depending on the material and, in the case of ITO, for example, the film is formed by a method such as an electron beam method, a sputtering method, a resistance-heating vapor deposition method, a chemical reaction method (sol-gel method, etc.), or a coating method of an ITO dispersion. By treating the anode with cleaning or the like, it is possible to lower the driving voltage and increase the luminous efficiency of the device. For example, in the case of ITO, UV-ozone treatment, plasma treatment, etc. are effective.

The cathode supplies electrons to an electron injecting layer, an electron-transporting layer, a light-emitting layer, etc. and is selected, considering the adhesiveness to a layer adjacent with the negative electrode such as an electron injecting layer, an electron-transporting layer and a light-emitting layer, and ionization potential and stability. As the material for the cathode, metals, alloys, metal halides, metal oxides, electroconductive compounds or mixtures thereof may be used and specific examples include alkali metals such as lithium, sodium, and potassium, and fluorides thereof, alkaline earth metals such as magnesium, and calcium and fluorides thereof, metal, silver, lead, aluminum, sodium-potassium alloy or a mixture of the metals, magnesium-silver alloy or a mixture of the metals, and rare earth metals such as indium and ytterbium and, preferably, those materials with the work function of 4 eV or lower and, preferably, aluminum, lithium-aluminum alloy or a mixture of the metals, magnesium-silver alloy or a mixture of metals.

The cathode may also be formed as a laminate structure containing the compound and mixture described above. While the film thickness of the cathode may be properly selected depending on the material, usually it is preferably within a range from 10 nm to 5 µm, more preferably, from 50 nm to 1 µm and, further preferably, from 100 nm to 1 µm. For the preparation of the cathode, a method such as an electron beam method, sputtering method, resistance-heating vapor deposition method, or a coating method is used and the metal may be vapor deposited as a single element or two or more of ingredients may be vapor deposited together. Further, the electrode may also be formed of an alloy by vapor depositing plural metals together, or a previously prepared alloy may also be vapor deposited. The sheet resistance of the cathode and the anode is preferably lower.

The material for the light-emitting layer may be optional so long as it can form a layer having a function capable of injecting electrons from the anode or the hole-injecting layer, the hole-transporting layer and a function of emitting light by providing re-combination sites for holes and electrons upon application of electric field(s). Typical examples of thereof include carbazole derivatives, benzoxazole derivatives, triphenylamine derivatives, benzimidazole derivatives, benzothiazole derivatives, styrylbenzene derivatives, polyphenyl derivatives, diphenyl butadiene derivatives, tetraphenyl butadiene derivatives, naphthalimide derivatives, coumarine derivatives, perylene derivatives, perynone derivatives, oxadiazole derivatives, aldazine derivatives, pyrralizine derivatives, cyclopentadiene derivatives, bisstyryl anthracene derivatives, quinacridone derivatives, pyrrolopyridine derivatives, thiadiazopyridine derivatives, styrylamine derivatives, aromatic dimethylidene compounds, organic borane derivatives, compounds represented by the general formula (3) or formula (4) of the invention, or various typical, metal complexes including with an 8-quinolinol derivatives and rare earth metal complexes, polymer or oligomer compounds such as poly(N-vinylcarbazole) derivatives, polythiophene, polyphenylene, poly(phenylenevinylene), etc., organic silane derivatives and metal complexes of the invention. The polymer or oligomer compound may be incorporated with the platinum complex of the invention as a partial structure. The material for the light-emitting layer is not restricted to the specific examples described above. The light-emitting layer may be of a single layered structure comprising one or more of the materials described above or may be of a multi-layered structure comprising plural layers each of an identical composition of or different kinds of compositions. The thickness of the light-emitting layer is not particularly restricted and, usually, it is, preferably, selected within a range from 1 nm to 5 µm, more preferably, from 5 nm to 1 µm and, further preferably, from 10 nm to 500 nm. The preparation method of the light-emitting layers is not particularly restricted and includes a method such as an electron beam method, a sputtering method, a resistance-heating vapor deposition method, a molecular lamination method, a coating method (spin coating method, casting method, dip-coating method, etc.), an ink jet method, an LB method, etc. and preferably includes the resistance-heating vapor deposition method and the coating method.

The material for the hole-injecting layer and the hole-transporting layer is optional so long as it has a function of injecting holes from the anode, a function of transporting the holes and a function of forming barriers to electrons injected from the cathode. Specific examples include, carbazole derivatives, triazole derivatives, oxadiazole derivatives, oxazole derivatives, imidazole derivatives, polyarylalkane derivatives, pyrazoline derivatives, pyrazolone derivatives, phenylenediamine derivatives, arylamine derivatives, amino-substituted chalcone derivatives, styryl anthracene derivatives, fluorenone derivatives, hydrazone derivatives, stilbene derivatives, silazane derivatives, aromatic tertiary amine compounds, styrylamine compounds, aromatic dimethylidine compounds, porphyrin compounds, polysilane compounds, poly(N-vinylcarbazole) derivatives, aniline copolymer, conductive polymeric oligomers such as thiophene oligomers and polythiophene, organic silane derivatives, organic borane derivatives, phthalocyanine derivatives, compounds represented by the general formula (3) or (4) of the invention, platinum complexes of the invention, etc. with no restriction to them. The thickness of the hole-injecting layer and the hole-transporting layer is not particularly restricted and usually it is, preferably, selected within a range from 1 nm to 5 µm, more preferably, from 5 nm to 1 µm and, further preferably, from 10 nm to 500 nm. The hole-injecting layer and the hole-transporting layer may be of a single layered structure comprising one or more of the materials described above or may be of a multi-layered structure comprising plural layers of an identical composition or of different kinds of compositions. As the method of preparing the hole-injecting layer and the hole-transporting layer, a vapor deposition method, an LB method, a method of coating the hole-injecting and transporting material being dissolved or dispersed in a solvent (spin coating method, casting method, dip-coating method, etc.), or ink jet method may be used. In the case of the coating method, the material may be dissolved or dispersed together with a resin ingredient. The resin ingredient includes, for example, poly(vinyl chloride), polycarbonate, polystyrene, poly(methyl methacrylate), poly(butyl methacrylate), polyester, polysulfone, poly(phenylene oxide), polybutadiene, poly(N-vinylcarbazole), hydrocarbon resin, ketone resin, phenoxy resin, polyamide, ethyl cellulose, vinyl acetate, ABS resin, alkyd resin, epoxy resin and, silicone resin.

The material for the electron injecting layer and the electron-transporting layer is optional so long as it has a function of injecting electrons from the cathode, a function of transporting electrons and a function of forming barriers to holes injected from the anode. As the ionization potential for the hole blocking layer having a function of forming barriers to holes injected from the anode, those higher than the ionization potential of the light-emitting layer are selected.

Specific examples include triazole derivative, oxazole derivative, polycyclic compounds, heterocyclic compounds such as bathocuproin, oxadiazole derivatives, fluorenone derivatives, diphenylquinone derivatives, thiopyrane dioxide derivatives, anthraquinone dimethane derivatives, anthrone derivatives, carbodiimide derivatives, fluorenilydene methane derivatives, distyrylpyrazine derivatives, acid anhydrides of aromatic tetra carboxylic acids such as naphthalene tetracarboxylic acid, or perylene tetracarboxylic acid, phthalocyanine derivatives, and 8-quinolinol derivatives, metal phthalocyanine, metal complexes having benzoxazole or benzothiaole as a ligand, organic silane derivatives, organic borane derivatives, the compound represented by the general formula (3) or formula (4) of the invention, poly(N-vinylcarbazole) derivatives, polymer or oligomer compounds such as polythiophene, polyphenylene, and poly(phenylene vinylene), and platinum complex of the invention. The platinum complex of the invention may be contained as a partial structure in the polymer or oligomer compound. The materials for the electron injecting layer and the electron-transporting layer is not restricted to them. The thickness of the electron injecting layer and the electron-transporting layer is not particularly restricted and usually it is, preferably, selected within a range from 1 nm to 5 μm, more preferably, from 5 nm to 1 μm and further preferably, from 10 nm to 500 nm. The electron injecting layer and the electron-transporting layer may be of a single layered structure comprising one or more of the materials described above or may be of a multi-layered structure comprising plural layers of an identical composition or of different kinds of compositions. As the method of preparing the hole-injecting layer and the hole-transporting layer, a vapor deposition method, LB method, a method of coating the hole-injecting and transporting material being dissolved or dispersed in a solvent (spin coating method, casting method, dip-coating method, etc.), or ink jet method may be used. In the case of the coating method, the material may be dissolved or dispersed together with the resin ingredient(s) and the resin ingredient exemplified for the case of the hole-injecting layer and the hole-transporting layer may be applied.

The material for the protective layer may be optional so long as if has a function of inhibiting matters that promote degradation of the device such as moisture or oxygen from intruding into the device. Specific examples include, metals such as indium, tin, lead, gold, silver, copper, aluminum, titanium, and nickel, metal oxides such as magnesium oxide, silicon oxide, dialuminum trioxide, germanium oxide, nickel oxide, calcium oxide, barium oxide, diiron trioxide, diytterbium trioxide, and titanium oxide, metal fluorides such as magnesium fluoride, lithium fluoride, aluminum fluoride, or calcium fluoride, polyethylene, polypropylene, poly(methyl methacrylate), polyimide, polyurea, poly(tetrafluoroethylene), poly(chloro trifluoroethylene), poly(dichloro fluoro ethylene), copolymer of chloro trifluoro ethylene and dichloro difluoro ethylene, copolymer obtained by copolymerizing a monomer mixture containing tetrafluoro ethylene and at least one comonomer, fluoro-containing copolymer having a cyclic structure in the copolymer main chain, a water absorbing substance with the percent water absorption of 1% or more, and a moisture proof material with the percent water absorption of 0.1% or less. There is no particular restriction also on the method of forming the protective film and, for example, a method such as a vacuum vapor deposition method, a sputtering method, a reactive sputtering method, an MBE (Molecular Beam Epitaxy), a cluster ion beam method, an ion plating method, a plasma polymerization method (high frequency-excited ion plating method), a plasma CVD method, a laser CVD method, a thermal CVD method, a gas source CVD method, and a coating method is applicable.

All the contents described in the specification of Japanese Patent Application No. 2003-374861 are incorporated in the present specification.

The present invention is to be described specifically with reference to Reference Examples and examples, but the invention is no way restricted by them. Apparatus used for measuring physical properties in the Reference Examples and the Examples are as shown below.

1) $^1$H-NMR spectrum: DRX-500 model apparatus (manufactured by Bruker Co.) or

GEMINI2000 model apparatus (manufactured by Varian Inc.)

Internal Standard Substance: Teteramethyl Silane

2) Analysis for absorption spectrum: V-550 (manufactured by JASCO)

3) Analysis for emission spectrum: F-4500 (manufactured by Hitachi Ltd.)

REFERENCE EXAMPLE 1

Preparation of 2-bromo-6-phenylpyridine

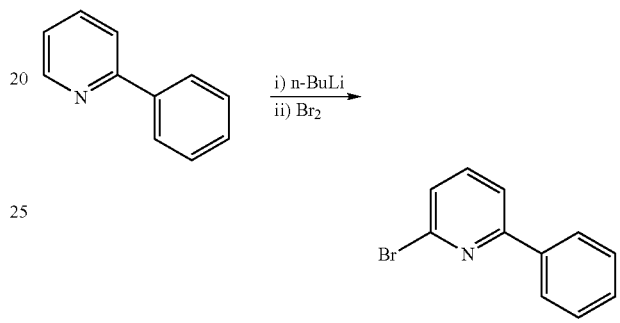

The title compound was prepared according to the method described in a document (J. Org. Chem., 2003, 68, 4918-4992).

In a nitrogen atmosphere, a mixture of dimethylaminoethanol (2.1 ml) and a hexane solution of 2-phenylpyridine (2.17 g) was cooled to −78° C., then a hexane solution of n-butyllithium (1.6 M, 26.5 ml) was added dropwise thereto. After dropwise, the mixture was allowed to warm to 0° C., then stirred for 2 hours. Thereafter, a toluene solution of bromine (2.5 ml) was added to the mixture at 0° C., then stirred for 2 hours additionally. Then, the mixture was stirred at room temperature for 1 day. Thereafter, the residual bromine of reaction mixture was neutralized by aqueous sodium thiosulfate, the mixture was extracted with toluene, the solvent was distilled off, and the residue was purified by silica gel column chromatography, thereby obtaining desired white solid (1.30 g).

$^1$H-NMR(CDCl$_3$): 7.39-7.53, 7.55-7.71(m, 2H), 7.96-8.02 (m, 2H)

EXAMPLE 1

Preparation of N,N-bis(6-phenylpyridine-2-yl)aniline

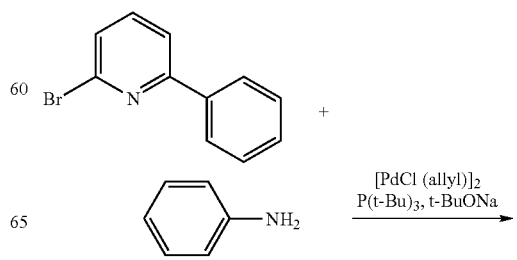

-continued

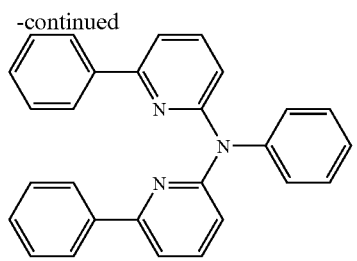

The title compound was prepared according to the method described in a document (Angew. Chem. Int. Ed., 2003, 42, 2051-2053).

In a nitrogen atmosphere, a mixture of π-allylpalladium chloride dimer (3.9 mg), 43 mg of a hexane solution of tri-tert-butylphosphine (10 wt %, equivalent of 4.3 mg of tri-tert-butylphosphine) and o-xylene (10 ml) was stirred at room temperature. Then, sodium tert-butoxide (272 mg), aniline (131 mg) and 2-bromo-6-phenylpyridine (660 mg) obtained by Reference Example 1 were added to the mixture, and stirred at 120° C. for 1 day. After the reaction mixture was allowed to cool, to which was then added water, the mixture was extracted with toluene, the solvent was distilled off, and the residue was purified by silica gel column chromatography, thereby obtaining desired solid (510 mg).

$^1$H-NMR(CDCl$_3$): 7.04(d, J=8.0 Hz, 2H), 7.22-7.48(m, 13H), 7.63(t, J=8.0 Hz, 2H)

EXAMPLE 2

Preparation of a Platinum Complex

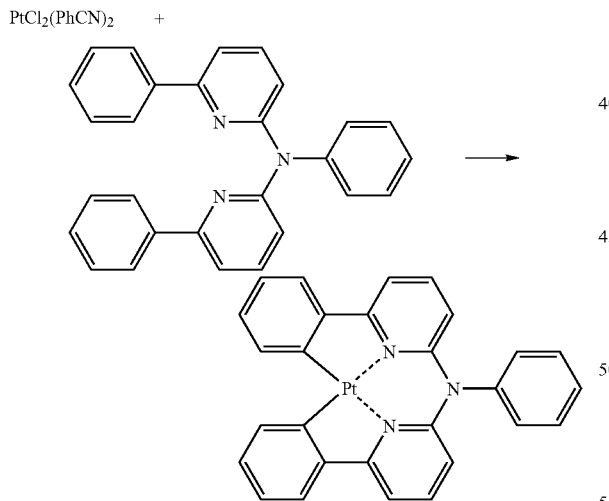

In an argon atmosphere, dichlorobis(benzonitrile)platinum (II) (228 mg), N,N-bis(6-phenylpyridine-2-yl)aniline (193 mg) obtained by Example 1 and 10 ml of o-xylene were stirred at 150° C. for 1 day. After the reaction mixture was allowed to cool, to which was then added water, the mixture was extracted with dichloromethane, the solvent was distilled off, and the residue was purified by silica gel column chromatography, thereby obtaining desired yellow crystal (172 mg).

$^1$H-NMR(CDCl$_3$): 6.43(d, J=8.4 Hz, 2H), 7.18-7.26(m, 2H), 7.39-7.50(m, 4H), 7.57-7.82(m, 9H), 8.24-8.56(m, 2H)

REFERENCE EXAMPLE 2

Preparation of 2-(m-chlorophenyl)pyridine

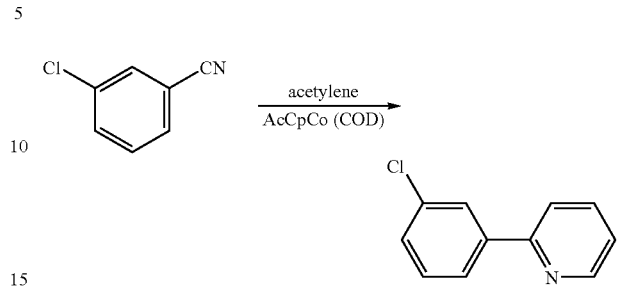

The title compound was prepared according to the method described in a document (J. Am. Chem. Soc., 1991, 113, 8521-8522).

(μ-acetylcyclopentadienyl)(1,5-cyclooctadiene)cobalt (144 mg), m-chlorobenzonitrile (1.80 g) and 10 ml of o-xylene were placed into a 100 ml autoclave, then acetylene was filled in the autoclave, and the reaction was carried out at 150° C. After the reaction mixture was allowed to cool, to which was then added water, the mixture was extracted with toluene, the solvent was distilled off, and the residue was purified by silica gel column chromatography, thereby obtaining desired compound as an oily substance (2.37 g).

$^1$H-NMR(CDCl$_3$): 7.22-7.30(m, 1H), 7.37-7.41(m, 2H), 7.66-7.88(m, 2H), 7.83-7.89(m, 1H), 8.01(t, J=1.4 Hz, 1H), 8.69-8.72(m, 1H)

EXAMPLE 3

Preparation of N,N-bis[(3-(2-pyridyl)phenyl)aniline

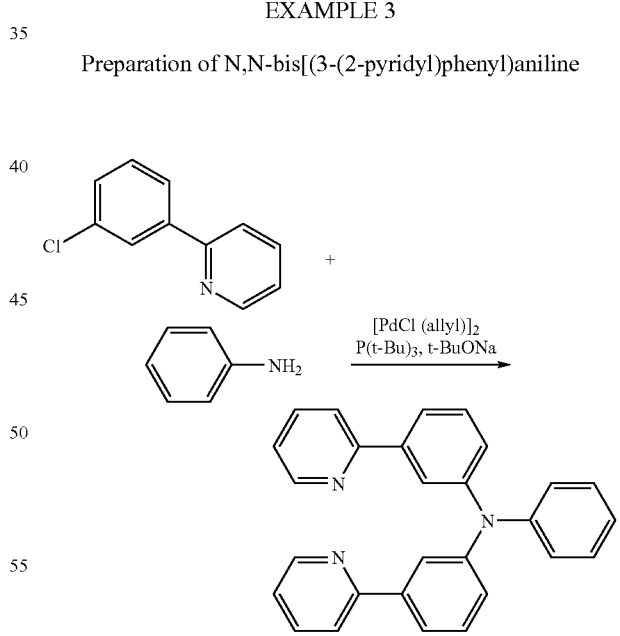

The desired compound was obtained as solid in the same manner as with Example 1, except for changing 2-bromo-6-phenylpyridine (660 mg) with 2-(m-chlorophenyl)pyridine (600 mg) obtained by Reference Example 2, and changing aniline (131 mg) with aniline (140 mg).

$^1$H-NMR(CDCl$_3$)δ: 7.02(tt, J=1.6, 7.2 HZ, 1H), 7.15-7.30 (m, 8H), 7.37(t, J=8.0 Hz, 2H), 7.57-7.76(m, 8H), 8.61-8.65 (m, 2H)

EXAMPLE 4

Preparation of a Platinum Complex

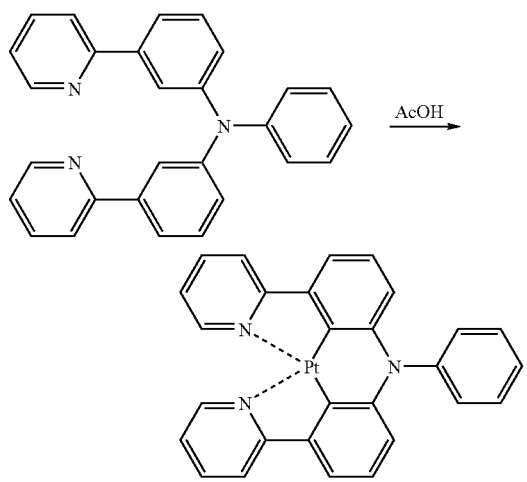

The objective platinum complex was prepared according to the method described in a document (Organometallics, Vol 18, No 17, 3337-3341).

In an argon atmosphere, potassium tetrachloroplatinate (II) (260 mg), N,N-bis(6-phenylpyridine-2-yl)aniline (250 mg) obtained by Example 3 and acetic acid were stirred at 140° C. for 3 days. After the reaction mixture was allowed to cool, to which was then added water, the mixture was extracted with dichloromethane, the solvent was distilled off, and the residue was purified by silica gel column chromatography, thereby obtaining desired compound as reddish crystal (40 mg).

$^1$H-NMR(CDCl$_3$)δ: 6.20-6.45(m, 2H), 7.02(t, J=7.6 Hz, 2H), 7.34-7.65(m, 9H), 7.85-8.01(m, 4H), 8.93-8.97(m, 2H)

EXAMPLE 5

Preparation of N,N-bis(6-phenylpyridine-2-yl)-3,5-di(t-butyl)aniline

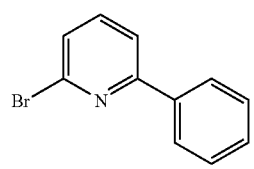

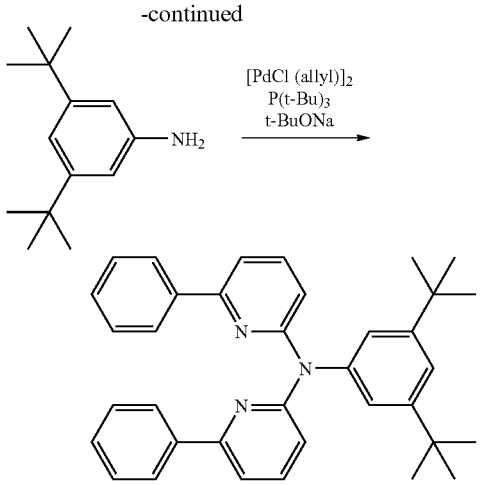

The desired compound was obtained as solid (420 mg) in the same manner as with Example 1, except for changing aniline (131 mg) with 3,5-di(t-butyl)aniline (219 mg), and changing 2-bromo-6-phenyl-pyridine (660 mg) with 2-bromo-6-phenylpyridine (500 mg).

$^1$H-NMR(CDCl$_3$)δ: 1.30(s, 18H), 7.15-7.41(m, 11H), 7.62 (t, J=8.0 Hz, 2H), 7.87-7.92(m, 4H)

EXAMPLE 6

Preparation of a Platinum Complex

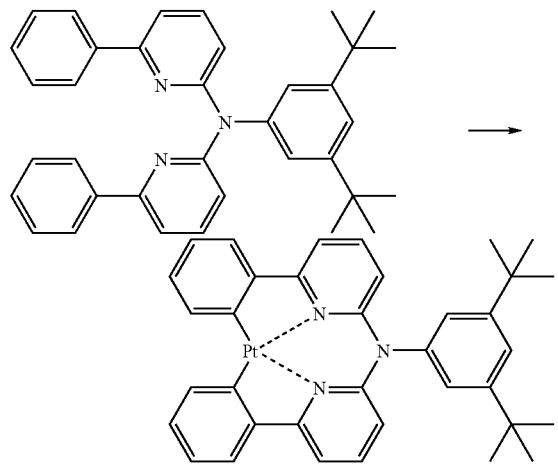

The desired compound was obtained as yellow crystal (451 mg) in the same manner as with Example 2, except for changing N,N-bis(6-phenylpyridine-2-yl)aniline (193 mg) with N,N-bis(6-phenylpyridine-2-yl)-3,5-di(t-butyl)aniline (546 mg) obtained by Example 5, and changing dichloro bis(benzonitrile)platinum (228 mg) with dichloro bis(benzonitrile)platinum (504 mg).

$^1$H-NMR(CDCl$_3$)δ: 1.38(s, 18H), 6.45(d, J=8.1 HZ, 2H), 7.20-7.24(m, 4H), 7.45(m, 2H), 7.66(t, J=1.7 HZ, 1H), 7.70-7.73(m, 2H), 7.80(dd, J=7.7, 1.1 HZ, 2H), 8.32-8.50(m, 2H)

EXAMPLE 7

N,N-bis[3-(2-pyridyl)phenyl]-3,5-di(t-butyl)aniline

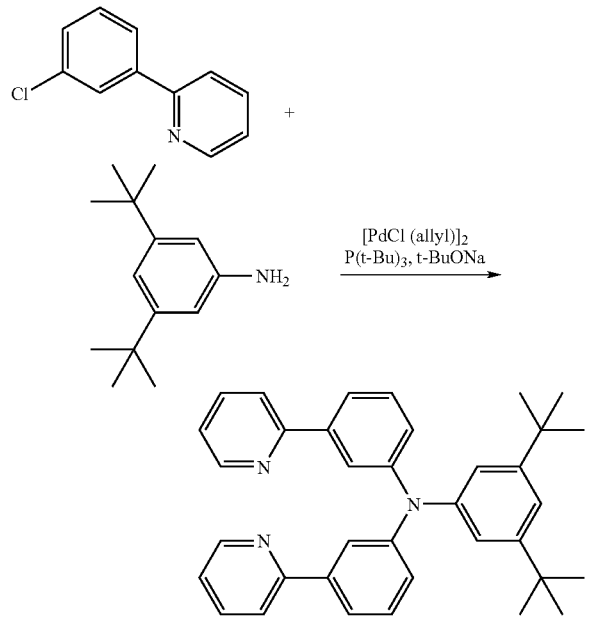

The desired compound was obtained as solid (613 mg) in the same manner as with Example 3, except for changing aniline (140 mg) with 3,5-di(t-butyl)aniline (309 mg).

$^1$H-NMR(CDCl$_3$)δ: 1.24(s, 18H), 7.01-7.26(m, 7H), 7.35 (t, J=8.0 HZ, 2H), 7.56-7.78(m, 8H), 8.62-8.64(m, 2H)

EXAMPLE 8

Preparation of a Platinum Complex

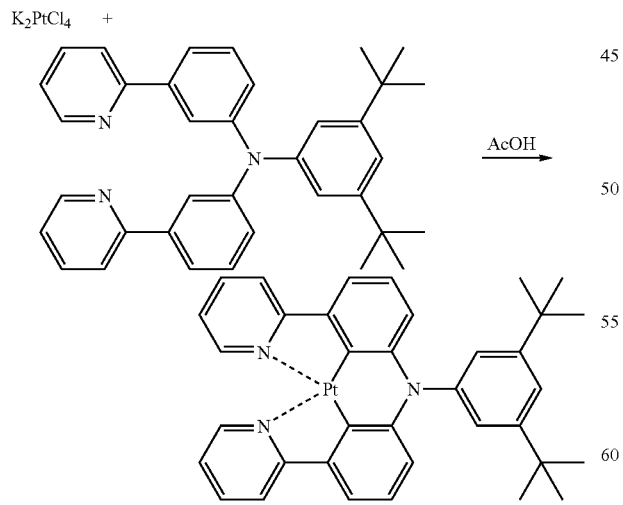

The desired compound was obtained as reddish crystal (124 mg) in the same manner as with Example 4, except for changing N,N-bis[3-(2-pyridyl)phenyl]aniline (250 mg) with N,N-bis[3-(2-pyridyl)phenyl]-3,5-di(t-butyl)aniline (248 mg) obtained by Example 7, and changing potassium tetrachloroplatinate (II) (260 mg) with potassium tetrachloroplatinate (II) (306 mg).

$^1$H-NMR(CDCl$_3$)δ: 1.36(s, 18H), 6.28-6.40(m, 2H), 7.01-7.26(m, 4H), 7.34-7.39(m, 4H), 7.35(t, J=1.8 Hz, 1H), 7.86-8.00(m, 4H), 8.91-9.00(m, 2H)

REFERENCE EXAMPLE 3

Preparation of 6-bromo-2,2'-bipyridine

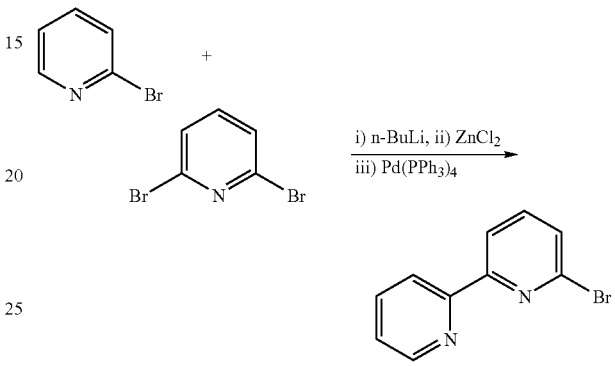

The title compound was prepared according to the method described in a document (Organic Synthesis, Vol. 78, p 53).

In a nitrogen atmosphere, a THF (5 ml) solution of bromopyridine (0.5 g) was cooled to −78° C., then a hexane solution of n-butyllithium (1.57 M, 2 ml) was added dropwise thereto, after dropwise, the mixture was stirred at 0° C. for 3 hours. Thereafter, a THF solution of zinc chloride (3.15 g) was added dropwise to the mixture, after dropwise, the mixture was stirred for 3 hours. Next, 2,6-dibromopyridine (0.75 g) and tetrakis(triphenylphosphine)palladium (146 mg) were added to the mixture at room temperature, and the mixture was refluxed for 1 day. After the reaction mixture was allowed to cool, to which was then added water, the mixture was extracted with toluene, the solvent was distilled off, and the residue was purified by silica gel column chromatography, thereby obtaining desired compound as white crystal (0.5 g).

$^1$H-NMR(CDCl$_3$)δ: 7.26-7.36(m, 1H), 7.49(d, J=7.8 HZ, 1H), 7.67(t, J=7.6 HZ, 1H), 7.82(t, J=7.8 HZ, 1H), 8.36-8.43 (m, 2H), 8.65-8.68(m, 1H)

REFERENCE EXAMPLE 4

Preparation of 2-(3-bromophenyl)pyridine

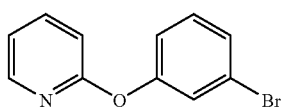

A mixture of 2-bromopyridine (2.5 g, 15.8 mmol), 3-bromophenol (5.5 g, 31.6 mmol) and potassium carbonate (2.2 g, 15.8 mmol) was stirred at 200° C. for 3 hours. After the reaction mixture was allowed to cool, to which was then added an aqueous 1 mol/L sodium hydroxide solution, the mixture was extracted with dichloromethane, the solvent was distilled off, and the residue was purified by silica gel column chromatography and recrystallization, thereby obtaining 2.9 g of desired compound as white crystal.
Yield: 73.2%.

REFERENCE EXAMPLE 5

Preparation of (2-bromo-6-phenylthio)pyridine

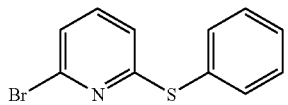

A tetrahydrofuran solution of isopropyl magnesium chloride (11.6 ml, 2.0 M, 23.2 mmol) was added to a tetrahydrofuran (15 ml) solution of 2,6-dibromopyridine (5.0 g, 21.1 mmol), and the mixture was stirred at room temperature for 6 hours. Triethylamine (2.9 ml, 21.1 mmol) and diphenyldisulfide (5.5 g, 25.3 mmol, 1.2 equivalents) was successively added to the mixture, then the mixture was stirred at room temperature for 12 hours. The reaction mixture was poured into an aqueous saturated ammonium chloride solution, the mixture was extracted with diethylether, the solvent of organic layer was distilled off, and the residue was purified by silica gel column chromatography, thereby obtaining 2.8 g of (2-bromo-6-phenylthiopyridine) as brown oil. Yield: 49.9%.

$^1$H-NMR(CDCl$_3$)δ: 6.71(dd, J=1.0, 7.6 Hz, 1H), 7.16(dd, J=0.8, 7.6 Hz, 1H), 7.27(t, J=7.7 Hz, 1H), 7.38-7.51(m, 3H), 7.54-7.66(m, 2H)

REFERENCE EXAMPLE 6

Preparation of 2-bromo-6-phenylpyridine

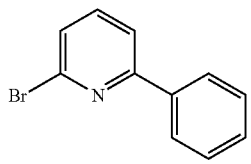

A hexane (70 ml) solution of N,N-dimethylaminoethanol (12.0 ml, 118.5 mmol) was dropwise added to a hexane solution of n-butyllithium (150 ml, 1.58 M, 237.0 mmol) at 5° C. while 30 minutes. Next, a hexane (10 ml) solution of 2-phenylpyridine (8.5 ml, 59.3 mmol) was dropwise added to the mixture at 5° C. while 20 minutes. A hexane solution of 2-lithio-6-phenylpyridine was prepared by the mixture stirred at 5° C. for 1 hour additionally.

A tetrahydrofuran (200 ml) solution of 1,2-dibromo-1,1,2, 2-tetrafluoroethane (17.6 ml, 148.3 mmol) was cooled to −78° C., then the hexane solution of 2-lithio-6-phenylpyridine was prepared as above was dropwise added thereto while 30 minutes. This reaction mixture was stirred at −78° C. for 1 hour, then the mixture was poured into an aqueous ammonium chloride solution, an organic layer was separated, furthermore an aqueous layer was extracted with hexane. The organic layer was combined, and the solvent was distilled off, and the residue was purified by silica gel column chromatography and recrystallization, thereby obtaining 12.0 g of 2-bromo-6-phenylpyridine as white crystal. Yield: 86.4%.

$^1$H-NMR(CDCl$_3$)δ: 7.38-7.53(m, 4H), 7.60(t, J=7.6 HZ, 1H), 7.69(dd, J=1.0, 7.6 HZ, 1H), 7.95-8.04(m, 2H)

REFERENCE EXAMPLE 7

Preparation of 2-hydroxy-6-phenylpyridine

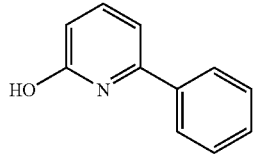

An ether (30 ml) solution of phenyl magnesium bromide ether solution (12.3 ml, 3.0 M, 37.0 mmol) was dropwise added to a mixture of 2-chloro-6-methoxypyridine (4.4 ml, 37.0 mmol), 1,3-bis(diphenylphosphino)propane nickel (II) chloride (228 mg) and diethyl ether (40 ml) at room temperature while 30 minutes. Thereafter, this reaction mixture was stirred under reflux for 1 hour, then the mixture was poured into an aqueous ammonium chloride solution, an organic layer was separated, furthermore an aqueous layer was extracted with dichloromethane. The organic layer was combined, and the solvent was distilled off, and the residue was filtered through a silica gel, thereby obtaining 7.0 g of crude 2-methoxy-6-phenylpyridine as pale yellow oil.

A hydrochloric acid (30.8 ml, 370.0 mmol) was added to pyridine (30.0 ml, 370.0 mmol), and the mixture was heated with removing water till an internal reaction temperature reach to 180° C. After the reaction mixture was cooled to 120° C., 2-methoxy-6-phenylpyridine (7.0 g) obtained as above was added to the reaction mixture and stirred at 180° C. for 1 hour. After the reaction mixture was allowed to cool, to which was then added an aqueous 1 mol/L sodium hydroxide solution, the mixture was extracted with dichloromethane, the solvent was distilled off, and the residue was purified by recrystallization, thereby obtaining 5.2 g of 2-hydroxy-6-phenylpyridine as white crystal. Yield: 82.1%.

$^1$H-NMR(CDCl$_3$)δ: 6.50(dd, J=1.0, 8.0 HZ, 1H), 6.54(dd, J=1.0, 8.0 HZ, 1H), 7.42-7.58(m, 4H), 7.64-7.75(m, 2H), 11.72(brs, 1H)

REFERENCE EXAMPLE 8

Preparation of 2-(3-hydroxyphenyl)pyridine

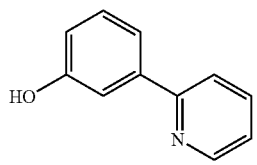

A tetrahydrofuran solution of 3-methoxyphenyl magnesium bromide (52.4 ml, 1.0 M, 52.4 mmol) was dropwise added to a mixture of 2-bromopyridine (5.0 ml, 52.4 mmol), 1,3-bis(diphenylphosphino)propane nickel (II) chloride (284 mg) and diethyl ether (100 ml) at room temperature while 1 hour. Thereafter, this reaction mixture was poured into an aqueous ammonium chloride solution, the mixture was extracted with toluene, the solvent was distilled off, and the residue was purified by silica gel column chromatography, thereby obtaining 9.4 g of 2-(3-methoxyphenyl)pyridine as colorless oil.

A hydrochloric acid (43.7 ml, 524.0 mmol) was added to pyridine (42.4 ml, 524.0 mmol), and the mixture was heated with removing water till an internal reaction temperature reach to 180° C. After the reaction mixture was cooled to 120° C., 2-(3-methoxyphenyl)pyridine (9.4 g) obtained as above was added to the reaction mixture and stirred at 180° C. for 3 hours. After the reaction mixture was cooled, to which was then added an aqueous 1 mol/L sodium hydroxide solution, the mixture was extracted with dichloromethane, the solvent was distilled off, and the residue was purified by recrystallization, thereby obtaining 6.9 g of 2-(3-hydroxyphenyl)pyridine as white powder. Yield: 76.9%.

$^1$H-NMR(CDCl$_3$)δ: 2.20(brs, 1H), 6.81(ddd, J=1.2, 2.6, 7.8 HZ, 1H), 7.14-7.36(m, 2H), 7.33(dt, J=7.6, 1.6 HZ, 1H), 7.49(t, J=2.0 HZ, 1H), 7.70(dt, J=1.8, 8.2 HZ, 1H), 8.59(ddd, J=0.8, 1.6, 5.0 HZ, 1H)

EXAMPLE 9

Preparation of 2-Phenyl-6-[3-2-pyridyloxy]phenyl]pyridine

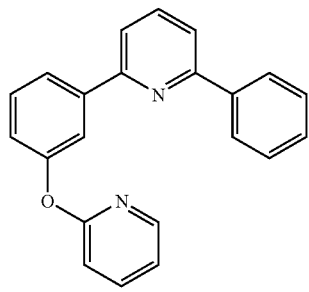

A THF (30 ml) solution of 2-(3-bromophenyl)pyridine (1.0 g, 4.0 mmol) was cooled to −78° C., then a hexane solution of n-butyllithium (2.8 ml, 1.58 M, 4.4 mmol) was added dropwise thereto while 5 minutes. The reaction mixture was stirred for 1 hour at −78° C. Thereafter, a THF solution of zinc chloride (9.2 ml, 0.52 M, 4.8 ml) was added dropwise to the mixture at −78° C. while 20 minutes, after dropwise, the temperature of the reaction mixture was allowed to warm to room temperature while 30 minutes. Next, tetrakis(triphenylphosphine)palladium (46 mg) and 2-bromo-6-phenylpyridine (936 mg, 4.0 mmol) were added to the mixture, and the mixture was refluxed for 18 hours. After the reaction mixture was allowed to cool, then the mixture was poured into a mixture of ethylenediaminetetraacetic acid (1.4 g, 4.8 mmol)/water (30 ml)/an aqueous saturated sodium hydrogen carbonate solution (35 ml), an organic layer was separated, furthermore an aqueous layer was extracted with dichloromethane. The organic layer was combined, and the solvent was distilled off, and the residue was purified by silica gel column chromatography, thereby obtaining 1.0 g of 2-Phenyl-6-[3-2-pyridyloxy]phenyl]pyridine as pale yellow viscous liquid.

Yield: 77.1%

$^1$H-NMR(CDCl$_3$)δ: 6.92-7.06(m, 2H), 7.16-7.26(m, 1H), 7.36-7.58(m, 4H), 7.64-7.86(m, 4H), 7.94-8.04(m, 2H), 8.08-8.18(m, 2H), 8.23(ddd, J=0.6, 2.0, 5.0 HZ, 1H)

EXAMPLE 10

Preparation of 2,2'-oxybis(6-phenylpyridine)

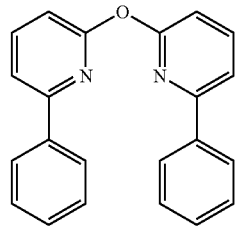

A mixture of 2-hydroxy-6-phenylpyridine (1.0 g, 5.8 mmol), 2-bromo-6-phenylpyridine (1.4 g, 5.8 mmol) and potassium carbonate (807 mg, 5.8 mmol) was stirred at 200° C. for 8 hours. After the reaction mixture was cooled, to which was then added an aqueous 1 mol/L sodium hydroxide solution, the mixture was extracted with dichloromethane, the solvent was distilled off, and the residue was purified by silica gel column chromatography, thereby obtaining 1.3 g of 2,2'-oxybis(6-phenylpyridine) as colorless crystal.

Yield: 68.6%.

$^1$H-NMR(CDCl$_3$)δ: 7.07(d, J=8.0 Hz, 2H), 7.30-7.46(m, 6H), 7.56(d, J=8.0 HZ, 2H), 7.80(t, J=8.0 HZ, 2H), 7.88-8.00 (m, 4H)

EXAMPLE 11

Preparation of 2-phenyl-6-(3-pyridylphenoxy)pyridine

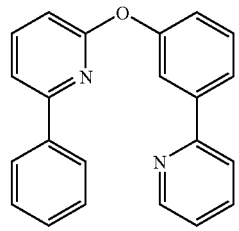

A mixture of 2-(3-hydroxyphenyl)pyridine (1.0 g, 5.8 mmol), 2-bromo-6-phenylpyridine (1.3 g, 5.6 mmol) and potassium carbonate (576 mg, 4.2 mmol) was stirred at 200° C. for 8 hours. After the reaction mixture was cooled, to which was then added an aqueous 1 mol/L sodium hydroxide solution, the mixture was extracted with dichloromethane, the solvent was distilled off, and the residue was purified by silica gel column chromatography, thereby obtaining 1.3 g of 2-phenyl-6-(3-pyridylphenoxy)pyridine as white solid.

Yield: 72.1%.

$^1$H-NMR(CDCl$_3$)δ: 6.83(dd, J=0.8, 8.0 HZ, 1H), 7.16-7.45(m, 5H), 7.45-7.58(m, 2H), 7.66-7.80(m, 3H), 7.84(m, 4H), 8.69(dt, J=4.6 HZ, 1H)

EXAMPLE 12

Preparation of [2,2'-oxybis(6-phenylpyridinato)-C,N,N,C]platinum

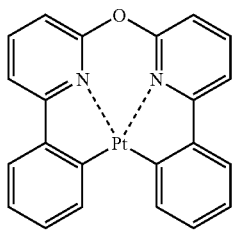

A mixture of dichlorobis(benzonitrile)platinum (II) (100 mg, 0.212 mmol), 2,2'-oxybis(6-phenylpyridine) (69 mg, 0.212 mmol) obtained by Example 10 and o-xylene (20 ml) was stirred under reflux for 3 hours. After the reaction mixture was allowed to cool, the reaction mixture was filtered and the residue was purified by silica gel column chromatography and recrystallization, thereby obtaining 77 mg of [2,2'-oxybis (6-phenylpyridinato)-C,N,N,C]platinum as yellow powder. Yield: 70.2%.

$^1$H-NMR(CD$_2$Cl$_2$)δ: 7.23(ddd, J=1.2, 7.2, 7.8 HZ, 2H), 7.37(dd, J=0.9, 8.2 HZ, 2H), 7.42(ddd, J=1.4, 7.2, 7.6 HZ, 2H), 7.78(dd, J=0.9, 7.8 HZ, 2H), 7.82(dd, 1.4, 7.8 HZ, 2H), 8.13(dd, 7.8, 8.2 HZ, 2H), 8.31(ddd, J=1.2, 7.6, 25.0(H—Pt), 2H)

REFERENCE EXAMPLE 9

Preparation of 6-phenyl-2,2'-bipyridine

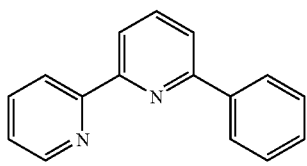

A solution of phenyllithium.cyclohexane/diethyl ether (40.9 ml, 38.4 mmol) was dropwise added to a mixture of 2,2'-bipyridine (5.0 g, 32.0 mmol) and diethyl ether (50 ml) at 5° C. while 15 minutes. This reaction mixture was stirred at room temperature for 2 hours, then the mixture was poured into water, an organic layer was separated from the mixture, furthermore an aqueous layer was extracted with dichloromethane. The organic layer was combined, and the solvent was distilled off, and the residue was diluted with acetone (50 ml), then saturated potassium permanganate acetone solution (120 ml) was added thereto, the mixture was stirred at room temperature for 1 hour. The obtained reaction mixture was filtered by Celite, the solvent of the filtrate was distilled off, and the residue was purified by silica gel column chromatography and recrystallization, thereby obtaining 4.2 g of 6-phenyl-2,2'-bipyridine as white crystal. Yield: 55.4%.

$^1$H-NMR(CDCl$_3$)δ: 7.33(ddd, J=1.4, 4.8, 7.6 HZ, 1H), 7.38-7.58(m, 3H), 7.74-7.96(m, 3H), 8.10-8.22(m, 2H), 8.38 (dd, J=1.0, 7.6 HZ, 1H), 8.61-8.74(m, 2H)

EXAMPLE 13

Preparation of 6-(2-methoxyphenyl)-6'-phenyl-2,2'-bipyridine

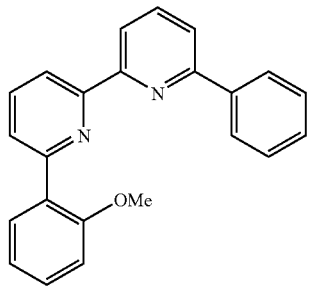

A diethyl ether (25 ml) solution of 2-bromoanisole (5.6 ml, 45.2 mmol) was dropwise added to a mixture of lithium (660 mg, 94.9 mmol) and diethyl ether (25 ml) at room temperature while 30 minutes. An ether solution of 2-methoxyphenyllithium was prepared by heating this reaction mixture under reflux for 1 hour.

A diethyl ether (40 ml) solution of 6-phenyl-2,2'-bipyridine (7.0 g, 30.1 mmol) obtained by Reference Example 9 was cooled to 5° C., and the ether solution of 2-methoxyphenyllithium prepared as above was dropwise added to thereto while 20 minutes. This reaction mixture was stirred for 18 hours at room temperature, then the mixture was poured into an aqueous saturated ammonium chloride solution, an organic layer was separated, furthermore an aqueous layer was extracted with dichloromethane. The organic layer was combined, and the solvent was distilled off, then saturated potassium permanganate acetone solution (400 ml) was added to the residue, the mixture was stirred for 30 minutes at room temperature. The obtained reaction mixture was filtered, the solvent of the filtrate was distilled off, and the residue was purified by silica gel column chromatography and recrystallization, thereby obtaining 3.1 g of 6-(2-methoxyphenyl)-6'-phenyl-2,2'-bipyridine as pale yellow crystal. Yield: 30.4%.

$^1$H-NMR(CDCl$_3$)δ: 3.90(s, 3H), 7.04(d, J=8.2HX, 1H), 7.14(dt, J=1.2, 7.6 HZ, 1H), 7.34-7.58(m, 4H), 7.72-8.00(m, 4H), 8.04(dd, J=1.8, 7.4 HZ, 1H), 8.12-8.22(m, 2H), 8.50-8.62(m, 2H)

EXAMPLE 14

Preparation of 2-(6'-phenyl-2,2'-bipyridine-6-yl)phenol

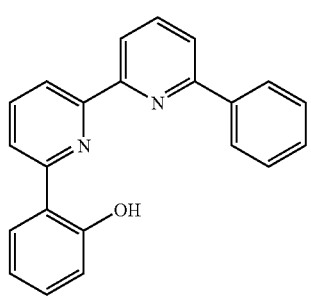

Hydrochloric acid (14.8 ml, 177.2 mmol) was added to pyridine (14.3 ml, 177.2 mmol), and the mixture was heated with removing water till an internal reaction temperature reach to 180° C. After the reaction mixture was cooled to 120° C., 6-(2-methoxyphenyl)-6'-phenyl-2,2'-bipyridine (3.0 g, 8.9 mmol) obtained by Example 13 was added to the reaction mixture and stirred for at 180° C. for 2 hours. After the reaction mixture was cooled, to which was then added an aqueous 1 mol/L sodium hydroxide solution, the mixture was extracted with dichloromethane, the solvent was distilled off, and the residue was purified by silica gel column chromatography and recrystallization, thereby obtaining 2.7 g of 2-(6'-phenyl-2,2'-bipyridine-6-yl)phenol as yellow crystal. Yield: 93.9%.

$^1$H-NMR(CDCl$_3$)δ: 6.97(ddd, J=1.4, 7.2, 8.4 HZ, 1H), 7.09(dd, J=1.4, 8.4 HZ, 1H), 7.36(ddd, J=1.6, 7.4, 8.4 Hz, 1H), 7.42-7.60(m, 3H), 7.78-8.08(m, 5H), 8.10-8.22(m, 3H), 8.53(dd, J=1.8, 7.0 HZ, 1H), 14.29(s, 1H)

EXAMPLE 15

Preparation of 6-(2-acetoxyphenyl)-6'-phenyl-2,2'-bipyridine

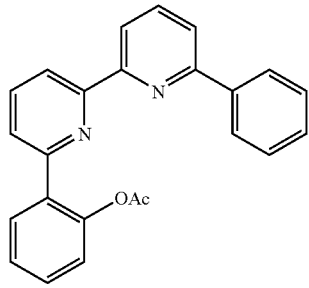

Acetic anhydride (580 μL, 6.2 mmol) was dropwise added to a pyridine (20 ml) solution of 2-(6'-phenyl-2,2'-bipyridine-6-yl)phenol (1.0 g, 3.1 mmol) obtained by Example 14, then the mixture was stirred for 24 hours at room temperature. The solvent was distilled off from the reaction mixture, and the residue was purified by silica gel column chromatography and recrystallization, thereby obtaining 1.05 g of 6-(2-acetoxyphenyl)-6'-phenyl-2,2'-bipyridine as yellow crystal. Yield: 93.0%.

$^1$H-NMR(CDCl$_3$)δ: 2.11(s, 3H), 7.21(dd, J=2.0, 7.6 HZ, 1H), 7.34-7.62(m, 6H), 7.74-7.98(m, 4H), 8.12-8.24(m, 2H), 8.47(dd, J=1.0, 7.6 HZ, 1H), 8.64(dd, J=1.0, 7.9 HZ, 1H)

EXAMPLE 16

Preparation of [2-(6'-phenyl-2,2'-bipyridine-6-yl)phenolato-C,N,N,O]platinum

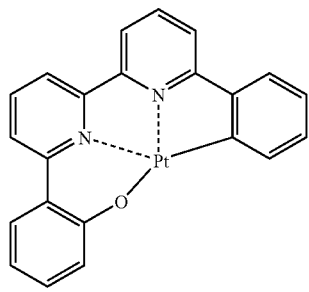

A mixture of [(1,2,5,6-η$^4$)-1,5-hexadienyl]dichloroplatinum (100 mg, 0.287 mmol), 6-(2-acetoxyphenyl)-6'-phenyl-2,2'-bipyridine (116 mg, 0.316 mmol) obtained by Example 15 and 2-ethoxyethanol (5 ml) was stirred under reflux for 3 hours. After the reaction mixture was allowed to cool, potassium hydroxide (24 mg, 0.431 mmol) was added to the reaction mixture, then the mixture was stirred under reflux for 3 hours. The solvent was distilled off from the reaction mixture, and the residue was purified by silica gel column chromatography and recrystallization, thereby obtaining 67 mg of [2-(6'-phenyl-2,2'-bipyridine-6-yl)phenolato-C,N,N,O]platinum as orange crystal. Yield: 45.1%.

REFERENCE EXAMPLE 10

Preparation of 2-methyl-6-phenylpyridine

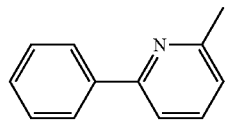

A diethyl ether (40 ml) solution of phenyl magnesium bromide diethyl ether solution (21.3 ml, 3.0 M, 63.9 mmol) was dropwise added to a mixture of 2-bromo-6-methylpyridine (10.0 g, 58.1 mmol), 1,3-bis(diphenylphosphino)propane nickel (II) chloride (315 mg 1.0 mol %) and diethyl ether (100 ml) while 30 minutes at room temperature, and this reaction mixture was stirred under reflux for 2 hours. Then the mixture was poured into an aqueous saturated ammonium chloride solution, an organic layer was separated, furthermore an aqueous layer was extracted with dichloromethane. The organic layer was combined, and the solvent was distilled off, and the residue was purified by silica gel column chromatography, thereby obtaining 8.6 g of 2-methyl-6-phenylpyridine as pale yellow oil. Yield: 87.5%.

$^1$H-NMR(CDCl$_3$)δ: 2.64(s, 3H), 7.10(d, 7.2 HZ, 1H), 7.36-7.56(m, 4H), 7.63(t, J=7.7 Hz, 1H), 7.96-8.04(m, 2H)

EXAMPLE 17

Preparation of 1,2-bis(6-phenylpyridine-2-yl)ethane

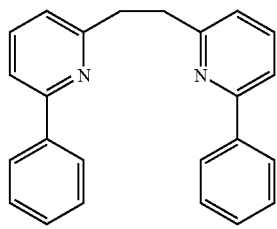

A tetrahydrofuran (8 ml) solution of diisopropylamine (1.0 ml, 7.1 mmol) was cooled to 5° C., then n-butyllithium hexane solution (4.1 ml, 1.58 M, 6.5 mmol) was dropwise added thereto while 10 minutes, thus lithium diisopropylamide tetrahydrofuran solution was obtained.

The tetrahydrofuran (12 ml) solution of 2-methyl-6-phenylpyridine (1.0 g, 5.9 mmol) obtained by Reference Example 10 was cooled to −78° C., then lithium diisopropylamide tetrahydrofuran solution obtained as above was dropwise added thereto while 15 minutes. The reaction mixture was additionally stirred at −78° C. for 1 hour, then a tetrahydrofuran (10 ml) solution of 1,2-dibromoethane (510 μL, 5.9 mmol, 1 equivalent) was dropwise added thereto, the reaction temperature was allowed to warm to 0° C. while 40 minutes. Then the reaction mixture was poured into an aqueous saturated ammonium chloride solution, an organic layer was separated, furthermore an aqueous layer was extracted with toluene. The organic layer was combined, and the solvent was distilled off, and the residue was purified by silica gel column chromatography and recrystallization, thereby obtaining 646 mg of 1,2-bis(6-phenylpyridine-2-yl)ethane as white powder. Yield: 65.1%.

$^1$H-NMR(CDCl$_3$)δ: 3.41(s, 4H), 7.11(dd, J=1.2, 7.2 HZ, 2H), 7.34-7.68(m, 10H), 7.98-8.08(m, 4H)

EXAMPLE 18

Preparation of [1,2-bis(6-phenylpyridinato-2-yl)ethane-C,N,N,C]platinum

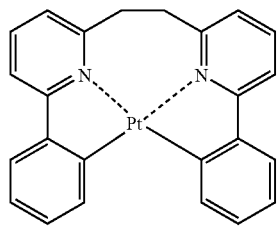

A mixture of dichlorobis(benzonitrile)platinum (280 mg, 0.594 mmol), 1,2-bis(6-phenylpyridine-2-yl)ethane (200 mg, 0.594 mmol) obtained by Example 17 and xylene (60 ml) was stirred under reflux for 8 hours. After the reaction mixture was allowed to cool, the solvent was didtilled off from the reaction mixture, and the residue was purified by silica gel column chromatography and recrystallization, thereby obtaining 186 mg of [1,2-bis(6-phenylpyridinato-2-yl)ethane-C,N,N,C]platinum as yellow powder. Yield: 59.1%.

$^1$H-NMR(CD$_2$Cl$_2$)δ: 3.36(s, 4H), 7.06(dd, J=1.4, 7.2 Hz, 2H), 7.11(dt, J=1.2, 7.6 Hz, 2H), 7.18(dt, J=1.4, 7.6 Hz, 2H), 7.55(dd, J=1.4, 7.6 Hz, 2H), 7.69(dd, J=1.4, 8.0 Hz, 2H), 7.74(dd, J=7.2, 8.0 Hz, 2H), 7.87(ddd, J=1.2, 7.6, 27.1($J^{H-Pt}$), 2H)

REFERENCE EXAMPLE 11

Preparation of 2-formyl-6-phenylpyridine

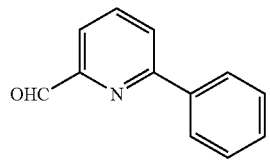

A hexane (150 ml) solution of N,N-dimethylaminoethanol (21.0 ml, 210.0 mmol) was dropwise added to a hexane solution of n-butyllithium (266 ml, 1.58 M, 420.0 mmol) at 5° C. while 1 hour. Next, a hexane (15 ml) solution of 2-phenylpyridine (15.0 ml, 105.0 mmol) was dropwise added to the mixture at 5° C. while 20 minutes. A hexane solution of 2-lithio-6-phenylpyridine was prepared by the mixture stirred at 5° C. for 1 hour additionally.

A tetrahydrofuran (400 ml) solution of N,N-dimethylformamide (20.0 ml, 262.5 mmol) was cooled to −78° C., then the hexane solution of 2-lithio-6-phenylpyridine was prepared as above was dropwise added thereto while 40 minutes. This reaction mixture was stirred at −78° C. for 1 hour, then the mixture was poured into an aqueous 1 mol/L hydrochloric acid, an organic layer was separated, furthermore an aqueous layer was extracted with dichloromethane. The organic layer was combined, the solvent was distilled off, and the residue was purified by silica gel column chromatography and distillation, thereby obtaining 17.1 g of 2-formyl-6-phenylpyridine as pale yellow oil. Yield: 88.9%.

$^1$H-NMR(CDCl$_3$)δ: 7.42-7.58(m, 3H), 7.88-8.00(m, 3H), 8.05-8.14(m, 2H), 10.18(s, 1H)

EXAMPLE 19

Preparation of 1,1-bis(6-phenylpyridine-2-yl)methanol

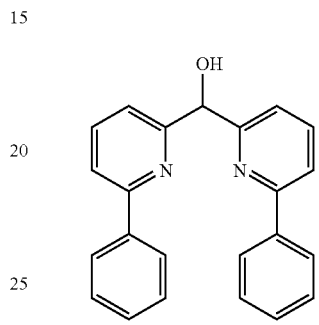

A tetrahydrofuran (20 ml) solution of 2-bromo-6-phenylpyridine (1.3 g, 5.5 mmol) was cooled to −78° C., then a hexane solution of n-butyllithium (3.5 ml, 1.58 M, 5.6 mmol) was dropwise added thereto while 20 minutes. The reaction mixture was additionally stirred at −78° C. for 1 hour, then a tetrahydrofuran (5 ml) solution of 2-formyl-6-phenylpyridine (1.0 g, 5.5 mmol) obtained by Reference Example 11 was dropwise added thereto while 10 minutes, the reaction temperature was allowed to warm to 0° C. while 30 minutes. Then the reaction mixture was poured into an aqueous ammonium chloride-saturated solution, an organic layer was separated, furthermore an aqueous layer was extracted with toluene. The organic layer was combined, and the solvent was distilled off, and the residue was purified by silica gel column chromatography and recrystallization, thereby obtaining 1.1 g of 1,1-bis(6-phenylpyridine-2-yl)methanol as white powder. Yield: 61.2%.

$^1$H-NMR(CDCl$_3$)δ: 6.05(d, J=4.6 Hz, 1H), 6.22(d, J=4.6 Hz, 1H), 7.40-7.80(m, 12H), 8.02-8.12(m, 4H)

EXAMPLE 20

Preparation of 2,2'-carbonylbis(6-phenylpyridine)

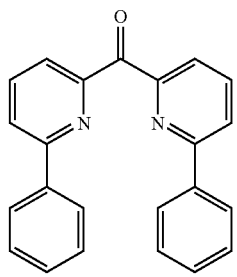

Manganese (IV) oxide (2.8 g, purity 90%, 29.5 mmol) was added to a dichloromethane (20 ml) solution of 1,1-bis(6- phenylpyridine-2-yl)methanol (1.0 g, 3.0 mmol) obtained by Example 19, and this reaction mixture was stirred for 1 hour at room temperature. The obtained reaction mixture was filtered by silica gel, the solvent of the filtrate was distilled off, and the residue was purified by recrystallization, thereby obtaining 920 mg of 2,2'-carbonylbis(6-phenylpyridine) as white powder. Yield: 92.7%.

$^1$H-NMR(CDCl$_3$)δ: 7.38-7.48(m, 6H), 7.94-8.14(m, 10H)

EXAMPLE 21

Preparation of [2,2'-carbonylbis(6-phenylpyridinato)-C,N,N,C]platinum

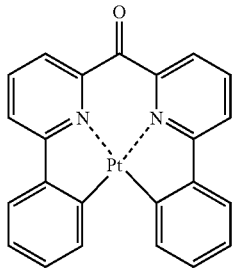

A mixture of dichlorobis(benzonitrile)platinum (140 mg, 0.297 mmol), 2,2'-carbonylbis(6-phenylpyridine) (100 mg, 0.297 mmol) obtained by Example 20 and xylene (30 ml) was stirred under reflux for 10 hours. After the reaction mixture was allowed to cool, the reaction mixture was filtered, and the residue was purified by silica gel column chromatography and recrystallization, thereby obtaining 120 mg of [2,2'-carbonylbis(6-phenylpyridinato)-C,N,N,C]platinum as reddish powder. Yield: 76.3%.

EXAMPLE 22

Preparation of 1,1'-bis(6-phenylpyridine-2-yl)ethylene

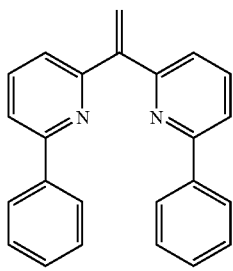

A tetrahydrofuran (8 ml) solution of methyltriphenylphosphonium bromide (584 mg, 1.6 mmol) was cooled to 5° C., then potassium t-butoxide was added thereto, and the mixture was stirred for 1 hour. Thereafter, a tetrahydrofuran (8 ml) solution of 2,2'-carbonylbis(6-phenylpyridine) (500 mg, 1.5 mmol) was dropwise added thereto, and the mixture was stirred for 12 hours at room temperature. Then the reaction mixture was dropwise added to an aqueous saturated ammonium chloride solution, an organic layer was separated, furthermore an aqueous layer was extracted with toluene. The organic layer was combined, and the solvent was distilled off, and the residue was purified by silica gel column chromatography and recrystallization, thereby obtaining 445 mg of 1,1'-bis(6-phenylpyridine-2-yl)ethylene as white powder. Yield: 89.3%.

$^1$H-NMR(CDCl$_3$)δ: 6.31(s, 2H), 7.36-7.52(m, 8H), 7.68-7.80(m, 4H), 8.04-8.12(m, 4H)

EXAMPLE 23

Preparation of N,N-bis[3-(2-pyridyl)phenyl]mesitylamine

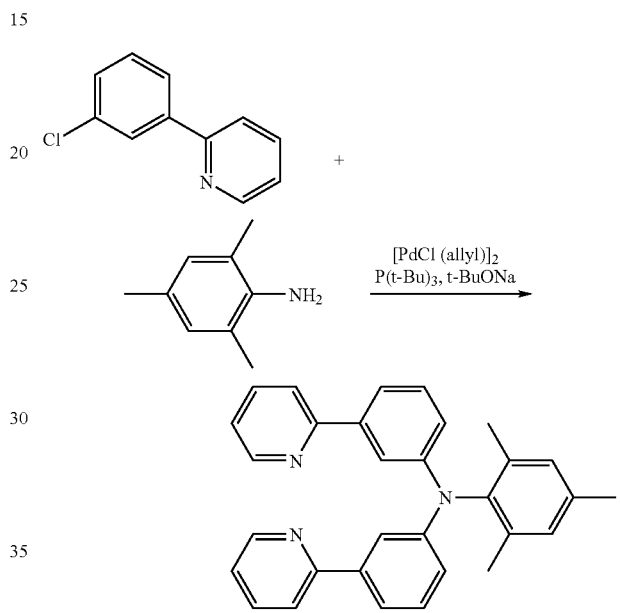

942 mg of the title compound was obtained in a similar manner to Example 1 from 509 mg of mesitylaniline with 1.5 g of 2-(3-chlorophenyl)pyridine.

$^1$H-NMR(CDCl$_3$)δ: 2.07(s, 6H), 2.36(s, 3H), 6.91-7.38(m, 8H), 7.51-7.80(m, 8H), 8.60-8.68(m, 2H)

EXAMPLE 24

Preparation of N,N-bis(6-phenylpyridine-2-yl)-1-pyrenylamine

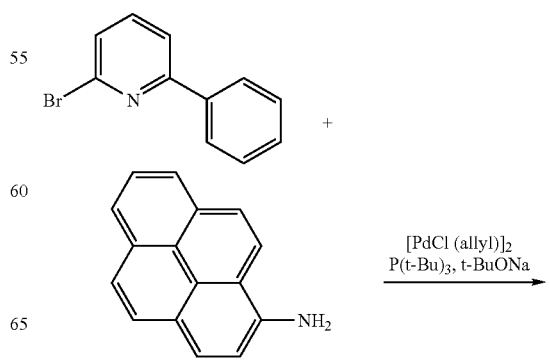

-continued

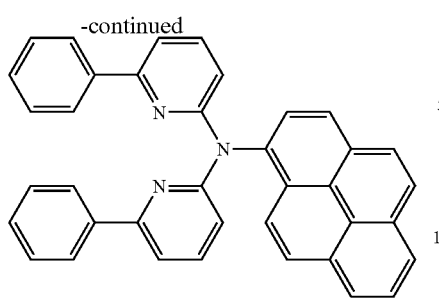

905 mg of the title compound was obtained in a similar manner to Example 1 from 400 mg of 1-aminopyrene with 906 mg of 2-bromo-6-phenylpyridine.

$^{1}$H-NMR(CDCl$_{3}$)δ: 7.02(d, J=8.2 Hz, 2H), 7.20-7.32(m, 6H), 7.38(d, J=7.2 Hz, 2H), 7.58(t, J=8.0 Hz, 2H), 7.74-7.85 (m, 3H), 7.93-8.31(m, 10H)

EXAMPLE 25

Preparation of a Platinum Complex

PtCl$_{2}$(PhCN) +

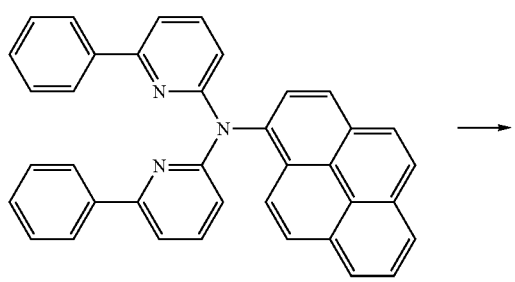

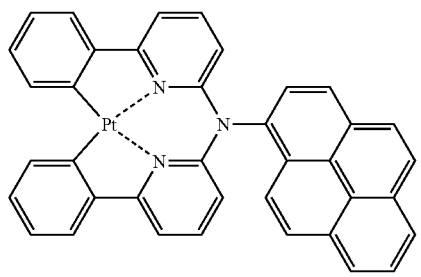

190 mg of the target platinum complex was obtained as yellow crystal in a similar manner to Example 12 from 180 mg of dichlorobis(benzonitrile)platinum with 200 mg of N,N-bis(6-phenylpyridine-2-yl)-1-pyrenylamine.

$^{1}$H-NMR(CD$_{2}$Cl$_{2}$)δ: 6.24-6.38(m, 2H), 7.16-7.27(m, 2H), 7.45(t, J=7.0 HZ, 2H), 7.51-7.66(m, 4H), 7.82-7.89(m, 3H), 8.05-8.51(m, 10H)

EXAMPLE 26

Preparation of a Platinum Complex

PtCl$_{2}$ +

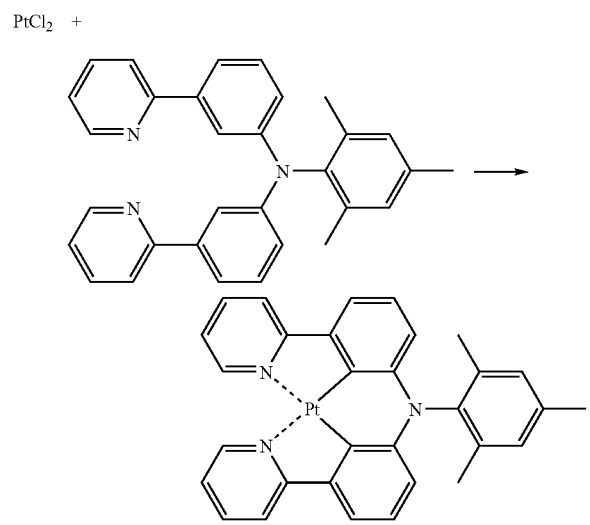

A mixture of N,N-bis[3-(2-pyridyl)phenyl]mesitylamine (471 mg), platinum chloride (II) (284 mg) and benzonitrile was stirred under reflux for 5 hours. After the reaction mixture was allowed to cool, benzonitrile of the reaction mixture was distilled off, water was added to the residue, and the mixture was extracted with dichloromethane. Methylenedichloride of the organic layer was distilled off, and the residue was purified by silica gel column chromatography, thereby obtaining target platinum complex as reddish crystal (328 mg).

$^{1}$H-NMR(CDCl$_{3}$)δ: 1.84(s, 6H), 2.42(m, 3H), 6.17-6.27 (m, 2H), 6.99-7.03(m, 2H), 7.12(s, 2H), 7.36-7.43(m, 4H), 7.90-8.01(m, 4H), 8.95-8.97(m, 2H)

EXAMPLE 27

Preparation of N,N-bis[3-(2-pyridyl)phenyl]4-(9H-carbazole-9-yl)aniline

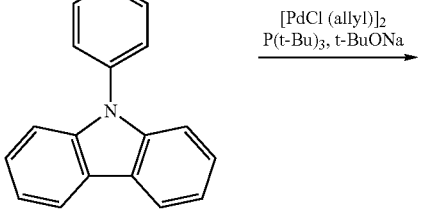

-continued

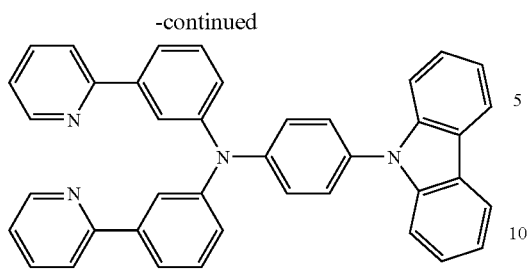

661 mg of the title compound was obtained as glassy solid in a similar manner to Example 1 from 360 mg of p-(9H-carbazole-9-yl)aniline with 555 mg of 2-(3-chlorophenyl)pyridine.

EXAMPLE 28

Preparation of a Platinum Complex

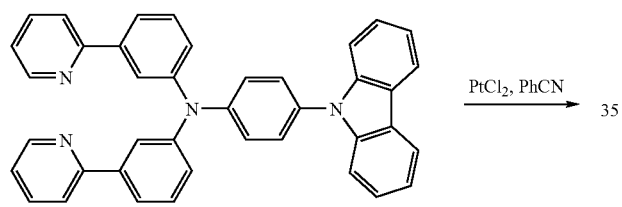

262 mg of the target platinum complex was obtained as reddish crystal in a similar manner to Example 26 from 169 mg of platinum chloride (II) with 400 mg of N,N-bis[3-(2-pyridyl)phenyl]4-(9H-carbazole-9-yl)aniline.

$^1$H-NMR(CD$_2$Cl$_2$)δ: 6.35-6.68(m, 2H), 7.04(t, J=7.6 Hz, 2H), 7.26-7.98(m, 18H), 8.12(d, J=7.7 Hz, 2H), 8.88-8.94(m, 2H)

EXAMPLE 29

Preparation of N,N-bis[3-(2-pyridyl)phenyl]-2-biphenylamine

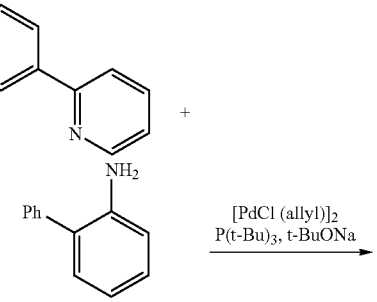

230 mg of the title compound was obtained as glassy solid in a similar manner to Example 1 from 423 mg of 2-biphenylamine with 1 g of 2-(3-chlorophenyl)pyridine.

$^1$H-NMR(CDCl$_3$)δ: 6.88-7.52(m, 21H), 7.61-7.72(m, 2H), 8.58-8.63(m, 2H)

EXAMPLE 30

Preparation of a Platinum Complex

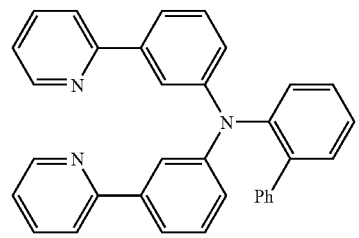

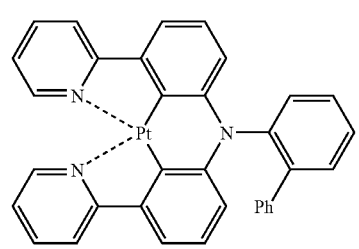

172 mg of the target platinum complex was obtained as reddish crystal in a similar manner to Example 26 from 230 mg of platinum chloride (II) with 128 mg of N,N-bis[3-(2-pyridyl)phenyl]-2-biphenylamine.

$^1$H-NMR(DMSO-d$_6$)δ: 6.15-6.21(m, 2H), 6.94(t, J=7.8 HZ, 2H), 7.02-7.68(m, 13H), 8.01-8.21(m, 2H), 9.03-9.10(m, 2H)

EXAMPLE 31

Preparation of N,N-bis[5-(2-pyridyl)biphenyl-3-yl]aniline

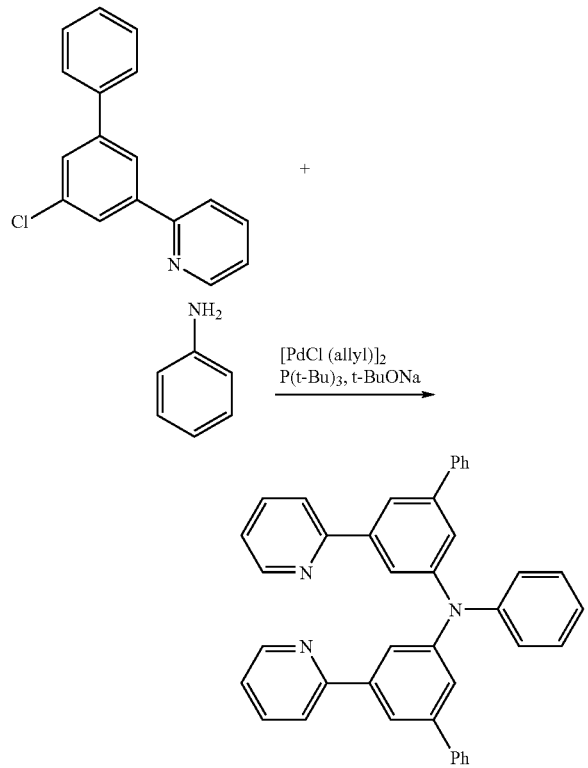

167 mg of the title compound was obtained as glassy solid in a similar manner to Example 1 from 27.1 mg of aniline with 178 mg of 2-(3-phenyl-5-chlorophenyl)pyridine.

$^1$H-NMR(CDCl$_3$)δ: 7.15-8.03(m, 27H), 8.65-8.69(m, 2H)

EXAMPLE 32

Preparation of a Platinum Complex

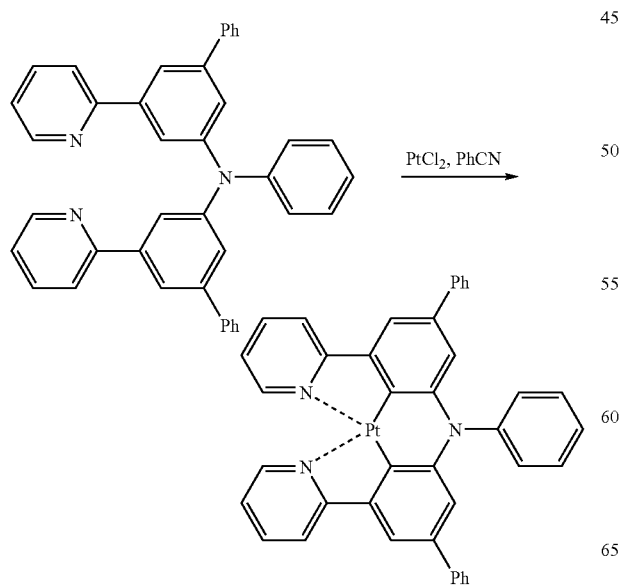

170 mg of the target platinum complex was obtained as reddish crystal in a similar manner to Example 26 from 89 mg of platinum chloride (II) with 167 mg of N,N-bis[5-(2-pyridyl)biphenyl-3-yl]aniline.

$^1$H-NMR(DMSO-d$_6$)δ: 7.28-7.77(m, 21H), 8.05-8.21(m, 2H), 8.40-8.51(m, 2H), 9.10-9.19(m, 2H)

EXAMPLE 33

Preparation of N,N-bis[3-(2-pyridyl)phenyl]-4-diphenylaminoaniline

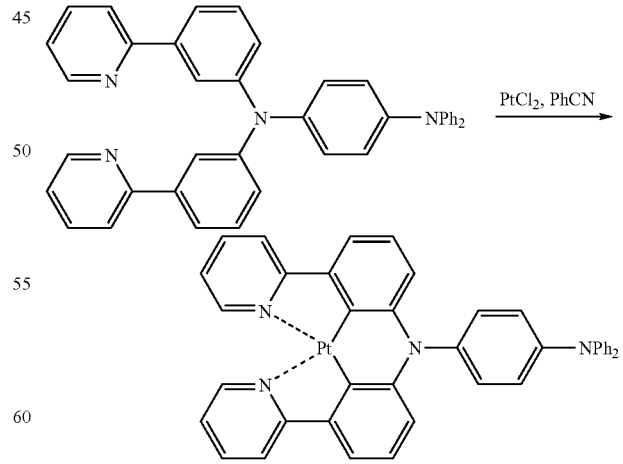

218 mg of the title compound was obtained as glassy solid in a similar manner to Example 1 from 300 mg of 4-(N,N-diphenylamino)aniline with 300 mg of 2-(3-chlorophenyl)pyridine.

EXAMPLE 34

Preparation of a Platinum Complex 131 mg of the target platinum complex was obtained as reddish crystal in a similar manner to Example 26 from 101 mg of platinum chloride (II) with 216 mg of N,N-bis[3-(2-pyridyl)phenyl]-4-diphenylaminoaniline.

$^1$H-NMR(CD$_2$Cl$_2$)δ: 6.48(d, J=8.8 Hz, 2H), 7.04-7.50(m, 20H), 7.76-8.11(m, 4H), 8.81-9.01(m, 2H)

EXAMPLE 35

Preparation of 6,6'-bis(diphenylamino)-2,2'-bipyridine

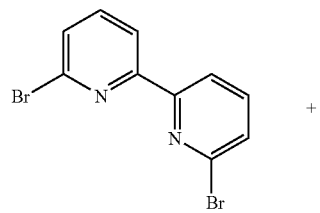

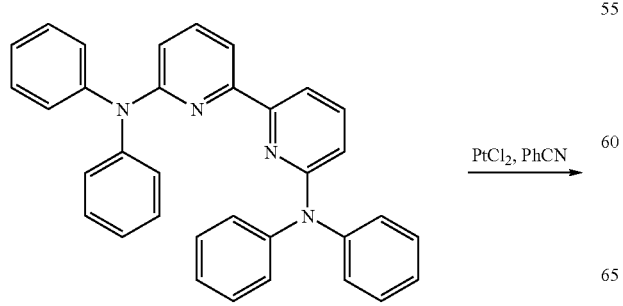

132 mg of the title compound was obtained as white solid in a similar manner to Example 1 from 250 mg of 6,6'-dibromo-2,2'-bipyridine with 296 mg of diphenylamine.

$^1$H-NMR(CDCl$_3$)δ: 6.64(d, J=8.0 Hz, 2H), 7.09-7.54(m, 24H)

EXAMPLE 36

Preparation of a Platinum Complex

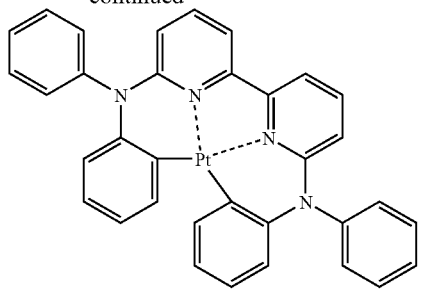

87 mg of the target platinum complex was obtained as reddish crystal in a similar manner to Example 26 from 70 mg of platinum chloride (II) with 130 mg of 6,6'-bis(diphenylamino)-2,2'-bipyridine.

$^1$H-NMR(CDCl$_3$)δ: 6.30-6.53(m, 2H), 6.76-6.82(m, 6H), 7.50-7.59(m, 8H), 7.65-7.70(m, 8H)

EXAMPLE 37

Preparation of N,N-bis[6-(2,4-difluorophenyl)pyridine-2-yl]aniline

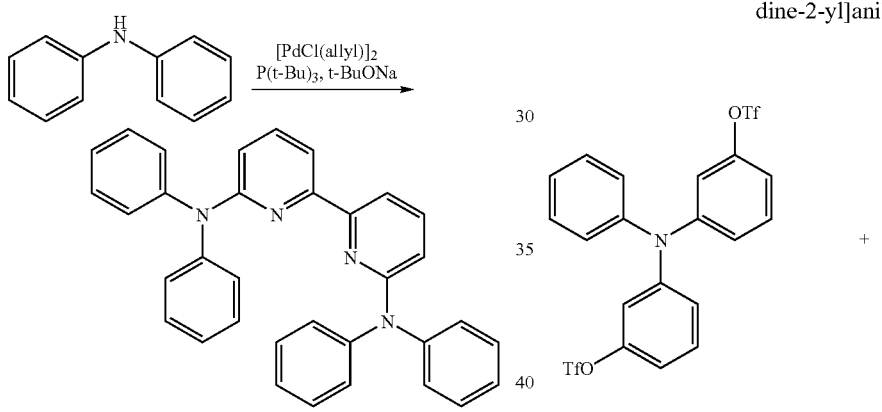

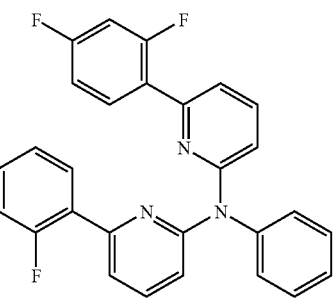

In a nitrogen atmosphere, palladium acetate (4.8 mg) and a hexane solution of tri-t-butylphosphine (10 wt %, 0.086 ml) were added to toluene, and the mixture was stirred for a while.

Then, sodium carbonate (313 mg), 2,4-difluorophenyl boronic acid (445 mg) and N,N-bis[6-trifluoromethanesulfonyloxy]pyridine-2-yl]aniline (686 mg) were added to the mixture, and the reaction mixture was stirred at 100° C. for 1 day. After the reaction mixture was allowed to cool, water was added to the reaction mixture, the organic layer was separated, solvent of the organic layer was distilled off, and the residue was purified by silica gel column chromatography, thereby obtaining target compound as glassy solid (504 mg).

$^1$H-NMR(CDCl$_3$)δ: 6.78-6.91(m, 4H), 7.03(d, J=8.2 Hz, 2H), 7.26-7.48(m, 7H), 7.59-7.82(m, 4H)

EXAMPLE 38

Preparation of a Platinum Complex

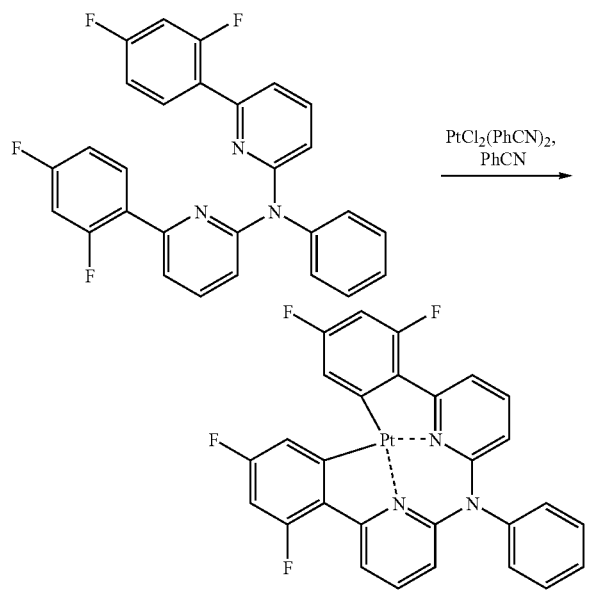

434 mg of the target platinum complex was obtained as yellow crystal in a similar manner to Example 2 from 406 mg of dichlorobis(benzonitrile)platinum with 404 mg of N,N-bis[6-(2,4-difluorophenyl)pyridine-2-yl]aniline.

$^1$H-NMR(DMSO-d$_6$)δ: 6.66(d, J=8.2 Hz, 2H), 6.98-7.05(m, 2H), 7.51-7.85(m, 7H), 7.99(d, J=8.2 HZ, 2H), 8.08(t, J=7.8 Hz, 2H)

EXAMPLE 39

Preparation of 6-(9H-carbazole-9-yl)-6'-diphenylamino-2,2'-bipyridine

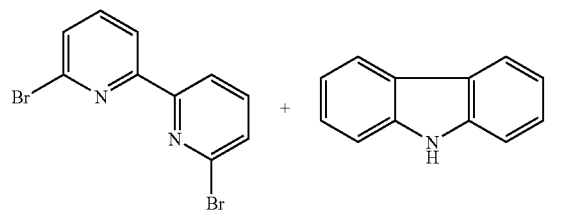

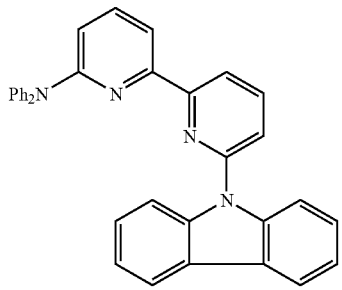

As a similar manner to Example 1, a reactant obtained by 6,6'-dibromo-2,2'-bipyridine (500 mg) and diphenylamine (269 mg) was purified by silica gel column chromatography thereby obtaining target compound as white solid (195 mg).

$^1$H-NMR(CDCl$_3$)δ: 6.78(d, J=9.2 Hz, 1H), 7.19-7.63(m, 16H), 7.89-8.02(m, 5H), 8.13(d, J=8.4 Hz, 2H)

EXAMPLE 40

Preparation of a Platinum Complex 200 mg of the target platinum complex was obtained as reddish crystal in a similar manner to Example 26 from 163 mg of platinum chloride (II) with 300 mg of 6-(9H-carbazole-9-yl)-6'-diphenylamino-2,2'-bipyridine.

$^1$H-NMR(DMSO-d$_6$)δ: 6.50-6.58(m, 1H), 6.79-6.84(m, 2H), 6.94(d, J=9.0 Hz, 1H), 7.20-7.29(m, 1H), 7.39-7.90(m, 10H), 8.00-8.65(m, 7H)

EXAMPLE 41

Preparation of 6-(3-acetoxythiophene-2-yl)-6'-phenyl-2,2'-bipyridine

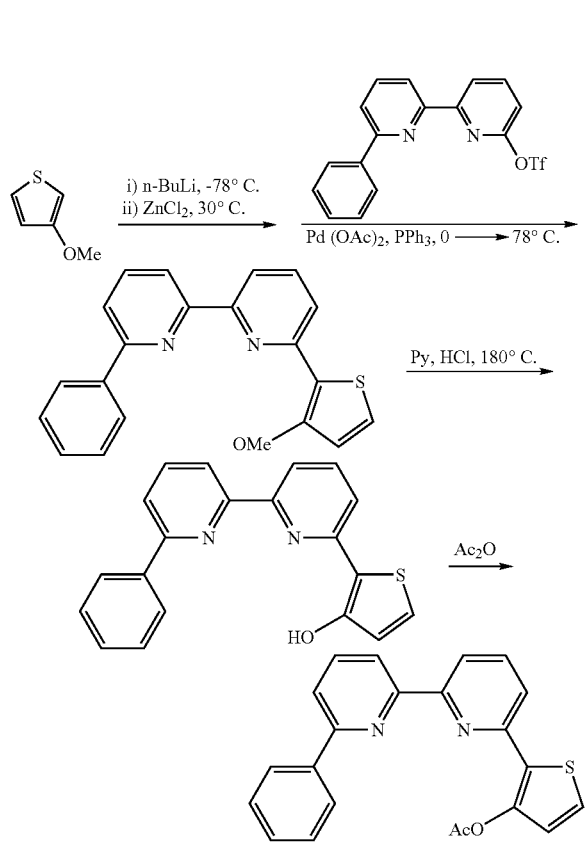

In a nitrogen atmosphere, a tetrahydrofuran (5 ml) solution of 3-methoxythiphene (297 mg) was cooled to −78° C., n-butyllithium(1.57 M hexane solution, 1.7 ml) was dropwise added thereto. After dropwise, the mixture was stirred for 1 hour, zinc chloride (370 mg) was added to the mixture, then the temperature of the reaction mixture was allowed to warm to 30° C. by degree. Thereafter, 6-phenyl-6'-trifluoromethanesulfonyloxy-2,2'-bipyridine (790 mg), palladium acetate (9.7 mg) and triphenylphosphine were added to the reaction mixture, the temperature of the reaction mixture was raised to 78° C., and stirring for 1 day. Water was added to the reaction mixture, the mixture was extracted with toluene, solvent of organic layer was distilled off, thus crude coupling product was obtained. Concentrated hydrochloric acid and pyridine were added to the crude product, then the mixture was stirred at 180° C. for 3 hours. After the reaction mixture was cooled, to which was then added an aqueous 1 mol/L sodium hydroxide solution, the mixture was extracted with dichloromethane, the solvent was distilled off, thus crude hydroxy compound was obtained. Pyridine was added to the obtained crude hydroxy compound, acetic anhydride was added thereto, then the mixture was stirred for 24 hours. A solvent of the reaction mixture was distilled off, and the residue was purified by silica gel column chromatography, thereby obtaining target compound as viscous oil (450 mg).

$^1$H-NMR(CDCl$_3$)δ: 2.40(s, 3H), 7.06(d, J=5.4 Hz, 2H), 7.18-7.54(m, 4H), 7.74-8.00(m, 4H), 8.13-8.21(m, 2H), 8.51 (t, J=7.6 HZ, 2H)

EXAMPLE 42

Preparation of a Platinum Complex

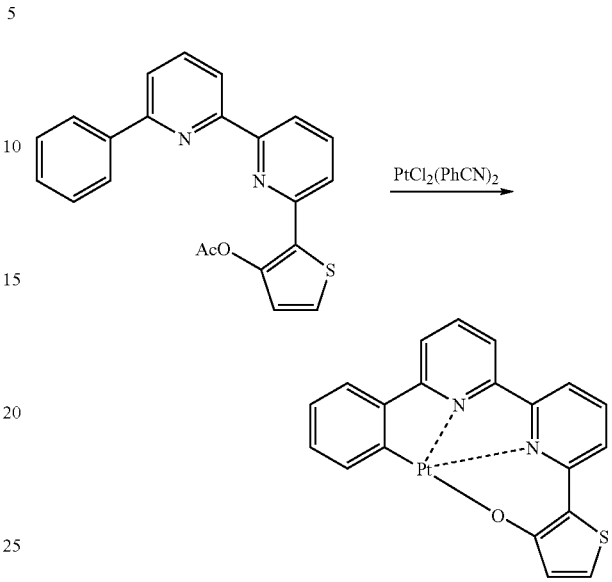

In a nitrogen atmosphere, a mixture of dichlorobis(benzonitrile)platinum (II) (259 mg), 6-(3-acetoxythiophene-2-yl)-6'-phenyl-2,2'-bipyridine (225 mg) and 2-ethoxyethanol was stirred at 150° C. for 1 day. After the reaction mixture was allowed to cool, water was added to the reaction mixture, and the mixture was extracted with dichloromethane. The solvent of the organic layer was distilled off, and the residue was purified by silica gel column chromatography, thereby obtaining target platinum complex as orange solid.

$^1$H-NMR(DMSO-d$_6$)δ: 6.93(d, J=7.6 Hz, 1H), 7.08-7.44 (m, 3H), 7.69-7.78(m, 2H), 7.94-8.34(m, 6H)

EXAMPLE 43

Preparation of 3,3'-bis(2-pyridyloxy)biphenyl

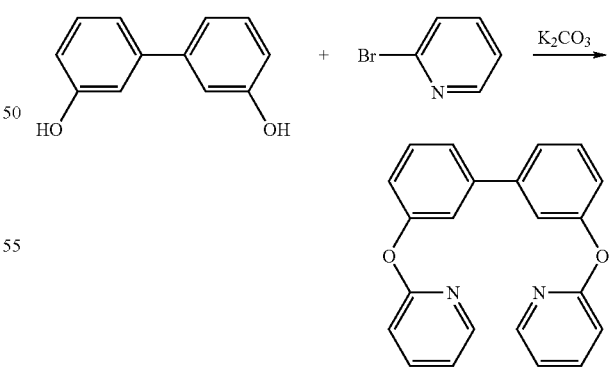

In a nitrogen atmosphere, a mixture of 3,3'-biphenol (1.0 g, 5.4 mmol), 2-bromopyridine (1.3 ml, 13.5 mmol) and potassium carbonate (1.1 g, 8.1 mmol) was stirred at 200° C. for 4 hours. After the reaction mixture was allowed to cool, water and dichloromethane were added to the reaction mixture for extraction. The solvent of the organic layer was distilled off, and the residue was purified by silica gel column chromatography and crystallization, thereby obtaining 1.1 g of 3,3'-bis(2-pyridiyloxy)biphenyl as white powder. Yield: 59.8%.

$^1$H-NMR(CDCl$_3$)δ: 6.93(d, J=8.6 Hz, 2H), 6.96-7.05(m, 2H), 7.12(dt, J=6.4, 2.6 HZ, 2H), 7.33-7.52(m, 6H), 7.69 (ddd, J=2.0, 7.4, 8.4 HZ, 2H), 8.21(dd, J=2.0, 5.2 Hz, 2H)

EXAMPLE 44

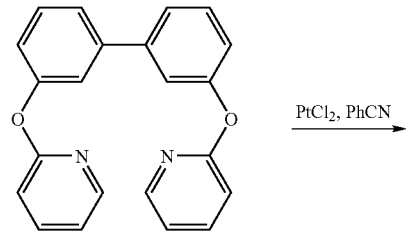

A mixture of platinum chloride (II) (391 mg, 1.47 mmol), 3,3'-bis(2-pyridyloxy)biphenyl (500 mg, 1.47 mmol) and benzonitrile (40 ml) was stirred under reflux for 3 hours. After the reaction mixture was allowed to cool, the solvent was distilled off, and the residue was purified by silica gel column chromatography and crystallization, thereby obtaining 540 mg of target platinum complex as yellow powder. Yield: 68.9%.

$^1$H-NMR(CD$_2$Cl$_2$)δ: 6.85(dd, J=1.0, 8.0 Hz, 2H), 7.00(dd, J=7.4, 8.0 HZ, 2H), 7.09(ddd, J=1.4, 6.0, 7.2 Hz, 2H), 7.21 (dd, J=1.0, 7.2 HZ, 2H), 7.36(ddd, J=0.5, 1.4, 8.5 HZ, 2H), 7.95(ddd, J=2.0, 7.2, 8.5 Hz, 2H)

EXAMPLE 45

Preparation of carbonylbis[3-(2-pyridyl)benzene]

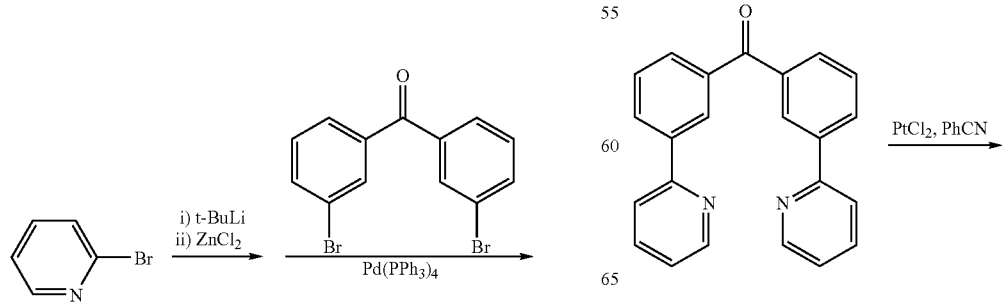

-continued

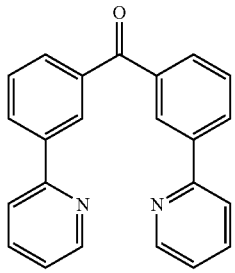

In a nitrogen atmosphere, a n-pentane solution of t-butyllithium (17.8 ml, 1.60M, 28.5 mmol) was dropwise added to tetrahydrofuran cooled to −70° C., then a tetrahydrofuran (5 ml) solution of 2-bromopyridine (1.2 ml, 12.9 mmol) was added thereto while 15 minutes, after a dropwise, the mixture was stirred at −70° C. for 30 minutes. Then, a tetrahydrofuran solution of zinc chloride (31.8 ml, 0.50 M, 15.9 mmol) was added to the mixture while 10 minutes. Thereafter, the temperature of the reaction mixture was allowed to warm to room temperature while 1 hour, tetrakis(triphenylphosphine)palladium (203 mg) and 3,3'-dibromobenzophenone (2.0 g, 5.88 mmol) were successively added thereto, the reaction mixture was stirred under reflux for 18 hours. After the reaction mixture was allowed to cool, then the mixture was poured into a mixture of ethylenediaminetetraacetic acid (7.0 g)/an aqueous saturated sodium hydrogen carbonate solution (210 ml), an organic layer was separated, furthermore an aqueous layer was extracted with toluene. The organic layer was combined, and the solvent was distilled off, and the residue was purified by silica gel column chromatography and recrystallization, thereby obtaining 1.5 g of carbonylbis[3-(2-pyridyl)benzene as white powder. Yield: 75.8%.

$^1$H-NMR(CDCl$_3$)δ: 7.22-7.34(m, 2H), 7.62(dt, J=0.4, 7.8 Hz, 2H), 7.74-7.84(m, 4H), 7.88(dt, J=7.8, 1.4 HZ, 2H), 8.30(ddd, J=1.4, 1.8, 7.6 Hz, 2H), 8.45(t, J=1.6 Hz, 2H), 8.71(dt, J=4.4, 1.6 HZ, 2H)

EXAMPLE 46

Preparation of a Platinum Complex

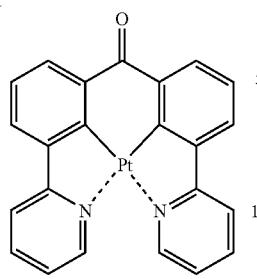

A mixture of platinum chloride (II) (395 mg, 1.49 mmol), carbonylbis[3-(2-pyridyl)benzene] (500 mg, 1.49 mmol) and benzonitrile (40 ml) was stirred under reflux for 3 hours. After the reaction mixture was allowed to cool, the precipitate was filtered and collected, then the collected precipitate was purified by sublimation, thereby obtaining 600 mg of target platinum complex as yellow powder. Yield: 76.1%.

Mass Spectrum(EI): m/z=529(M$^+$)

EXAMPLE 47

(a) Preparation of N-mesityl-N-2-[6-(2-pyridyl)pyridine-2-yl]-3,5-diphenylaniline

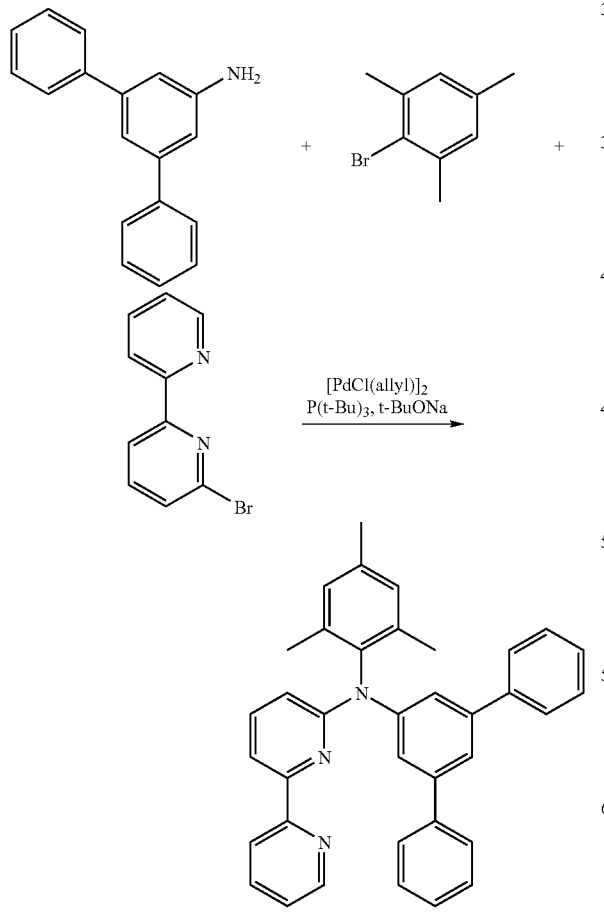

133 mg of the title compound was obtained as glassy solid in a similar manner to Example 1 from 365 mg of 3,5-diphenylaniline with 350 mg of 2-bromo-6-(2-pyridyl)pyridine and 296 mg of 2-bromomesitylene.

$^1$H-NMR(CDCl$_3$)δ: 2.25(s, 6H), 2.36(s, 3H), 6.69(d, J=1.6 Hz, 2H), 6.89-6.96(m, 4H), 7.17(t, J=1.5 Hz, 1H), 7.24-7.61 (m, 15H)

(b) Preparation of a Platinum Complex

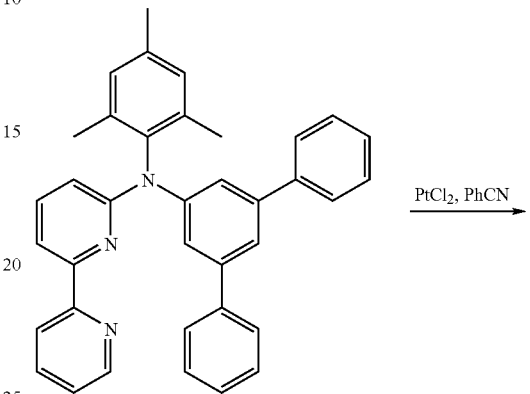

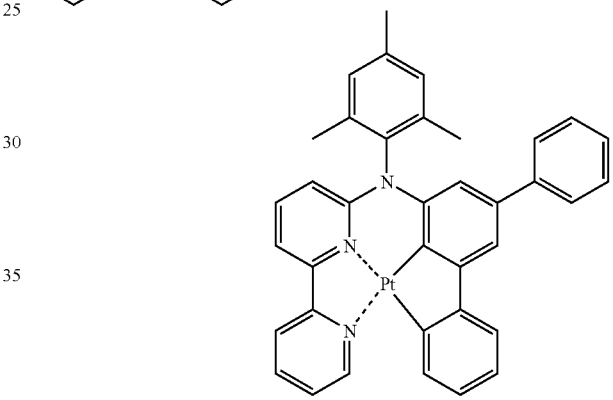

60 mg of the target platinum complex was obtained as reddish crystal in a similar manner to Example 26 from 68 mg of platinum chloride (II) with 133 mg of N-mesityl-N-2-(6-(2-pyridyl)pyridine-2-yl]-3,5-diphenylaniline.

$^1$H-NMR(CDCl$_3$)δ: 1.92(s, 6H), 2.49(s, 3H), 6.18(d, J=1.6 Hz, 1H), 6.65(d, J=8.2 Hz, 1H), 6.91-7.02(m, 2H), 7.31-7.84 (m, 10H), 7.97-8.13(m, 2H), 8.24(d, J=7.0 Hz, 1H), 8.42(dt, J=1.6, 8.2 Hz, 1H), 8.78(d, J=8.0 Hz, 1H), 9.62(d, J=5.7 Hz, 1H)

EXAMPLE 48

(a) Preparation of N,N-bis[3-(2-thiazolyl)phenyl]aniline

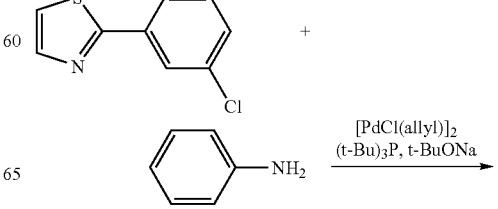

-continued

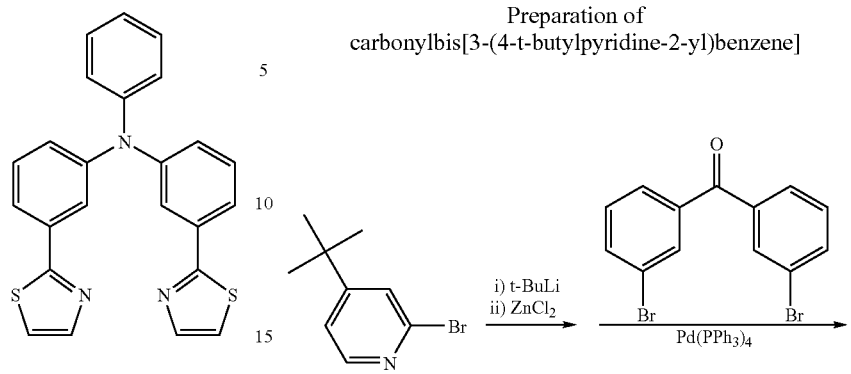

96.3% yield of N,N-bis[3-(2-thiazolyl)phenyl]aniline was obtained as white powder in a similar manner to Example 47 (a) from aniline with 2-(3-chlorophenyl)thiazole.

$^1$H-NMR(CDCl$_3$)δ: 7.06(tt, J=1.4, 7.2 Hz, 1H), 7.12-7.21 (m, 4H), 7.24-7.39(m, 8H), 7.60(ddd, J=1.0, 1.6, 7.8 Hz, 2H), 7.75(t, J=2.0 Hz, 2H), 7.81(d, J=3.4 Hz, 2H)

(b) Preparation of a Platinum Complex

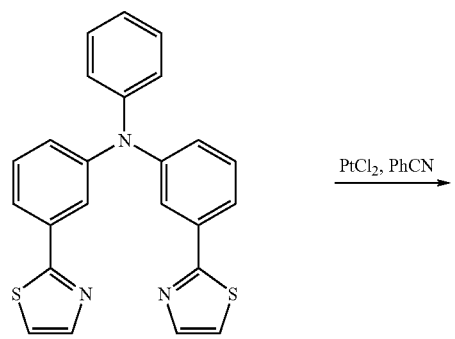

27.3% yield of the target platinum complex was obtained in a similar manner to Example 47 from platinum chloride (II) with N,N-bis[3-(2-thiazolyl)phenyl]aniline.

$^1$H-NMR(CD$_2$Cl$_2$)δ: 6.18(ddd, J=1.0, 8.5, 18.4 Hz, 2H), 6.92(dd, J=7.3, 8.4 Hz, 2H), 7.21(dd, J=0.8, 7.2 Hz, 2H), 7.28-7.33(m, 2H), 7.49(d, J=3.5 Hz, 2H), 7.52(tt, J=1.2, 7.2 Hz, 1H), 7.64-7.68(m, 2H), 8.02(d, 2H)

EXAMPLE 49

Preparation of carbonylbis[3-(4-t-butylpyridine-2-yl)benzene]

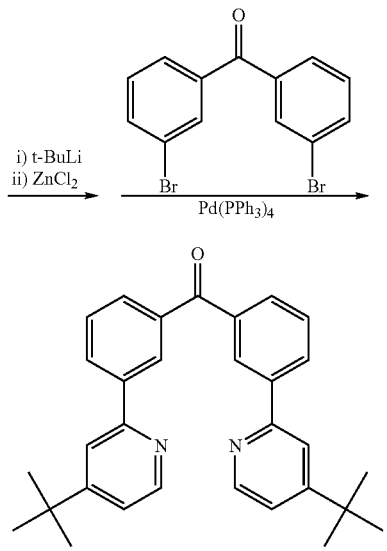

75.0% yielding of Carbonylbis[3-(4-t-butylpyridine-2-yl) benzene] was obtained as glassy solid in the same manner as with Example 45, except substitution 2-bromo-4-t-butylpyridine for 2-bromopyridine.

$^1$H-NMR(CDCl$_3$)δ: 1.36(s, 18H), 7.27(dd, J=1.6, 5.4 Hz, 2H), 7.60(t, J=7.6 Hz, 2H), 7.72-7.78(m, 2H), 7.86(d, J=7.8 Hz, 2H), 8.26(d, J=7.8 Hz, 2H), 8.44(s, 2H), 8.60(d, J=5.4 Hz, 2H)

EXAMPLE 50

Preparation of Platinum Complex

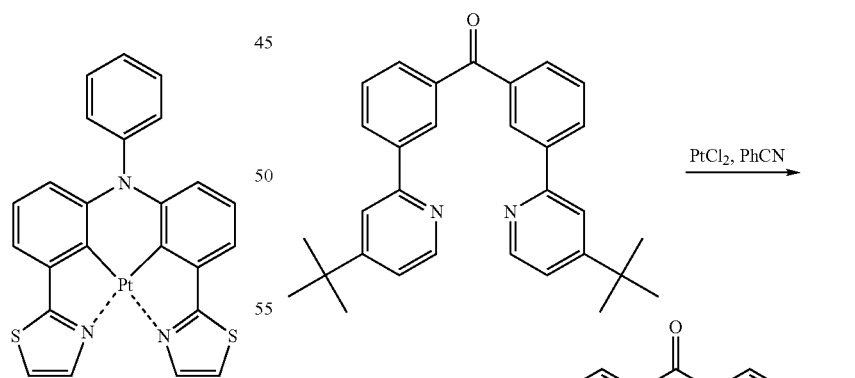

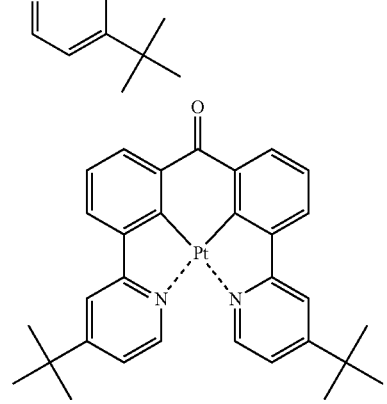

The reaction was conducted in the same manner as with Example 46, except substitution carbonylbis[3-(4-t-butylpyridine-2-yl)benzene] for carbonylbis[3-(2-pyridine-2-yl)benzene]. The solvent of the reaction mixture was distilled off, and the residue was purified by silica gel column chromatography and crystallization, thereby obtaining target platinum complex as yellow powder.

Yield: 46.8%.

$^1$H-NMR(CDCl$_3$)δ: 1.42(s, 18H), 7.16-7.28(m, 4H), 7.66-7.76(m, 4H), 8.27(dt, J=1.0, 7.6, 12.8 Hz, 2H), 8.52(d, J=6.0 Hz, 2H)

EXAMPLE 51

Preparation of N,N-bis[3-(2-pyridyl)phenyl]-4-n-octylaniline

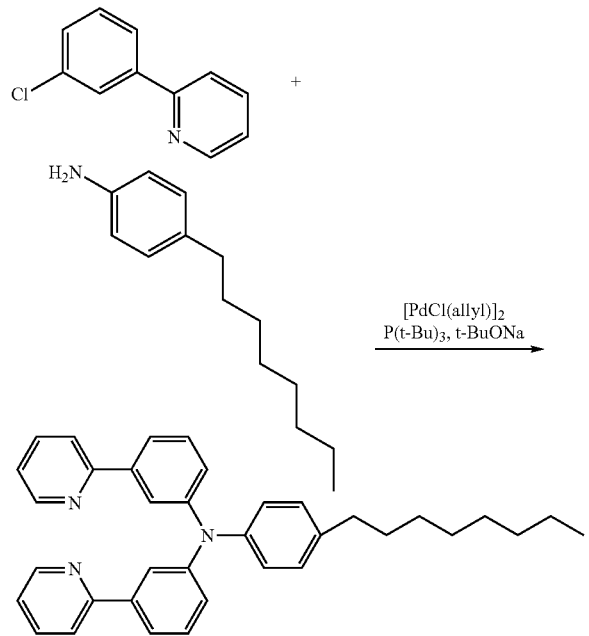

819 mg of the title compound was obtained as glassy solid in a similar manner to Example 1 from 400 mg of 4-n-octylaniline with 776 mg of 2-(3-chlorophenyl)pyridine.

EXAMPLE 52

Preparation of Platinum Complex

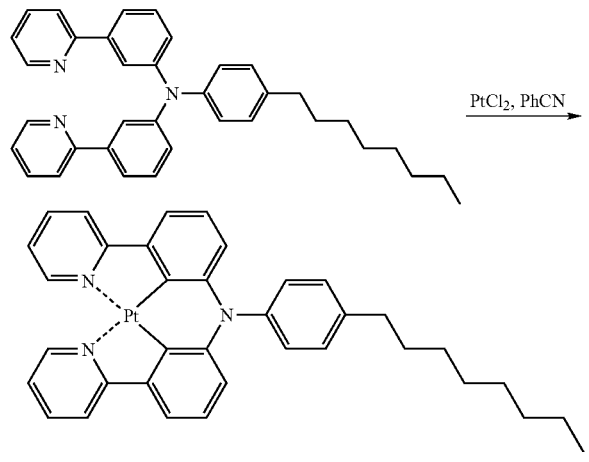

325 mg of the target platinum complex was obtained in a similar manner to Example 26 from 212 mg of platinum chloride (II) with 409 mg of N,N-bis[3-(2-pyridyl)phenyl]-4-n-octylaniline.

$^1$H-NMR(DMSO-d$_6$)δ: 0.86-0.89(m, 3H), 1.28-1.72(m, 12H9, 2.74(t, J=7.4 Hz, 2H), 6.08-6.22(m, 2H), 6.93-6.97(m, 2H), 7.14-7.16(m, 2H), 7.59(d, J=7.0 Hz, 2H), 7.50(d, J=8.3 Hz, 2H), 8.06-8.10(m, 2H), 8.20(d, J=8.0 Hz, 2H), 9.06-9.15 (m, 2H)

EXAMPLE 53

Preparation of bis[3-(2-pyridyl)phenyl]dimethylsilane

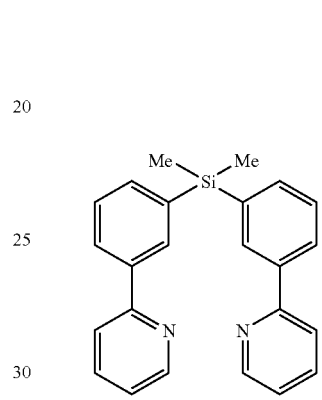

$^1$H-MR(CDCl$_3$)δ: 0.67(s, 6H), 7.21(ddd, J=2.4, 4.6, 8.4 Hz, 2H), 7.47(t, J=7.6 Hz, 2H), 7.70(dt, J=7.4, 1.2 Hz, 2H), 7.65-7.80(m, 4H), 7.99(dt, J=7.8, 1.4 Hz, 2H), 8.17(s, 2H), 8.69(ddd, J=1.0, 1.6, 5.2 Hz, 2H).

EXAMPLE 54

Preparation of bis[3-(2-pyridyl)phenyl]diphenylsilane

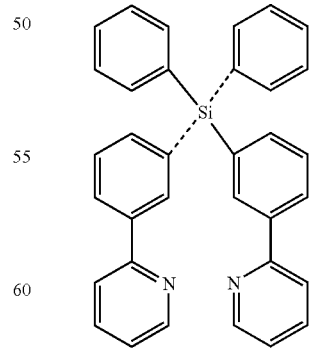

$^1$H-NMR(CDCl$_3$)δ: 7.18(brs, 2H), 7.33-7.75(m, 18H), 8.13(dd, J=1.0, 7.8 Hz, 2H), 8.20(s, 2H), 8.65(brd, J=5.2 Hz, 2H)

EXAMPLE 55

Preparation of 9,9-bis[3-(2-pyridyl)phenyl]9H-silafluorene

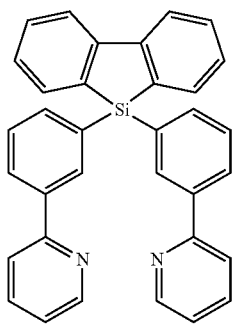

$^1$H-NMR(CDCl$_3$)δ: 7.19(ddd, J=1.4, 3.8, 7.0 Hz, 2H), 7.34 (dt, J=1.0, 7.4 Hz, 2H), 7.42-7.56(m, 4H), 7.56-7.80(m, 6H), 7.89(t, J=8.2 Hz, 4H), 8.07(dt, J=8.0, 1.6 Hz, 2H), 8.25(s, 2H), 8.65(d, J=4.6 Hz, 2H)

EXAMPLE 56

Preparation of 9,9-bis[3-(2-pyridyl)phenyl]-9H-fluorene

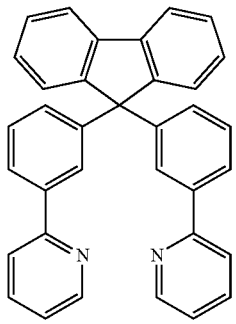

$^1$H-NMR(CDCl$_3$)δ: 7.15(ddd, J=1.2, 4.8, 7.4 Hz, 2H), 7.27-7.44(m, 8H), 7.45-7.56(m, 4H), 7.64(dt, J=1.8, 7.8 Hz, 2H), 7.74-7.84(m, 4H), 7.88(dt, J=7.2, 1.8 Hz, 2H), 8.61(d, J=4.6 Hz, 2H)

EXAMPLE 57

(a) Preparation of N,N-bis[3-(4-t-butylpyridine-2-yl)phenyl]aniline

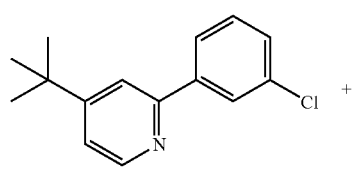

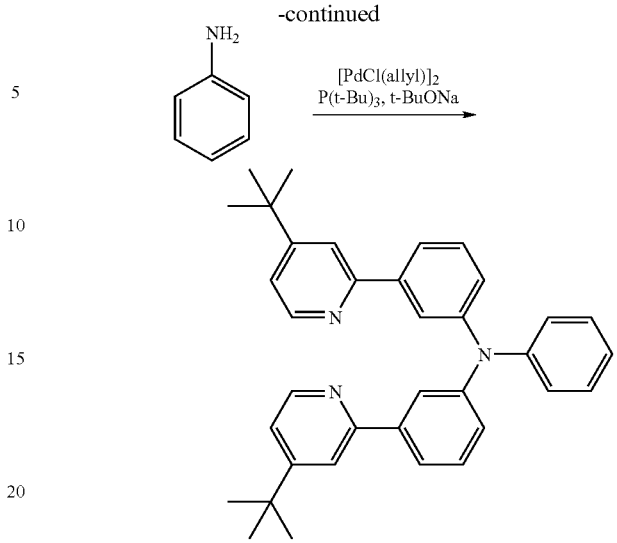

364 mg of the title compound was obtained as glassy solid in a similar manner to Example 1 from 88 mg of aniline with 464 mg of 2-(3-chlorophenyl)-4-t-butylpyridine.

$^1$H-NMR(CDCl$_3$)δ: 1.31(s, 18H), 7.15-7.40(m, 10H), 7.58-7.79(m, 7H), 8.52(d, J=5.4 Hz, 2H)

(b) Preparation of Platinum Complex

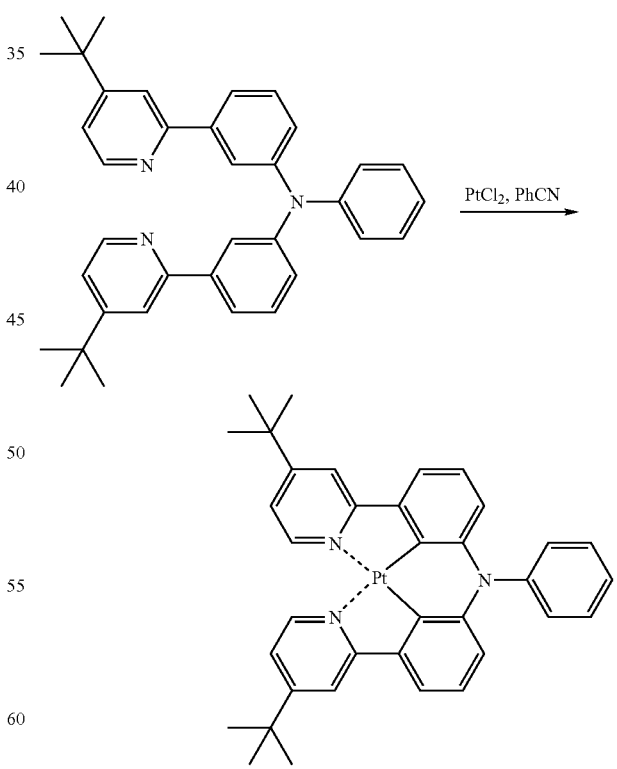

325 mg of the target platinum complex was obtained as reddish crystal in a similar manner to Example 26 from 179 mg of platinum chloride (II) with 344 mg of N,N-bis[3-(4-t-butylpyridine-2-yl)phenyl]aniline.

$^1$H-NMR(DMSO-d$_6$)δ: 1.14(s, 18H), 6.09(d, J=8.4 Hz, 2H), 6.89-6.99(m, 2H), 7.25-7.78(m, 9H), 8.13(br, 2H), 8.97-9.02(m, 2H)

EXAMPLE 58

Preparation of 6-diphenylamino-6'-phenyl-2,2'-bipyridine

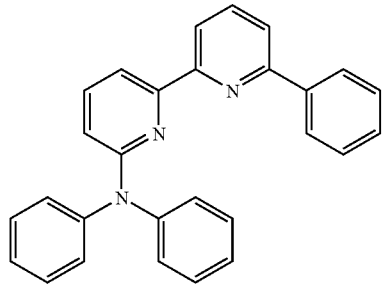

$^1$H-NMR(CDCl$_3$)δ: 6.75(dd, J=0.6, 8.2 Hz, 1H), 7.12-7.55 (m, 13H), 7.60(t, J=7.9 Hz, 1H), 7.66-7.78(m, 2H), 7.95(dd, J=2.4, 6.2 Hz, 1H), 8.08-8.20(m, 3H).

EXAMPLE 59

Preparation of 6-(9H-carbazole-9-yl)-6'-phenyl-2,2'-bipyridine

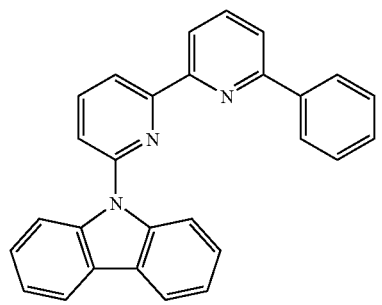

$^1$H-NMR(CDCl$_3$)δ: 7.35(dt, J=1.2, 7.6 Hz, 2H), 7.42-7.62 (m, 5H), 7.68(dd, J=1.0, 8.0 Hz, 1H), 7.81(dd, J=1.2, 7.8 Hz, 1H), 7.91(t, J=7.8 Hz, 1H), 7.97(d, J=8.0 Hz, 2H), 8.09(t, J=7.8 Hz, 1H), 8.12-8.26(m, 4H), 8.46(dd, J=1.4, 7.6 Hz, 1H), 8.67(dd, J=1.0, 7.8 Hz, 1H).

EXAMPLE 60

Preparation of 2-diphenylamino-6-[3-(2-pyridyl)phenyl]pyridine

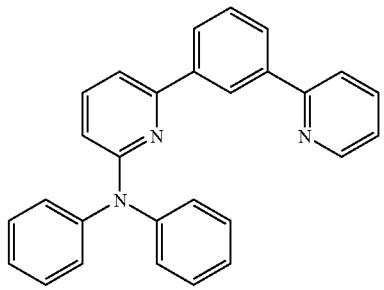

$^1$H-NMR(CDCl$_3$)δ: 6.68(d, J=8.0 Hz, 1H), 7.13-7.58(m, 14H), 7.68(dt, J=1.4, 8.0 Hz, 1H), 7.75(dt, J=2.0, 8.2 Hz, 1H), 7.91(dt, J=1.4, 8.0 Hz, 1H), 8.04(dt, J=1.4, 8.0 Hz, 1H), 8.49(t, J=1.5 Hz, 1H), 8.67-8.75(m, 1H)

EXAMPLE 61

Preparation of 2-phenoxy-6-[3-(2-pyridyloxy)phenyl]pyridine

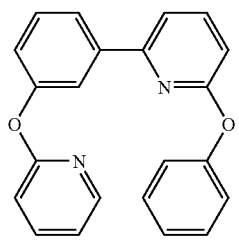

$^1$H-NMR(CDCl$_3$)δ: 6.77(dd, J=0.6, 8.0 Hz, 1H), 6.90(dt, J=8.2, 0.8 Hz, 1H), 7.00(ddd, J=1.0, 5.2, 7.4 Hz, 1H), 7.10-7.24(m, 4H), 7.30-7.50(m, 4H), 7.62-7.80(m, 4H), 8.20(ddd, J=0.8, 2.0, 5.2 Hz, 1H)

EXAMPLE 62

Preparation of 3,3'-bis[N-phenyl-N-(2-pyridyl)amino]biphenyl

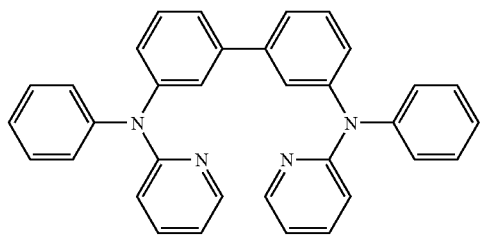

$^1$H-NMR(CDCl$_3$)δ: 6.72-6.84(m, 4H), 7.08-7.38(m, 18H), 7.44(ddd, J=2.0, 7.4, 8.4 Hz, 2H), 8.18-8.26(m, 2H)

EXAMPLE 63

Preparation of 2-diphenylamino-6-{3-[N-phenyl-N-(2-pyridyl)amino]phenyl}pyridine

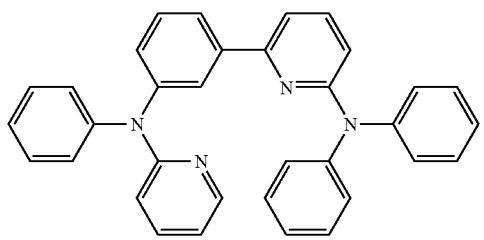

¹H-NMR(CDCl₃)δ: 6.60(d, J=8.2 Hz, 1H), 6.70-6.84(m, 2H), 7.00-7.50(m, 20H), 7.60(d, J=8.0 Hz, 1H), 7.70(t, J=1.8 Hz, 1H), 8.23(dd, J=1.6, 4.6 Hz, 1H)

EXAMPLE 64

Preparation of 6-diphenylaminopyridine-2-yl 6-phenylpyridine-2-yl ether

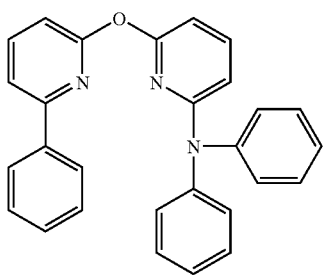

¹H-NMR(CDCl₃)δ: 6.43(d, J=8.0 Hz, 1H), 6.58(d, J=7.6 Hz, 1H), 6.91(dd, J=0.6, 8.0 Hz, 1H), 6.96-7.24(m, 10H), 7.36-7.56(m, 5H), 7.63(7.6 Hz, 1H), 7.94-8.03(m, 2H)

EXAMPLE 65

Preparation of 6-(9H-carbazole-9-yl)pyridine-2-yl 6-phenylpyridine-2-yl ether

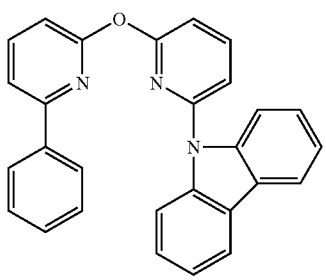

¹H-NMR(CDCl₃)δ: 6.98-7.24(m, 6H), 7.38-7.52(m, 4H), 7.63(d, J=7.6 Hz, 1H), 7.78(d, J=8.4 Hz, 2H), 7.81(t, J=7.6 Hz, 1H), 7.92-8.10(m, 5H)

EXAMPLE 66

Preparation of 2,2'-oxybis(6-diphenylaminopyridine)

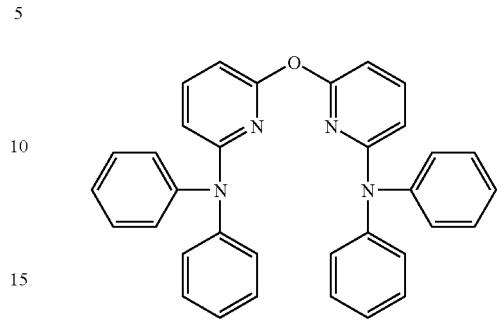

¹H-NMR(CDCl₃)δ: 6.36(d, J=7.8 Hz, 2H), 6.44(d, J=7.8 Hz, 2H), 7.03-7.15(m, 14H), 7.20-7.32(m, 6H), 7.36(t, J=7.8 Hz, 2H)

EXAMPLE 67

Preparation of 2,2'-oxybis[6-(9H-carbazole-9-yl)pyridine]

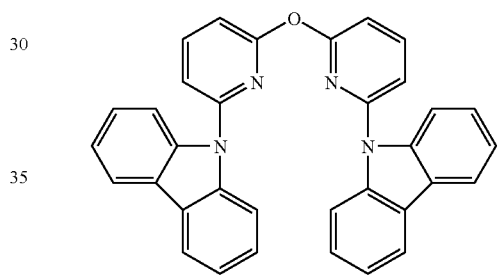

¹H-NMR(CDCl₃)δ: 7.08-7.24(m, 10H), 7.44(d, J=7.8 Hz, 2H), 7.75-7.84(m, 4H), 7.97(t, J=7.8 Hz, 2H), 7.98-8.08(m, 4H)

EXAMPLE 68

Preparation of N,N-bis[3-(2-pyridyloxy)phenyl]aniline

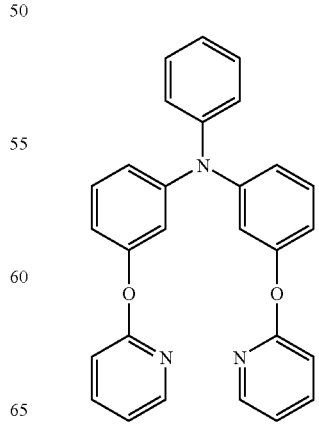

$^1$H-NMR(CDCl$_3$)δ: 6.77(ddd, J=1.0, 2.4, 8.0 Hz, 2H), 6.85 (dt, J=0.6, 8.8 Hz, 2H), 6.86-7.08(m, 7H), 7.14-7.32(m, 6H), 7.64(ddd, J=2.0, 7.2, 8.4 Hz, 2H), 8.18(ddd, J=0.8, 2.0, 5.0 Hz, 2H)

EXAMPLE 69

An organic EL device of a structure shown in FIG. 1 was manufactured.

On a glass substrate (g), an anode (f), a hole-transporting layer (e), a light-emitting layer (d) comprising a host material and a dope material, a hole blocking layer (c), an electron-transporting layer (b) and a cathode (a) were formed successively from the side of the glass substrate (g). In the organic EL device, each of the anode (f) and the cathode (a) are connected to a lead wire, and voltage could be applied between the anode (f) and the cathode (a).

The anode (f) was an ITO film and deposited on the glass substrate (g).

The hole-transporting layer (e) was formed by using the following compound (α-NPD)

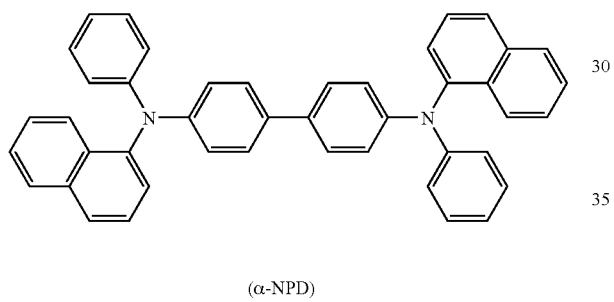

(α-NPD)

and by a vacuum vapor deposition method to a thickness of 40 nm on the anode (f).

The light-emitting layer (d) containing the host material and the phosphorescent material as dopant was formed by using both of the following compound (CBP):

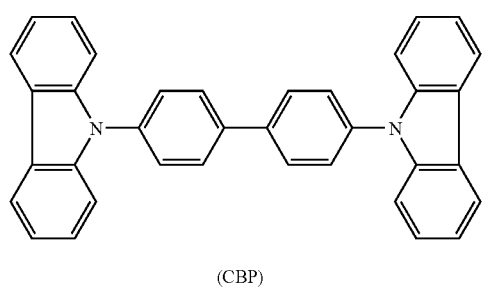

(CBP)

and the platinum complex obtained in Example 2 and by vacuum vapor co-deposition (doping amount 3% by weight) to a thickness of 35 nm over the hole-transporting layer (e).

The hole blocking layer (c) was formed by using the following compound (BCP)

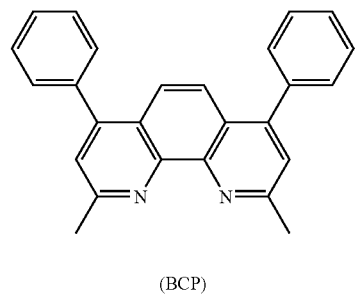

(BCP)

to a thickness of 10 nm on the light-emitting layer (d) by a vacuum vapor deposition method.

The electron-transporting layer (b) was formed by using the following compound (Alq$_3$):

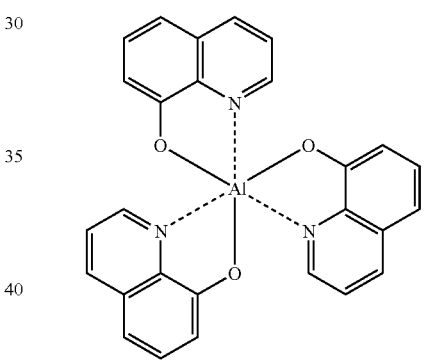

(Alq$_3$)

to a thickness of 35 nm on the hole blocking layer (c) by a vacuum vapor deposition method.

The cathode (a) was formed of a laminate by vacuum vapor co-depositing Mg and Ag at a ratio of 10:1 to a thickness of 100 nm successively from the side of the electron-transporting layer (b) and then further vacuum vapor depositing Ag at a thickness of 10 nm.

Upon applying a plus voltage to the anode (ITO) (f) and a minus voltage to the cathode (a) of the obtained organic EL device, stable light emission was confirmed even at a very low voltage. At the brightness of 100 cd/m$^2$, the luminous efficiency was extremely high as the external quantum efficiency of 4.2% and the power efficiency of 5.3 lm/W of the device. Further, a green light emission of extremely high color purity was obtained due to the compound of the invention used for the light-emitting layer (d), and the CIE chromaticity point at the brightness of 100 dc/m$^2$ was: (x, y)=0.32, 0.55.

EXAMPLE 70

A device having the same device structure as in Example 69 and using the platinum complex obtained in Example 6 for the light-emitting layer (d) was manufactured.

EXAMPLE 71

A device having the same device structure as in Example 69 and using the platinum complex obtained in Example 4 for the light-emitting layer (d) was manufactured.

EXAMPLE 72

A device having the same device structure as in Example 69 and using the platinum complex obtained in Example 12 for the light-emitting layer (d) was manufactured.

EXAMPLE 73

A device having the same device structure as in Example 69 and using the platinum complex obtained in Example 8 for the light-emitting layer (d) was manufactured.

EXAMPLE 74

A device having the same device structure as in Example 69 and using the platinum complex obtained in Example 26 for the light-emitting layer (d) was manufactured.

EXAMPLE 75

A device having the same device structure as in Example 69 and constructed with a laminate formed by using the platinum complex obtained in Example 28 for the light-emitting layer (d) and vacuum vapor depositing LiF at 0.5 nm and Al at 100 nm thickness successively from the side of the electron-transporting layer (b) to the cathode (a) was manufactured.

EXAMPLE 76

A device having the same device structure as in Example 69 and constructed with a laminate formed by using the platinum complex obtained in Example 34 for the light-emitting layer (d) and vacuum vapor depositing LiF at 0.5 nm and Al at 100 nm thickness successively from the side of the electron-transporting layer (b) to the cathode (a) was manufactured.

EXAMPLE 77

A device having the same device structure as in Example 69 and constructed with a laminate formed by using the platinum complex (doping amount 6% by weight) obtained in Example 38 for the light-emitting layer (d), using BAlq for the hole blocking layer (c) and vacuum vapor depositing LiF at 0.5 nm and Al at 100 nm thickness successively from the side of the electron-transporting layer (b) to the cathode (a) was manufactured. BAlq is the following compound.

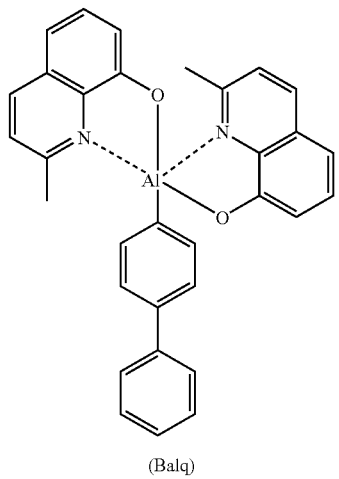

(Balq)

EXAMPLE 78

A device having the same device structure as in Example 69 and constructed with a laminate formed by using the platinum complex (doping amount 6% by weight) obtained in Example 44 for the light-emitting layer (d), and vapor depositing LiF to 0.5 nm and Al to 100 nm thickness successively from the side of the electron-transporting layer (b) to the cathode (a) was manufactured.

EXAMPLE 79

A device having the same device structure as in Example 69 and constructed with a laminate formed by using the platinum complex (doping amount 6% by weight) obtained in Example 32 for the light-emitting layer (d), using BAlq for the hole blocking layer (c) and vapor depositing LiF to 0.5 nm and Al to 100 nm thickness successively from the side of the electron-transporting layer (b) to the cathode (a) was manufactured.

EXAMPLE 80

A device having the same device structure as in Example 69 and constructed with a laminate formed by using the platinum complex (doping amount 6% by weight) obtained in Example 42 for the light-emitting layer (d), using BAlq for the hole blocking layer (c) and vapor depositing LiF to 0.5 nm and Al to 100 nm thickness successively from the side of the electron-transporting layer (b) to the cathode (a) was manufactured.

EXAMPLE 81

A device having the same device structure as in Example 69 and constructed with a laminate formed by using the platinum complex (doping amount 6% by weight) obtained in Example 30 for the light-emitting layer (d), using BAlq for the hole blocking layer (c), and vacuum vapor depositing LiF to 0.5 nm and Al to 100 nm thickness successively from the side of the electron-transporting layer (b) to the cathode (a) was manufactured.

EXAMPLE 82

A device having the same device structure as in Example 69 and constructed with a laminate formed by using the platinum complex (doping amount 6% by weight) obtained in Example 46 for the light-emitting layer (d), and vacuum vapor depositing LiF to 0.5 nm and Al to 100 nm thickness successively from the side of the electron-transporting layer (b) to the cathode (a) was manufactured.

EXAMPLE 83

A device having the same device structure as in Example 27 and constructed with a laminate formed by using the platinum complex (doping amount 6% by weight) obtained in Example 52 for the light-emitting layer (d), and vacuum vapor depositing LiF to 0.5 nm and Al to 100 nm thickness successively from the side of the electron-transporting layer (b) to the cathode (a) was manufactured.

EXAMPLE 84

A device having the same device structure as in Example 69 and constructed with a laminate using BAlq and the platinum complex obtained in Example 4 for the light-emitting layer (d), conducting vacuum vapor deposition simultaneously (doping amount 6% by weight), using BAlq for the hole blocking layer (c), and vacuum vapor depositing LiF to 0.5 nm and Al to 100 nm thickness successively from the side of the electron-transporting layer (b) to the cathode (a) was manufactured.

EXAMPLE 85

A device having the same device structure as in Example 27 and constructed with a laminate formed by using the platinum complex (doping amount 6% by weight) obtained in Example 48 for the light-emitting layer (d), and vacuum vapor depositing LiF to 0.5 nm and Al to 100 nm thickness successively from the side of the electron-transporting layer (b) to the cathode (a) was manufactured.

The result for the evaluation of the devices manufactured in the examples described above are shown below.

TABLE 1

| Example No. | EL peak (nm) | CIE chromaticity (x, y) @100 cd/m² | External quantum efficiency (%) @100 cd/m² | Power efficiency (lm/W) @100 cd/m² |
| --- | --- | --- | --- | --- |
| 70 | 510.6 | 0.32, 0.59 | 1.2 | 1.1 |
| 71 | 610.0 | 0.63, 0.36 | 10.5 | 6.7 |
| 72 | 510.0 | 0.35, 0.59 | 5.3 | 5.0 |
| 73 | 619.8 | 0.66, 0.34 | 10.1 | 4.8 |
| 74 | 614.6 | 0.64, 0.35 | 7.8 | 3.5 |
| 75 | 605.5 | 0.62, 0.37 | 7.6 | 4.6 |
| 76 | 613.2 | 0.64, 0.35 | 5.9 | 3.1 |
| 77 | 492.5 | 0.36, 0.49 | 4.1 | 3.8 |
| 78 | 505.5 | 0.31, 0.51 | 1.2 | 1.3 |
| 79 | 623.3 | 0.67, 0.33 | 9.3 | 3.6 |
| 80 | 594.7 | 0.52, 0.44 | 1.4 | 0.8 |
| 81 | 610.0 | 0.64, 0.36 | 10.6 | 5.9 |
| 82 | 501.2 | 0.27, 0.58 | 5.1 | 5.6 |
| 83 | 618.4 | 0.64, 0.36 | 9.2 | 4.6 |
| 84 | 610.0 | 0.64, 0.36 | 10.6 | 5.9 |
| 85 | 635.0 | 0.67, 0.32 | 7.1 | 4.7 |

The invention claimed is:

1. A platinum complex represented by the following general formula (1):

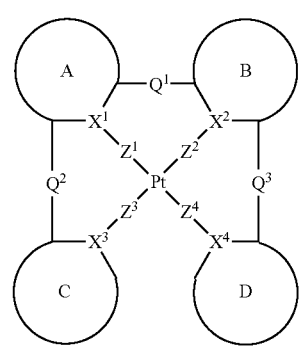

(wherein two rings of ring A, ring B, ring C, and ring D represent nitrogen-containing heterocyclic rings which may have substituent(s) and the remaining two rings of them represent aryl rings or hetero aryl rings which may have substituent(s), the ring A and the ring B, or/and the ring A and the ring C, or/and the ring B and the rind D may form condensed rings, and each of the rings and $R^1$, $R^2$, $R^3$, $R^4$ or $R^5$ described later may form a condensed ring; two of $X^1$, $X^2$, $X^3$, and $X^4$ represent nitrogen atoms coordination bonded to a platinum atom and the remaining two of them represent carbon atoms or nitrogen atoms. $Q^1$, $Q^2$, and $Q^3$ each represent independently a bivalent atom (group) or single bond providing that $Q^1$, $Q^2$, and $Q^3$ do not represent single bond simultaneously, and two of $Z^1$, $Z^2$, $Z^3$, and $Z^4$ represent coordination bonds, and the remaining two of them represent covalent bonds, oxygen atoms or sulfur atoms).

2. A platinum complex according to claim 1, wherein, in the general formula (1), a bivalent atom (group) represented by each of $Q^1$, $Q^2$, and $Q^3$ is —$(CR^1R^2)_{n1}$—, —$O(CR^1R^2)_{n1}$ O—, —$(O)_{n2}C(=O)(O)_{n3}$—, oxygen atom, sulfur atom, —$NR^3$—, —$BR^{3a}$—, —$S(=O)$—, —$SO_2$—, —$O(SO_2)$ O—, —$Si(R^4R^5)$—, —$OSi(R^4R^5)O$—, or —$C(=CR^aR^b)$—, (where $R^1$ and $R^2$ each represent independently hydrogen atom, alkyl group, aralkyl group, aryl group, or alkoxy group; n1 represents an integer of 1 to 3, and n2 and n3 each represent independently an integer of 0 or 1; $R^3$ represents hydrogen atom, alkyl group, aralkyl group, or aryl group, $R^{3a}$ represents alkyl group, aralkyl group, or aryl group; $R^4$ and $R^5$ each represent independently alkyl group, aralkyl group or aryl group; $R^a$ and $R^b$ each represent independently hydrogen atom, alkyl group, aralkyl group, aryl group, or cyano group; and $R^1$ and $R^2$, $R^4$ and $R^5$, or $R^a$ and $R^b$ may join to each other to form a ring which may contain a hetero atom in the ring together with the atom substituted with each of them).

3. A platinum complex according to claim 1, wherein two rings of the ring A, ring B, ring C and ring D of the compound represented by the general formula (1) are 5-membered or 6-membered nitrogen-containing heterocyclic rings which may have a substituent, and one or two 5- or 6-membered aromatic hydrocarbon ring or aromatic heterocyclic ring may be condensed to said ring to form condensed rings.

4. A platinum complex according to claim 1, wherein two of the rings of the ring A, ring B, ring C, and the ring D of the compound represented by the general formula (1) are nitrogen-containing heterocyclic rings which may have substituent(s) selected from the group consisting of pyridine ring, diazine ring, triazine ring, pyrrole ring, diazole ring, triazole ring, thiazole ring, thiadiazole ring, oxazole ring, oxadiazole ring, benzopyridine ring, benzothiazine ring, and benzopyrrole group which may have substituent(s) respectively.

5. A platinum complex according to claim 1, wherein two rings of the ring A, ring B, ring C, and ring D of the compound represented by the general formula (1) are nitrogen-containing heterocyclic rings which may have substituent(s) and the remaining two rings are 6-membered aromatic hydrocarbon rings or aromatic heterocyclic rings, or 5-membered aromatic heterocyclic rings which may have substituent(s), which are aryl rings or heteroaryl rings where one or two 5- or 6-membered aromatic hydrocarbon rings or aromatic heterocyclic rings may be condensed to said rings to form condensed rings.

6. A platinum complex according to claim 1, wherein two rings of the ring A, ring B, ring C, and ring D of the compound represented by the general formula (1) are nitrogen-containing heterocyclic rings which may have substituent(s) and the remaining two rings are aryl rings or heteroaryl rings which may have substituent(s), selected from benzene ring, pyridine ring, diazine ring, triazine ring, pyrrole ring, diazole ring, furan ring, thiophene ring, oxazole ring, and thiazole ring which may have a substituent respectively, or condensed rings where one or two 5- or 6-membered aromatic hydrocarbon rings or aromatic heterocyclic rings are condensed to said rings.

7. A platinum complex according to claim 1 represented by the following general formula (2):

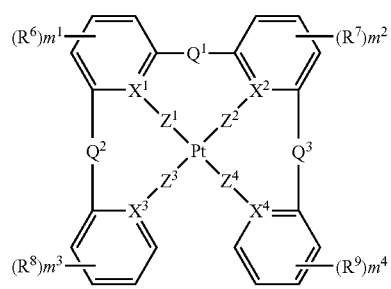

(2)

(wherein $R^6$, $R^7$, $R^8$, and $R^9$ each represent independently alkyl group, halogenated alkyl group, aralkyl group, alkenyl group, alkynyl group, aryl group, amino group, mono- or di-alkyl amino group, mono or di-aralkyl amino group, mono- or di-aryl amino group, alkoxy group, alkenyloxy group, aralkyloxy group, aryloxy group, heteroaryloxy group, acyl group, alkoxycarbonyl group, aryloxycarbonyl group, acyloxy group, acylamino group, alkoxycarbonylamino group, aryloxycarbonylamino group, aralkyloxycarbonylamino group, sulfonylamino group, sulfamoyl group, carbamoyl group, alkylthio group, aralkylthio group, arylthio group, heteroarylthio group, alkanesulfonyl group, arenesulfonyl group, alkanesulfinyl group, arenesulfinyl group, ureido group, substituted phosphoramidate group, hydroxyl group, mercapto group, halogen atom, cyano group, sulfo group, carboxyl group, nitro group, hydroxamic acid group, sulfino group, hydrazino group, heterocyclic group, trialkylsilyl group or triarylsilyl group, and $R^6$ and $R^7$, $R^6$ and $R^8$ or/and $R^7$ and $R^9$ may form condensed rings; $m^1$, $m^2$, $m^3$, and $m^4$ each represent the number of $R^6$, $R^7$, $R^8$, and $R^9$ and independently represent an integer of 0 to 3; in a case where each of $m^1$, $m^2$, $m^3$, and $m^4$ is an integer of 2 or greater, plural $R^6$, $R^7$, $R^8$, and $R^9$ may be different from each other and further, a group of $R^6$, a group of $R^7$, a group of $R^8$, and a group of $R^9$ may join to each other to form a condensed ring structure; $Q^1$, $Q^2$, and $Q^3$ each represent independently $-(CR^1R^2)_{n1}-$, $-O(CR^1R^2)_{n1}O-$, $-(O)_{n2}C(=O)(O)_{n3}-$, oxygen atom, sulfur atom, $-NR^3-$, $-BR^{3a}-$, $-S(=O)-$, $-SO_2-$, $-O(SO_2)O-$, $-Si(R^4R^5)-$, $-OSi(R^4R^5)O-$, $-C(=CR^aR^b)-$, or a single bond providing that $Q^1$, $Q^2$, and $Q^3$ do not represent single bond simultaneously; $R^1$ and $R^2$ in $Q^1$, $Q^2$, and $Q^3$ each represent independently hydrogen atom, alkyl group, aralkyl group, aryl group, or alkoxy group; n1 represents an integer of 1 to 3 and n2 and n3 each represent independently an integer of 0 or 1; $R^3$ represents hydrogen atom, alkyl group, aralkyl group, or aryl group, and $R^{3a}$ represents alkyl group, aralkyl group or aryl group; $R^4$ and $R^5$ each represent independently alkyl group, aralkyl group or aryl group; $R^a$ and $R^b$ each represent independently hydrogen atom, alkyl group, aralkyl group, aryl group, or cyano group; $R^1$ and $R^2$, $R^4$ and $R^5$, or $R^a$ and $R^b$ may join to each other to form a ring which may contain a hetero atom in the ring together with atoms substituted with each of them; two of $X^1$, $X^2$, $X^3$, and $X^4$ represent nitrogen atoms coordination bonded to the platinum atom and the remaining two of them represent carbon atoms; and two of $Z^1$, $Z^2$, $Z^3$, and $Z^4$ represent coordination bonds, and the remaining two of them represent covalent bonds, oxygen atoms or sulfur atoms).

8. A light-emitting device in which a light-emitting layer or plural thin organic compound layers containing a light-emitting layer are formed between a pair of electrodes, in which at least one layer is a layer containing at least one kind of platinum complexes represented by the general formula (1):

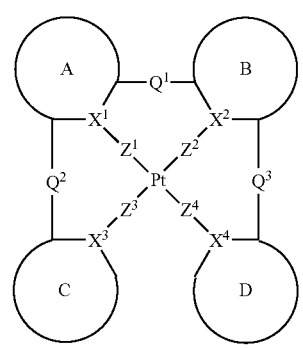

(1)

(wherein two rings of ring A, ring B, ring C, and ring D represent nitrogen-containing heterocyclic rings which may have substituent(s) and the remaining two rings of them represent aryl rings or hetero aryl rings which may have substituent(s), the ring A and the ring B, or/and the ring A and the ring C, or/and the ring B and the rind D may form condensed rings, and each of the rings and $R^1$, $R^2$, $R^3$, $R^4$ or $R^5$ described later may form a condensed ring; two of $X^1$, $X^2$, $X^3$, and $X^4$ represent nitrogen atoms coordination bonded to a platinum atom and the remaining two of them represent carbon atoms or nitrogen atoms. $Q^1$, $Q^2$, and $Q^3$ each represent independently a bivalent atom (group) or single bond providing that $Q^1$, $Q^2$, and $Q^3$ do not represent single bond simultaneously, and two of $Z^1$, $Z^2$, $Z^3$, and $Z^4$ represent coordination bonds, and the remaining two of them represent covalent bonds, oxygen atoms or sulfur atoms);

or the general formula(2):

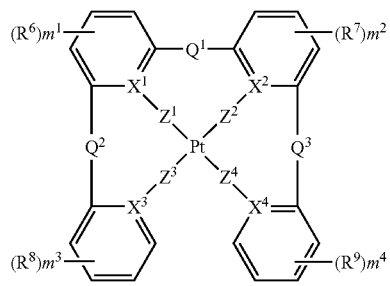

(wherein $R^6$, $R^7$, $R^8$, and $R^9$ each represent independently alkyl group, halogenated alkyl group, aralkyl group, alkenyl group, alkynyl group, aryl group, amino group, mono- or di-alkyl amino group, mono or di-aralkyl amino group, mono- or di-aryl amino group, alkoxy group, alkenyloxy group, aralkyloxy group, aryloxy group, heteroaryloxy group, acyl group, alkoxycarbonyl group, aryloxycarbonyl group, acyloxy group, acylamino group, alkoxycarbonylamino group, aryloxycarbonylamino group, aralkyloxycarbonylamino group, sulfonylamino group, sulfamoyl group, carbamoyl group, alkylthio group, aralkylthio group, arylthio group, heteroarylthio group, alkanesulfonyl group, arenesulfonyl group, alkanesulfinyl group, arenesulfinyl group, ureido group, substituted phosphoramidate group, hydroxyl group, mercapto group, halogen atom, cyano group, sulfo group, carboxyl group, nitro group, hydroxamic acid group, sulfino group, hydrazino group, heterocyclic group, trialkylsilyl group or triarylsilyl group, and $R^6$ and $R^7$, $R^6$ and $R^8$ or/and $R^7$ and $R^9$ may form condensed rings; $m^1$, $m^2$, $m^3$, and $m^4$ each represent the number of $R^6$, $R^7$, $R^8$, and $R^9$ and independently represent an integer of 0 to 3; in a case where each of $m^1$, $m^2$, $m^3$, and $m^4$ is an integer of 2 or greater, plural $R^6$, $R^7$, $R^8$, and $R^9$ may be different from each other and further, a group of $R^6$, a group of $R^7$, a group of $R^8$, and a group of $R^9$ may join to each other to form a condensed ring structure; $Q^1$, $Q^2$, and $Q^3$ each represent independently —$(CR^1R^2)_{n1}$—, —$O(CR^1R^2)_{n1}O$—, —$(O)_{n2}C(=O)(O)_{n3}$—, oxygen atom, sulfur atom, —$NR^3$—, —$BR^{3a}$—, —$S(=O)$—, —$SO_2$—, —$O(SO_2)O$—, —$Si(R^4R^5)$—, —$OSi(R^4R^5)O$—, —$C(=CR^aR^b)$—, or a single bond providing that $Q^1$, $Q^2$, and $Q^3$ do not represent single bond simultaneously; $R^1$ and $R^2$ in $Q^1$, $Q^2$, and $Q^3$ each represent independently hydrogen atom, alkyl group, aralkyl group, aryl group, or alkoxy group; n1 represents an integer of 1 to 3 and n2 and n3 each represent independently an integer of 0 or 1; $R^3$ represents hydrogen atom, alkyl group, aralkyl group, or aryl group, and $R^{3a}$ represents alkyl group, aralkyl group or aryl group; $R^4$ and $R^5$ each represent independently alkyl group, aralkyl group or aryl group; $R^a$ and $R^b$ each represent independently hydrogen atom, alkyl group, aralkyl group, aryl group, or cyano group; $R^1$ and $R^2$, $R^4$ and $R^5$, or $R^a$ and $R^b$ may join to each other to form a ring which may contain a hetero atom in the ring together with atoms substituted with each of them; two of $X^1$, $X^2$, $X^3$, and $X^4$ represent nitrogen atoms coordination bonded to the platinum atom and the remaining two of them represent carbon atoms; and two of $Z^1$, $Z^2$, $Z^3$, and $Z^4$ represent coordination bonds, and the remaining two of them represent covalent bonds, oxygen atoms or sulfur atoms).

9. A light-emitting device according to claim 8, wherein the light-emitting device is an organic electroluminescence device.

10. A light-emitting device according to claim 8, wherein the platinum complex contained in at least one layer may function as a doping material in the light-emitting layer of the organic electroluminescence device.

11. A compound represented by the following general formula (3):

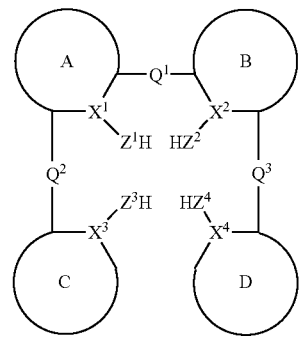

(wherein two rings of ring A, ring B, ring C, and ring D represent nitrogen-containing heterocyclic rings which may have substituent(s) and the remaining two rings of them represent aryl rings or hetero aryl rings which may have substituent(s), the ring A and the ring B, the ring A and the ring C or/and the ring B and the ring D may form condensed ring, and each of the rings and $Q^1$, $Q^2$, and $Q^3$ to be described below may form a condensed ring (excluding the case where $Q^1$, $Q^2$, and $Q^3$ are oxygen atoms and sulfur atoms); two of $X^1$, $X^2$, $X^3$, and $X^4$ represent nitrogen atoms and remaining two of them represent carbon atoms or nitrogen atoms; $Q^1$, $Q^2$, and $Q^3$ each represent independently —$O(CR^1R^2)_{n1}O$—, —$O(CR^1R^2)_{n1}O$—, —$(O)_{n2}C(=O)(O)_{n3}$—, oxygen atom, sulfur atom, —$NR^3$—, —$BR^{3a}$—, —$S(=O)$—, —$SO_2$—, —$O(SO_2)O$—, —$Si(R^4R^5)$—, —$OSi(R^4R^5)O$—, —$C(=CR^aR^b)$—, (where $R^1$ and $R^2$ each represent independently hydrogen atom, alkyl group, aralkyl group, aryl group, or alkoxy group; n1 represents an integer of 1 to 3, and n2 and n3 each represent independently an integer of 0 or 1; $R^3$ represents hydrogen atom, alkyl group, aralkyl group, or aryl group, $R^{3a}$ represents alkyl group, aralkyl group, or aryl group; $R^4$ and $R^5$ each represent independently alkyl group, aralkyl group or aryl group; $R^a$ and $R^b$ each represent independently hydrogen atom, alkyl group, aralkyl group, aryl group, or cyano group; and $R^1$ and $R^2$, $R^4$ and $R^5$, or $R^a$ and $R^b$ may join to each other to form a ring which may contain a hetero atom in the ring together with the atom substituted with each of them); or a single bond providing that $Q^1$, $Q^2$, and $Q^3$ do not represent single bond simultaneously; in a case where $X^1$, $X^2$, $X^3$, and $X^4$ are nitrogen atoms capable of coordination bond, $Z^1H$, $Z^2H$, $Z^3H$, and $Z^4H$ bonded thereto are not present, in a case where $X^1$, $X^2$, $X^3$, and $X^4$ are carbon atoms, $Z^1$, $Z^2$, $Z^3$, and $Z^4$ bonded thereto represent covalent bonds, oxygen atoms or sulfur atoms and, in a case where $X^1$, $X^2$, $X^3$, and $X^4$ are nitrogen atoms capable of covalent bond, $Z^1$, $Z^2$, $Z^3$ and $Z^4$ bonded thereto represent covalent bonds).

12. A compound according to claim 11, wherein two rings of the ring A, ring B, ring C and ring D of the compound represented by the general formula (3) are 5-membered or 6-membered nitrogen-containing heterocyclic rings which may have substituent(s), and one or two 5- or 6-membered aromatic hydrocarbon rings or aromatic heterocyclic rings may be condensed to said rings to form condensed rings.

13. A compound according to claim 11, wherein two rings of the ring A, ring B, ring C, and the ring D of the compound represented by the general formula (3) are nitrogen-containing heterocyclic rings which may have substituent(s), selected from the group consisting of a pyridine ring, diazine ring, triazine ring, pyrrole ring, diazole ring, triazole ring, thiazole ring, thiadiazole ring, oxazole ring, oxadiazole ring, benzopyridine ring, benzothiazine ring, and benzopyrrole group which may have substituent(s) respectively.

14. A compound according to claim 11, wherein two rings of the ring A, ring B, ring C, and ring D of the compound represented by the general formula (3) are nitrogen-containing heterocyclic rings which may have substituent(s) and the remaining two rings are 6-membered aromatic hydrocarbon rings or aromatic heterocyclic rings, or 5-membered aromatic heterocyclic rings which may have substituent(s), which are aryl rings or heteroaryl rings where one or two 5- or 6-membered aromatic hydrocarbon rings or aromatic heterocyclic rings may be condensed to said rings to form condensed rings.

15. A compound according to claim 11, wherein two rings of the ring A, ring B, ring C, and ring D of the compound represented by the general formula (3) are nitrogen-containing heterocyclic rings which may have substituent(s) and the remaining two rings are aryl rings or heteroaryl rings which may have substituent(s), selected from benzene ring, pyridine ring, diazine ring, triazine ring, pyrrole ring, diazole ring, furan ring, thiophene ring, oxazole ring, and thiazole ring which may have substituent(s) respectively, or condensed rings where one or two 5- or 6-membered aromatic hydrocarbon rings or aromatic heterocyclic rings are condensed to said rings.

16. A compound according to claim 10 represented by the following general formula (4):

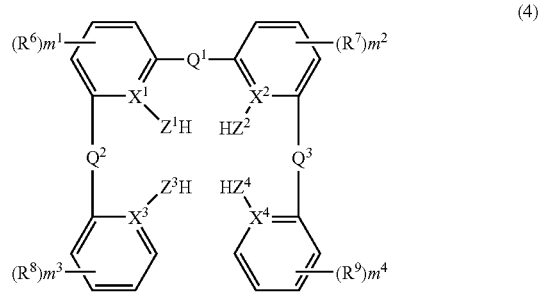

(4)

(wherein $R^6$, $R^7$, $R^8$, and $R^9$ each represent independently alkyl group, halogenated alkyl group, aralkyl group, alkenyl group, alkynyl group, aryl group, amino group, mono- or di-alkyl amino group, mono- or di-aralkyl amino group, mono- or di-aryl amino group, alkoxy group, alkenyloxy group, aralkyloxy group, aryloxy group, heteroaryloxy group, acyl group, alkoxycarbonyl group, aryloxycarbonyl group, acyloxy group, acylamino group, alkoxycarbonylamino group, aryloxycarbonylamino group, aralkyloxycarbonylamino group, sulfonylamino group, sulfamoyl group, carbamoyl group, alkylthio group, aralkylthio group, arylthio group, heteroarylthio group, alkanesulfonyl group, arenesulfonyl group, alkanesulfinyl group, arenesulfinyl group, ureido group, substituted phosphoramidate group, hydroxyl group, mercapto group, halogen atom, cyano group, sulfo group, carboxyl group, nitro group, hydroxamic acid group, sulfino group, hydrazino group, heterocyclic group, trialkylsilyl group or triarylsilyl group, and $R^6$ and $R^7$, $R^6$ and $R^8$ or/and $R^7$ and $R^9$ may form condensed rings; $m^1$, $m^2$, $m^3$, and $m^4$ each represent the number of $R^6$, $R^7$, $R^8$, and $R^9$ and independently represent an integer of 0 to 3; in a case where each of $m^1$, $m^2$, $m^3$, and $m^4$ is an integer of 2 or greater, plural $R^6$, $R^7$, $R^8$, and $R^9$ may be different from each other and further, a group of $R^6$, a group of $R^7$, a group of $R^8$, and a group of $R^9$ may join to each other to form a condensed ring structure; $Q^1$, $Q^2$, and $Q^3$ each represent independently $-(CR^1R^2)_{n1}-$, $-O(CR^1R^2)_{n1}O-$, $-(O)_{n2}C(=O)(O)_{n3}-$, oxygen atom, sulfur atom, $-NR^3-$, $-BR^{3a}-$, $-S(=O)-$, $-SO_2-$, $-O(SO_2)O-$, $-Si(R^4R^5)-$, $-OSi(R^4R^5)O-$, $-C(=CR^aR^b)-$, or a single bond providing that $Q^1$, $Q^2$, and $Q^3$ do not represent single bond simultaneously; $R^1$ and $R^2$ in $Q^1$, $Q^2$, and $Q^3$ each represent independently hydrogen atom, alkyl group, aralkyl group, aryl group, or alkoxy group; n1 represents an integer of 1 to 3 and n2 and n3 each represent independently an integer of 0 or 1; $R^3$ represents hydrogen atom, alkyl group, aralkyl group, or aryl group, and $R^{3a}$ represents alkyl group, aralkyl group or aryl group; $R^4$ and $R^5$ each represent independently alkyl group, aralkyl group or aryl group; $R^a$ and $R^b$ each represent independently hydrogen atom, alkyl group, aralkyl group, aryl group, or cyano group; $R^1$ and $R^2$, $R^4$ and $R^5$, or $R^a$ and $R^b$ may join to each other to form a ring which may contain a hetero atom in the ring together with atoms substituted with each of them; two of $X^1$, $X^2$, $X^3$, and $X^4$ represent nitrogen atoms and the remaining two of them represent carbon atoms; two of $Z^1$, $Z^2$, $Z^3$, and $Z^4$ represent coordination bonds, and the remaining two of them represent covalent bonds, oxygen atoms or sulfur atoms; and H represents a hydrogen atom).

* * * * *